US008008000B2

(12) United States Patent
Bartholomeusz et al.

(10) Patent No.: US 8,008,000 B2
(45) Date of Patent: Aug. 30, 2011

(54) VIRAL VARIANTS DETECTION AND APPLICATION

(75) Inventors: Angeline Ingrid Bartholomeusz, Carnegie (AU); Stephen Alister Locarnini, East St. Kilda (AU); Anna Ayres, West Brunswick (AU); Lilly Ka Wai Yuen, Bullen (AU); Joseph John Sasadeusz, Camberwell (AU)

(73) Assignees: Melbourne Health, Victoria (AU); Austin Health, Victoria (AU); Southern Health, Victoria (AU); Alfred Health, Victoria (AU); St. Vincent's Hospital Melbourne, Victoria (AU)

( * ) Notice: Subject to any disclaimer, the term of this patent is extended or adjusted under 35 U.S.C. 154(b) by 245 days.

(21) Appl. No.: 12/346,622

(22) Filed: Dec. 30, 2008

(65) Prior Publication Data
US 2009/0155312 A1 Jun. 18, 2009

Related U.S. Application Data

(63) Continuation of application No. 10/576,906, filed as application No. PCT/AU2004/001440 on Oct. 20, 2004, now Pat. No. 7,875,423.

(30) Foreign Application Priority Data

Oct. 21, 2003 (AU) ................................ 2003905776
Feb. 25, 2004 (AU) ................................ 2004900962

(51) Int. Cl.
*C12Q 1/70* (2006.01)
*C12Q 1/00* (2006.01)
*C12N 1/21* (2006.01)

(52) U.S. Cl. ............. 435/5; 435/235.1; 435/236; 435/6; 424/189.1

(58) Field of Classification Search .................. None
See application file for complete search history.

(56) References Cited

FOREIGN PATENT DOCUMENTS

| AU | WO2003/066841 | A1 | * | 8/2003 |
|---|---|---|---|---|
| WO | WO 00/61758 | | | 10/2000 |
| WO | WO 01/94559 | A1 | | 12/2001 |
| WO | WO 03/066841 | | | 8/2003 |
| WO | WO 03/087351 | A1 | | 10/2003 |
| WO | WO 2004/031224 | A2 | | 4/2004 |

OTHER PUBLICATIONS

Westland et al. (Hepatology, Jul. 2003, vol. 38, p. 96-103).*
Angus P. et al., "Resistance to Adefovir Dipivoxil Therapy Associated With the Selection of a Novel Mutation in the HBV Polymerase", *Gastroenterology* 125: 292-297 (2003) XP-002277740.
Chen W.N. et al., "Human Hepatitis B Virus Mutants: Significance of Molecular Changes", *FEBS Letters* 453(3):237-242 (1999), XP004259880.
Stuyver L.J. et al., "Nomenclature for Antiviral-Resistant Human Hepatitis B Virus Mutations in the Polymerase Region", *Hepatology* 33(3):751-757 (2001), XP009029630.
Bartholomew M.M. et al., "Hepatitis-B-Virus Resistance to Lamivudine Given for Recurrent Infection After Orthotopic Liver Transplant Ation", *Lancet* 349(9044):20-22 (1997), XP004843545.
Bartholomeusz A. et al., "Mutations in the Hepatitis B Virus Polymerase Gene that are Associated with Resistance to Famciclovir and Lamivudine", *International Antiviral News* 5(8):123-124 (1997), XP002044248.
Alestig E. et al., "Phylogenetic Origin of Hepatitis B Virus Strains with Precore C-1858 Variant", *Journal of Clinical Microbiology* 39(9):3200-3203 (2001), XP002419805.
Günther S. et al., "Analysis of Hepatitis B Virus Populations in an Interferon-α-Treated Patient Reveals Predominant Mutations in the C-Gene and Changing e-Antigenicity", *Virology* 244W:146-160 (1998), XP004845022.
Torres J. et al., "Restoration of Replication Phenotype of Lamivudine-Resistant Hepatitis B Virus Mutants by Compensatory Changes in the "Fingers" Subdomain of the Viral Polymerase Selected as a consequence of Mutations in the Overlapping S Gene", *Virology*, 299: 88-99 (2002).
Ono S. K. et al., "The Polymerase L528M Mutation Cooperates with Nucleotide Binding-Site Mutations, Increasing Hepatitis B Virus Replication and Drug Resistance", *The Journal of Clinical Investigation*, 107(4): 449-455 (2001).

* cited by examiner

*Primary Examiner* — Agnieszka Boesen
(74) *Attorney, Agent, or Firm* — Baker Botts L.L.P.

(57) ABSTRACT

The present invention relates generally to viral variants exhibiting reduced sensitivity to particular agents and/or reduced interactivity with immunological reagents. More particularly, the present invention is directed to hepatitis B virus (HBV) variants exhibiting complete or partial resistance to nucleoside or nucleotide anal Figure 4: Patient A nt sequence

```
          10         20         30         40         50
GCTTCCACCAATCGGCAGGCAGGAAGACAGCCTACTCCCATCTCTCCACC
          60         70         80         90        100
TCTAAGAGACAGTCATCCTCAGGCCATGCAGTGGAACTCCAGCACATTCC
         110        120        130        140        150
ACCATGCTCTGCTAGATCCCAGACCTGCTGGTGGCTCCAGTTCCGGAACA
         160        170        180        190        200
GTAAACCCTGTTCCGACTACTGCCTCTCCCATATCGTCAATCTTCTCGAG
         210        220        230        240        250
GACTGGGGACCCTGCGCCGAATATGGAGAGCACCACATCAGGATTCCTAG
         260        270        280        290        300
GACCCCTGCTCGTGTTACAGGCGGGGTTTTCTTGTTGACAAGAATCCTC
         310        320        330        340        350
ACAATACCAAAGAGTCTAGACTCGTGGTGGACTTCTCTCAATTTTCTAGG
         360        370        380        390        400
GGGAGCACCCACGTGTCCTGGCCAAAATTTGCAGTCCCCAACCTCCAATC
         410        420        430        440        450
ACTCACCAACCTCTTGTCCTCCAATTTGTCCTGGTTATCGCTGGATGTGT
         460        470        480        490        500
CTGCGGCGTTTTATCATCTTCCTCTTCATCCTGCTGCTATGCCTCATCTT
         510        520        530        540        550
CTTGTTGGTTCTTCTGGACTACCAAGGTATGTTGCCCGTTTGTCCTCTAC
         560        570        580        590        600
TTCCAGGAACATCAACTACCAGCACGGGACCATGCAAGACCTGCACGACT
         610        620        630        640        650
CCTGCTCAAGGAACCTCTATGTTTCCCTCTTGTTGCTGTACAAAACCTTC
         660        670        680        690        700
GGACGGAAATTGCACTTGTATTCCCATCCCATCATCTTGGGCTTTCGTAA
         710        720        730        740        750
GATTCCTATGGGAGTGGGCCTCAGTCCGTTTCTCCTGGTTCAGTTTACTA
         760        770        780        790        800
GTGCCATTTGTTCAGTGGTTCGTAGGGCTTTCCCCCACTGTTTGGCTTTC
         810        820        830        840        850
```

```
AGTTATATGGATGATGTGGTATTGGGGGCCAAGTCTGTACAACATCTTGA
        860       870       880       890       900
ATCCCTTTATACCGCTATTACCAATTTTCTTTTGTCTTTGGGTATACATT
        910       920       930       940       950
TAAACCCTAATAAAACCAAGCGTTGGGGCTACTCCCTTAACTTCATGGGA
        960       970       980       990      1000
TATGTAATTGGAAGTTGGGGTACCTTGCCACAGGAACATATTGTACAAAA

AATCAAA
```

Figure 4

Figure 5: Patient A. HBV Polymerase sequence

```
         10        20        30        40        50
EDWGPCAEYGEHHIRIPRTPARVTGGVFLVDKNPHNTKESRLVVDFSQFS 60        70        80        90       100
RGSTHVSWPKFAVPNLQSLTNLLSSNLSWLSLDVSAAFYHLPLHPAAMPH 110       120       130       140       150
LLVGSSGLPRYVARLSSTSRNINYQHGTMQDLHDSCSRNLYVSLLLLYKT 160       170       180       190       200
FGRKLHLYSHPIILGFRKIPMGVGLSPFLLVQFTSAICSVVRRAFPHCLA 210       220       230       240       250
FSYMDDVVLGAKSVQHLESLYTAITNFLLSLGIHLNPNKTKRWGYSLNFM 260       270
GYVIGSWGTLPQEHIVQKIK
```

Figure 5

Figure 6: Patient A HBV HbsAg sequence

```
           10        20        30        40        50
   MESTTSGFLGPLLVLQAGFFLLTRILTIPKSLDSWWTSLNFLGGAPTCPG 60        70        80        90       100
   QNLQSPTSNHSPTSCPPICPGYRWMCLRRFIIFLFILLLCLIFLLVLLDY 110       120       130       140       150
   QGMLPVCPLLPGTSTTSTGPCKTCTTPAQGTSMFPSCCCTKPSDGNCTCI 160       170       180       190       200
   PIPSSWAFVRFLWEWASVRFSWFSLLVPFVQWFVGLSPTVWLSVIWMMWY 210       220
   WGPSLYNILNPFIPLLPIFFCLWVYI
```

Figure 6

Figure 7: Patient B HBV NT sequence

```
          10        20        30        40        50
TCTGTCTCCACCTTTGAGAGACACTCATCCTCAGGCCATGCAGTGGAACT
          60        70        80        90       100
CCACAACCTTCCACCAAACTCTGCAAGATCCCAGAGTGAGAGGCCTGTAT
         110       120       130       140       150
TTCCCTGCTGGTGGCTCCAGTTCAGGAACAGTAAACCCTGTTCCGACTTC
         160       170       180       190       200
TGTCTCTCACACATCGTCAATCTTCTCGAGGATTGGGGTCCCTGCGCTGA
         210       220       230       240       250
ACATGGAGAACATCACATCAGGATTCCTAGGACCCCTGCTCGTGTTACAG
         260       270       280       290       300
GCGGGGTTTTTCTTGTTGACAAGAATCCTCACAATACCGCAGAGTCTAGA
         310       320       330       340       350
CTCGTGGTGGACTTCTCTCAATTTTCTAGGGGGAACTACCGTGTGTCTTG
         360       370       380       390       400
GCCAAAATTCGCAGTCCCCAACCTCCAATCACTCACCAACCTCCTGTCCT
         410       420       430       440       450
CCAACTTGTCCTGGTTATCGCTGGATGTATCTGCGGCGTTTTATCATCTT
         460       470       480       490       500
CCTCTTCATCCTGCTGCTATGCCTCATCTTCTTGTTGGTTCTTCTGGACT
         510       520       530       540       550
ATCAAGGTATGTTGCCCGTTTGTCCTCTAATTCCAGGATCTTCAACCACC
         560       570       580       590       600
AGCACGGGACCATGCAGAACCTGCACGACTCCTGCTCAAGGAAACTCTAT
         610       620       630       640       650
GTATCCCTCCTGTTGCTGTACCAAACCTTCGGACGGAAATTGCACCTGTA
         660       670       680       690       700
TTCCCATCCCATCATCCTGGGCTTTCGGAAAATTCCTATGGGAGTGGGCC
         710       720       730       740       750
TCAGCCCGTTTCTCCTGGCTCAGTTTACTAGTGCCATTTGTTCAGTGGTT
```

Figure 7

```
              760        770        780        790        800
    CGTAGGGCTTTCCCCCACTGTTTGGCTTTCAGTTATATGGATGATGTGGT 810        820        830        840        850
    ATTGGGGGCCAAGTCTGTATCGCATCTTGAGTCCCTTTTTACCGCTGTTA 860        870        880        890        900
    CCAATTTTCTTTTGTCTTTGGGTATACATTTAAACCCTCACAAAACAAAA 910        920        930        940        950
    AGATGGGGTCACTCTTTACATTTCATGGGCTATGTCATTGGATGTTATGG 960        970        980
    GTCATTGCCACAAGATCACATCAGACAGAAAA
```

Figure 7 continued

Figure 8: Patient B POLYMERASE sequence

```
          10         20         30         40         50
   EDWGPCAEHGEHHIRIPRTPARVTGGVFLVDKNPHNTAESRLVVDFSQFS 60         70         80         90        100
   RGNYRVSWPKFAVPNLQSLTNLLSSNLSWLSLDVSAAFYHLPLHPAAMPH 110        120        130        140        150
   LLVGSSGLSRYVARLSSNSRIFNHQHGTMQNLHDSCSRKLYVSLLLLYQT 160        170        180        190        200
   FGRKLHLYSHPIILGFRKIPMGVGLSPFLLAQFTSAICSVVRRAFPHCLA 210        220        230        240        250
   FSYMDDVVLGAKSVSHLESLFTAVTNFLLSLGIHLNPHKTKRWGHSLHFM

260
   GYVIGCYGSLPQDHIRQK
```

Figure 8

Figure 9: Patient B HBsAG sequence

```
            10         20         30         40         50
   MENITSGFLGPLLVLQAGFFLLTRILTIPQSLDSWWTSLNFLGGTTVCLG 60         70         80         90        100
   QNSQSPTSNHSPTSCPPTCPGYRWMYLRRFIIFLFILLLCLIFLLVLLDY 110        120        130        140        150
   QGMLPVCPLIPGSSTTSTGPCRTCTTPAQGNSMYPSCCCTKPSDGNCTCI 160        170        180        190        200
   PIPSSWAFGKFLWEWASARFSWLSLLVPFVQWFVGLSPTVWLSVIWMMWY 210        220
   WGPSLYRILSPFLPLLPIFFCLWVYI
```

Figure 9

Figure 10: Patient C HBV NT sequence

```
         10         20         30         40         50
CAGCAGCGCCTCCTCCTGCCTCCTCCAATCGGCAGTCAGGAAGACAGCCT 60         70         80         90        100
ACTCCCATCTCTCCACCTCTAAGAGACAGTCATCCTCAGGCCATGCAGTG 110        120        130        140        150
GAACTCCAGCACATTCCACCAAGCTCTGCTAGATCCCAGAGTGAGGGGCC 160        170        180        190        200
TATATTTTCCTGCTGGTGGCTCCAGTTCCGGAACAGTAAACCCTGTTCCG 210        220        230        240        250
ACTACTGCCTCTCCCATATCGTCAATCTTCTCGAGGACTGGGGACCCTGC 260        270        280        290        300
ACCGAACATGGAGAGCACCACATCAGGATTCCTAGGACCCCTGCTCGCGT 310        320        330        340        350
TACAGGCGGGGTTTTTCTTGTTGACAAGAATCCTCACAATACCACAGAGT 360        370        380        390        400
CTAGACTCGTGGTGGACTTCTCTCAATTTTCTAGGGGGAACACCCAAGTG 410        420        430        440        450
TCCTGGCCAAAATTTGCAGTCCCCAACCTCCAATCACTCACCAACCTCTT 460        470        480        490        500
GTCCTCCAATTTGTCCTGGTTATCGCTGGATGTGTCTGCGGCGTTTTATC 510        520        530        540        550
ATCTTCCTCTTCATCCTGCTGCTATGCCTCATCTTCTTGTGGGGTCTTCT 560        570        580        590        600
GGACTACCAAGGTATGTTGCCCGTTTGTCCTCTACTTCCAGGAACATCAA 610        620        630        640        650
CTACCAGCACGGGACCATGCAAGACCTGCACGACTCCTGCTCAAGGAACC 660        670        680        690        700
TCTATGTTTCCCTCTTGTTGCTGTACAAAACCTTCGGACGGAAATTGCAC
```

Figure 10

```
        710       720       730       740       750
TTGTATTCCCATCCCATCATCTTGGGCTTTCGCAAGATTCCTATGGGAGT 760       770       780       790       800
GGGCCTCAGTCCGTTTCTCCTGGCTCAGTTTACTAGTGCCATTTGTTCAG 810       820       830       840       850
TGGTTCGTAGGGCTTTCCCCCACTGTTTGGCTTTTAGTTATATGGATGAT 860       870       880       890       900
GTGGTATTGGGGGCCAAGTCTGTACAACAYCTTGAATCCCTTTTTACCGC 910       920       930       940       950
TGTTACCAATTTTCTTTTGTCTTTGGGTATACATTTAAACCCTACTAAAA 960       970       980       990      1000
CCAAACGTTGGGGCTACTCCCTTAACTTCATGGGATATGTAATTGGAAGT 1010      1020      1030      1040
TGGGGTACCTTACCACAAGAACATATTGTACACAAAATCAGACAA
```

Figure 10 continued

Figure 11: Patient C Polymerase sequence

```
          10        20        30        40        50
    EDWGPCTEHGEHHIRIPRTPARVTGGVFLVDKNPHNTTESRLVVDFSQFS 60        70        80        90       100
    RGNTQVSWPKFAVPNLQSLTNLLSSNLSWLSLDVSAAFYHLPLHPAAMPH 110       120       130       140       150
    LLVGSSGLPRYVARLSSTSRNINYQHGTMQDLHDSCSRNLYVSLLLLYKT 160       170       180       190       200
    FGRKLHLYSHPIILGFRKIPMGVGLSPFLLAQFTSAICSVVRRAFPHCLA 210       220       230       240       250
    FSYMDDVVLGAKSVQHLESLFTAVTNFLLSLGIHLNPTKTKRWGYSLNFM 260       270
    GYVIGSWGTLPQEHIVHKIRQ
```

Figure 11

Figure 12 Patient C HbsAg sequence

```
          10        20        30        40        50
MESTTSGFLGPLLALQAGFFLLTRILTIPQSLDSWWTSLNFLGGTPKCPG 60        70        80        90       100
QNLQSPTSNHSPTSCPPICPGYRWMCLRRFIIFLFILLLCLIFLWGLLDY 110       120       130       140       150
QGMLPVCPLLPGTSTTSTGPCKTCTTPAQGTSMFPSCCCTKPSDGNCTCI 160       170       180       190       200
PIPSSWAFARFLWEWASVRFSWLSLLVPFVQWFVGLSPTVWLLVIWMMWY 210       220
WGPSLYNXLNPFLPLLPIFFCLWVYI
```

Figure 12

Figure 13; Patient D NT sequence

```
         10        20        30        40        50
CTCCTGCATCTACCAATCGGCAGTCAGGAAGACAGCCTACTCCCATCTCT 60        70        80        90       100
CCACCTCTAAGAGACAGTCATCCTCAGGCCATGCAGTGGAACTCCACAAC 110       120       130       140       150
TTTCCACCAAGCTCTGCTAGATCCCCGAGTGAGGGGCCTCTATTTTCCTG 160       170       180       190       200
CTGGTGGCTCCAGTTCCGGGACAGTAAACCCTGTTCCGACTACTGCCTCT 210       220       230       240       250
CCCATATCGTCAATCTTCTCGAGGACTGGGGACCCTGCACTGAACATGGA 260       270       280       290       300
GAGCACAACATCAGGATTCCTAGGACCCCTGCTCGTGTTACAGGCGGTGT 310       320       330       340       350
TTTTCTTGTTGACAAGAATCCTCACAATACCACAGAGTCTAGACTCGTGG 360       370       380       390       400
TGGACTTCTCTCAATTTTCTAGGGGAAGCACCCGCGTGTCCTGGCCAAAA 410       420       430       440       450
TTCGCAGTCCCCAACCTCCAATCACTCACCAACCTCTTGTCCTCCAATTT 460       470       480       490       500
GTCCTGGCTATCGCTGGATGTGTCTGCGGCGTTTTATCATCTTCCTCTTC 510       520       530       540       550
ATCCTGCTGCTATGCCTCATCTTCTTGTTGGTTCTTCTGGATTACCAAGG 560       570       580       590       600
TATGTTGCCCGTTTGTCCTCTACTTCCAGGAACGTCAACTACCAGCACGG 610       620       630       640       650
GACCATGCAAGACCTGCACGATTCCTGCTCAAGGAACCTCTATGTTTCCC 660       670       680       690       700
TCATGTTGCTGTACAAAACCTTCGGACGGAAACTGCACTTGTATTCCCAT 710       720       730       740       750
CCCATCATCCTGGGCTTTTCGCAAGATTCCTATGGGAGTGGGCCTCAGTCC
```

Figure 13

```
            760       770       780       790       800
GTTTCTCTTGACTCAGTTTACTAGTGCCATTTGTTCAGTGGTTCGTAGGG 810       820       830       840       850
CTTTCCCCCACTGTTTGGCTTTCAGTTATATGGATGATGTGGTATTGGGG 860       870       880       890       900
GCCAAGTCTGTACAACATCTTGAGTCCCTTTATACCGCTATTACCAATTT 910       920       930       940       950
TCTTTTGTCTTTGGGTATACATTTAAACCCTAATAAAACCAAGCGATGGG 960       970       980       990      1000
GTTACTCCCTTAACTTCATGGGATATGTCATTGGAAGTTGGGGACTTTA 1010      1020
CCACAGGAACATATTGTGCTC
```

Figure 13 continued

Figure 14: patient D HBV POL sequence

```
         10         20         30         40         50
EDWGPCTEHGEHNIRIPRTPARVTGGVFLVDKNPHNTTESRLVVDFSQFS 60         70         80         90        100
RGSTRVSWPKFAVPNLQSLTNLLSSNLSWLSLDVSAAFYHLPLHPAAMPH 110        120        130        140        150
LLVGSSGLPRYVARLSSTSRNVNYQHGTMQDLHDSCSRNLYVSLMLLYKT 160        170        180        190        200
FGRKLHLYSHPIILGFRKIPMGVGLSPFLLTQFTSAICSVVRRAFPHCLA 210        220        230        240        250
FSYMDDVVLGAKSVQHLESLYTAITNFLLSLGIHLNPNKTKRWGYSLNFM

260
GYVIGSWGTLPQEHIVL
```

Figure 14

Figure 15 Patient D HBsAg sequence

```
            10        20        30        40        50
    MESTTSGFLGPLLVLQAVFFLLTRILTIPQSLDSWWTSLNFLGEAPACPG 60        70        80        90       100
    QNSQSPTSNHSPTSCPPICPGYRWMCLRRFIIFLFILLLCLIFLLVLLDY 110       120       130       140       150
    QGMLPVCPLLPGTSTTSTGPCKTCTIPAQGTSMFPSCCCTKPSDGNCTCI 160       170       180       190       200
    PIPSSWAFARFLWEWASVRFS*LSLLVPFVQWFVGLSPTVWLSVIWMMWY 210       220
    WGPSLYNILSPFIPLLPIFFCLWVYI
```

Figure 15

Figure 16: Patient E HBV nt sequence

```
         10        20        30        40        50
AGTCATCCTCAGGCCATGCAGTGGAACTCCAGCACATTCCACCAAGCTCT
         60        70        80        90       100
GCTAGATCCCAGAGTGAGGGGCCTATACTTTCCTGCTGGTGGCTCCAGTT
        110       120       130       140       150
CAGGAACAGTAAACCCTGTTCCGACTACTGCCTCTCCCATATCGTCAATC
        160       170       180       190       200
TTCTCGAGGACTGGGGACCCTGCACCGAATATGGAGAGCACCACATCAGG
        210       220       230       240       250
ATTCCTAGGACCCCTGCTCGTGTTACAGGCGGGGTTTTTCTTGTTGACAA
        260       270       280       290       300
GAATCCTCACAATACCACAGAGTCTAGACTCGTGGTGGACTTCTCTCAAT
        310       320       330       340       350
TTTCTAGGGGGAGCACCCGCGTGTCCTGGCCAAAATTTGCAGTCCCCAAC
        360       370       380       390       400
CTCCAATCACTCACTAACCTCTTGTCCTCCAATTTGTCCTGGTTATCGCT
        410       420       430       440       450
GGATGTGTCTGCGGCGTTTTATCATCTTCCTCTTCATCCTGCTGCTATGC
        460       470       480       490       500
CTCATCTTCTTGTTGGTTCTTCTGGACTACCAAGGTATGTTGCCCGTTTG
        510       520       530       540       550
TCCTCTACTTCCAGGAACATCAACTACCAGCACGGGACCATGCAAGACCT
        560       570       580       590       600
GCACGACTCCTGCTCAAGGAACCTCTATGTTTCCCTCTTGTTGTTGTACA
        610       620       630       640       650
AAACCTTCGGACGGAAATTGCACTTGTATTCCCATCCCATCATCTTGGGC
        660       670       680       690       700
TTTCGCAAGATTCCTATGGGAGTGGGCCTCAGTCCGTTTCTCATGGCTCA
```

Figure 16

```
         710       720       730       740       750
GTTTACTAGTGCCATTTGTTCAGTGGTTCGTAGGGCTTTCCCCCACTGTT 760       770       780       790       800
TGGTTTTCAGTTATGTGGATGATGTGGTATTGGGGGCCAAGTCTGCACAA 810       820       830       840       850
CATCTTGAATCCCTTTTTACCGCTATTACCAATTTTCTTTTGTCTTTGGG 860       870       880       890       900
TATACATTTAAACCMTAATAAAACCAAACGTTGGGGCTATTCCCTTAACT 910       920       930       940       950
TTATGGGATATGGAATTGGAAGTTGGGGTCCTGCCCAGGGAAGATGGCAG

GGG
```

Figure 16 continued

Figure 17 Patient E: HBV polymerase

```
         10         20         30         40         50
SSSGHAVELQHIPPSSARSQSEGPILSCWWLQFRNSKPCSDYCLSHIVNL 60         70         80         90        100
LEDWGPCTEYGEHHIRIPRTPARVTGGVFLVDKNPHNTTESRLVVDFSQF 110        120        130        140        150
SRGSTRVSWPKFAVPNLQSLTNLLSSNLSWLSLDVSAAFYHLPLHPAAMP 160        170        180        190        200
HLLVGSSGLPRYVARLSSTSRNINYQHGTMQDLHDSCSRNLYVSLLLLYK 210        220        230        240        250
TFGRKLHLYSHPIILGFRKIPMGVGLSPFLMAQFTSAICSVVRRAFPHCL 260        270        280        290        300
VFSYVDDVVLGAKSAQHLESLFTAITNFLLSLGIHLNXNKTKRWGYSLNF

MGYGIGSWG
```

Figure 17

Figure 18: Patient E HBsAg

```
         10        20        30        40        50
QPTPISPPLRDSHPQAMQWNSSTFHQALLDPRVRGLYFPAGGSSSGTVNP 60        70        80        90       100
VPTTASPISSIFSRTGDPAPNMESTTSGFLGPLLVLQAGFFLLTRILTIP 110       120       130       140       150
QSLDSWWTSLNFLGGAPACPGQNLQSPTSNHSLTSCPPICPGYRWMCLRR 160       170       180       190       200
FIIFLFILLLCLIFLLVLLDYQGMLPVCPLLPGTSTTSTGPCKTCTTPAQ 210       220       230       240       250
GTSMFPSCCCTKPSDGNCTCIPIPSSWAFARFLWEWASVRFSWLSLLVPF 260       270       280       290       300
VQWFVGLSPTVWFSVMWMMWYWGPSLHNILNPFLPLLPIFFCLWVYI*TX

IKPNVGA
```

Figure 18

Figure 19: Patient F: nt sequence

```
         10        20        30        40        50
CCAATCGGCAGTCAGGAAGACAGCCTACTCCCATCTCTCCACCTCTAAGA 60        70        80        90       100
GACAGTCATCCTCAGGCCATGCAGTGGAACTCCAGCACATTCCACCAAGC 110       120       130       140       150
TCTGCTAGATCCCAGAGTGAGGGGCCTATACTTTCCTGCTGGTGGCTCCA 160       170       180       190       200
GTTCCGGAACAGTAAACCCTGTTCCGACTACTGCCTCTCCCATATCGTCA 210       220       230       240       250
ATCTTCTCGAGGACTGGGGACCCTGCACCGAATATGGAGAGCACCACATC 260       270       280       290       300
AGGATTCCTAGGACCCCTGCTCGTGTTACAGGCGGGGTTTTTCTTGTTGA 310       320       330       340       350
CAAGAATCCTCACAATACCACAGAGTCTAGACTCGTGGTGGACTTCTCTC 360       370       380       390       400
AATTTTCTAGGGGGAGCACCCACGTGTCCTGGCCAAAATTTGCAGTCCCC 410       420       430       440       450
AACCTCCAATCACTCACCAACCTCTTGTCCTCCAATTTGTCCTGGTTATC 460       470       480       490       500
GCTGGATGTGTCTGCGGCGTTTTATCATCTTCCTCTTCATCCTGCTGCTA 510       520       530       540       550
TGCCTCATCTTCTTGTTGGTTCTTCTGGACTACCAAGGTATGTTGCCCGT 560       570       580       590       600
TTGTCCTCTACTTCCAGGAACATCAACTACCAGCACGGGACCATGCAAGA 610       620       630       640       650
CCTGCACGACTCCTGCTCAAGGAACCTCTATGTTTCCCTCTTGTTGCTGT
```

Figure 19

```
              660       670       680       690       700
       ACAAAACCTTCGGACGGAAATTGCACTTGTATTCCCATCCCATCATCTTG 710       720       730       740       750
       GGCTTTCGCAAGATTCCTATGGGAGTGGGCCTCAGTCCGTTTCTCCTGGC 760       770       780       790       800
       TCAGTTTACTAGTGCCATTTGTTCAGTGGTTCGTAGGGCTTTCCCCCACT 810       820       830       840       850
       GTTTGGCTTTCAGTTATATGGATGATGTGGTATTGGGGGCCAAGTCTGTA 860       870       880       890       900
       CAACATCTTGAATCCCTTTTTACCGCTGTTACCAATTTTCTTTTGTCTTT 910       920       930       940       950
       GGGTATACATTTAAACCCTACTAAAACTAAACGTTGGGGCTACTCCCTTA 960       970       980
       ACTTCATGGGATATGTAATTGGAAGTTGGGGTACCTTG
```

Figure 19 continued

Figure 20 Patient F Pol Amino acid sequence

```
          10        20        30        40        50
    EDWGPCTEYGEHHIRIPRTPARVTGGVFLVDKNPHNTTESRLVVDFSQFS 60        70        80        90       100
    RGSTHVSWPKFAVPNLQSLTNLLSSNLSWLSLDVSAAFYHLPLHPAAMPH 110       120       130       140       150
    LLVGSSGLPRYVARLSSTSRNINYQHGTMQDLHDCSRNLYVSLLLLYKT 160       170       180       190       200
    FGRKLHLYSHPIILGFRKIPMGVGLSPFLLAQFTSAICSVVRRAFPHCLA 210       220       230       240       250
    FSYMDDVVLGAKSVQHLESLFTAVTNFLLSLGIHLNPTKTKRWGYSLNFM

GYVIGSWG
```

Figure 20

Figure 21 Patient F HBsAg seq

```
            10         20         30         40         50
   MESTTSGFLGPLLVLQAGFFLLTRILTIPQSLDSWWTSLNFLGGAPTCPG 60         70         80         90        100
   QNLQSPTSNHSPTSCPPICPGYRWMCLRRFIIFLFILLLCLIFLLVLLDY 110        120        130        140        150
   QGMLPVCPLLPGTSTTSTGPCKTCTTPAQGTSMFPSCCCTKPSDGNCTCI 160        170        180        190        200
   PIPSSWAFARFLWEWASVRFSWLSLLVPFVQWFVGLSPTVWLSVIWMMWY 210        220
   WGPSLYNILNPFLPLLPIFFCLWVYI
```

Figure 21

Figure 22: Patient G ;HBV nt

```
          10         20         30         40         50
TCCGCCTCCTGCCTCCACCAATCGCCAGTCAGGAAGGCAACCTACCCCGC 60         70         80         90        100
TCTCTCCACCTTTGAGAGACACTCATCCTCAGGCCGTGCAGTGGAACTCC 110        120        130        140        150
ACAACCTTCCACCAAACTCTGCAAGATCCCAGAGTGAGGGGCCTGTATCT 160        170        180        190        200
CCCTGCTGGTGGCTCCAGTTCAGGAACAGCAAACCCTGTTCCGACTACTG 210        220        230        240        250
CCTCTCGCTTATCGTCAATCTTCTCGAGGATTGGGGACCCTGCGCTGAAC 260        270        280        290        300
ATGGAGAACATCACATCAGGACTCCTAGGACCCCTTCTCGTGTTACAGGC 310        320        330        340        350
GGGGTTTTCTTGTTGACAAGAATCCTCACAATACCGCAGAGTCTAGACT 360        370        380        390        400
CGTGGTGGACTTCTCTCAGTTTTCTAGGGGGAACTACCGTGTGTCTTGGC 410        420        430        440        450
CAAAATTCGCGGTCCCCAACCTCCAATCACTCACCAACCTCCTGTCCTCC 460        470        480        490        500
GACTTGTCCTGGTTATCGCTGGATGTATCTGCGGCGTTTTATCATATTCC 510        520        530        540        550
TCTTCATCCTGCTGCTATGCCTCATCTTCTTGTTGGTTCTTCTGGACTAT 560        570        580        590        600
CAAGGTATGTTGCCCGTTTGTCCTCTAATTCCAGGATCCTCAACCACCAG 610        620        630        640        650
CACGGGAACATGCCGAACCTGCACGACTCCTGCTCAAGGAACCTCTATGT 660        670        680        690        700
ATCCCTCCTGTTGCTGTACCAAACCTTCGGACGGAAATTGCACCTGTATT
```

Figure 22

```
       710        720        730        740        750
CCCATCCCATCATCTTGGGCTTTCGGAAAATTCCTATGGGAGTGGGCCTC 760        770        780        790        800
AGCCCGTTTCTCCTGGCTCAGTTTACTAGTGCCATTTGTTCAGTGGTTCG 810        820        830        840        850
TAGGGCTTTCCCCCACTGTTTGGCTTTCAGTTATATGGATGATGTGGTAT 860        870        880        890        900
TGGGGGCCAAGTCTGTACAGCATCTTGAGTCCCTTTTTACCGCTGTTACC 910        920        930        940        950
AATTTTCTTTTGTCTTTGGGTATACATTTAACCCCTAACAAAACAAAGAG 960        970        980        990       1000
ATGGGGTTACTCTCTAAATTTTATGGGCTATGTCATTGGAAGTTATGGGT 1010       1020       1030       1040
CCTTGCCACAAGAACACATTATACTAAAAATCAAAGATTGTTT
```

Figure 22 continued

Figure 23 Patient G HBV POL

```
          10        20        30        40        50
EDWGPCAEHGEHHIRTPRTPSRVTGGVFLVDKNPHNTAESRLVVDFSQFS 60        70        80        90       100
RGNYRVSWPKFAVPNLQSLTNLLSSDLSWLSLDVSAAFYHIPLHPAAMPH 110       120       130       140       150
LLVGSSGLSRYVARLSSNSRILNHQHGNMPNLHDSCSRNLYVSLLLLYQT 160       170       180       190       200
FGRKLHLYSHPIILGFRKIPMGVGLSPFLLAQFTSAICSVVRRAFPHCLA 210       220       230       240       250
FSYMDDVVLGAKSVQHLESLFTAVTNFLLSLGIHLTPNKTKRWGYSLNFM

GYVIGSYG
```

Figure 23

Figure 24: Patient G HbsAg

```
         10         20         30         40         50
MENITSGLLGPLLVLQAGFFLLTRILTIPQSLDSWWTSLSFLGGTTVCLG 60         70         80         90        100
QNSRSPTSNHSPTSCPPTCPGYRWMYLRRFIIFLFILLLCLIFLLVLLDY 110        120        130        140        150
QGMLPVCPLIPGSSTTSTGTCRTCTTPAQGTSMYPSCCCTKPSDGNCTCI 160        170        180        190        200
PIPSSWAFGKFLWEWASARFSWLSLLVPFVQWFVGLSPTVWLSVIWMMWY 210        220
WGPSLYSILSPFLPLLPIFFCLWVYI
```

Figure 24

Figure 25 Patient H nt seq

```
          10        20        30        40        50
CGCCTCCTGCCTCCACCAATCGCCAGTCAGGAAGGCAGCCGACCCCACTG
          60        70        80        90       100
TCTCCACCTTTGAGAGACACTCATCCTCAGGCCGTGCAGTGGAACTCCAC
         110       120       130       140       150
AACCTTCCACCAAACTCTGCAAGATCCCAGAGTGAGAGGCCTGTATTTCC
         160       170       180       190       200
CTGCTGGTGGCTCCAGTTCAGGAACAGTAAACCCTGTTCCGACCACTGCC
         210       220       230       240       250
TCTCCCTTATCGTCAATCTTCTCGAGGATTGGGGACCCTGCGCTGAACAT
         260       270       280       290       300
GGAGAACATCACATCAGGATTCCTAGGACCCCTTCTCGTGTTACAGGCGG
         310       320       330       340       350
GGTTTTTCTTGTTGACAAGAATCCTCACAATACCGCAGAGTCTAGACTCG
         360       370       380       390       400
TGGTGGACTTCTCTCAGTTTTCTAGGGGAAACCACCGTGTGTCTTGGCCA
         410       420       430       440       450
AAATTCGCAGTCCCCAACCTCCAATCACTCACCAACCTCCTGTCCTCCAA
         460       470       480       490       500
CTTGTCCTGGTTATCGCTGGATGTGTCTGCGGCGTTTTATCATATTCCTC
         510       520       530       540       550
TTCATCCTGCTGCTATGCCTCATCTTCTTGTTGGTTCTTCTGGACTATCA
         560       570       580       590       600
AGGTATGTTGCCCGTTTGTCCTCTAATTCCAGGATCCTCAACCACCAGCA
         610       620       630       640       650
CGGGACCATGCCGAACCTGCACGACTCCTGCTCAAGGAACCTCTATGTAT
         660       670       680       690       700
CCCTCCTGTTGCTGTACCAAACCTTCGGACGGAAATTGCACCTGTATTCC
```

Figure 25

```
         710        720        730        740        750
CATCCCATCATCTTGGGCTTTCGCAAAATTCCTATGGGAGTGGGGCTCAG 760        770        780        790        800
CCCGTTTCTCATGGCTCAGTTTACTAGTGCCATTTGTTCAGTGGTTCGTA 810        820        830        840        850
GGGCTTTCCCCCACTGTTTGGCTTTCAGTTATGTGGATGATGTGGTATTG 860        870        880        890        900
GGGGCCAAGTCTGTATCGCATCTTGAGTCCCTTTTTACCGCTGTTACCAA 910        920        930        940        950
TTTTCTTTTGTCTTTGGGTATACATTTAAACCCTAACAAAACGAAAAGAT 960        970        980        990       1000
GGGGTTACTCTTTAAATTTTATGGGGTATGTTATTGGATGTTATGGGTCC 1010       1020
TTGCCACAAGAACACATCGTACAAAAA
```

Figure 25 continued

Figure 26: Patient H HBV pol

```
              10         20         30         40         50
     EDWGPCAEHGEHHIRIPRTPSRVTGGVFLVDKNPHNTAESRLVVDFSQFS 60         70         80         90        100
     RGNHRVSWPKFAVPNLQSLTNLLSSNLSWLSLDVSAAFYHIPLHPAAMPH 110        120        130        140        150
     LLVGSSGLSRYVARLSSNSRILNHQHGTMPNLHDSCSRNLYVSLLLLYQT 160        170        180        190        200
     FGRKLHLYSHPIILGFRKIPMGVGLSPPLMAQFTSAICSVVRRAFPHCLA 210        220        230        240        250
     FSYVDDVVLGAKSVSHLESLFTAVTNFLLSLGIHLNPNKTKRWGYSLNFM

260
     GYVIGCYGSLPQEH
```

Figure 26

Figure 27: Patient H HBsAg

```
          10         20         30         40         50
MENITSGFLGPLLVLQAGFFLLTRILTIPQSLDSWWTSLSFLGETTVCLG 60         70         80         90        100
QNSQSPTSNHSPTSCPPTCPGYRWMCLRRFIIFLFILLLCLIFLLVLLDY 110        120        130        140        150
QGMLPVCPLIPGSSTTSTGPCRTCTTPAQGTSMYPSCCCTKPSDGNCTCI 160        170        180        190        200
PIPSSWAFAKFLWEWGSARFSWLSLLVPFVQWFVGLSPTVWLSVMWMMWY 210        220
WGPSLYRILSPFLPLLPIFFCLWVYI
```

Figure 27

Figure 28 Patient I HBV nt seq

```
         10         20         30         40         50
CAACTTGTCCTGGTTATCGCTGGATGTGTCTGCGGCGTTTTATCATATTC 60         70         80         90        100
CTCTTCATCCTGCTGCTATGCCTCATCTTCTTGTTGGTTCTTCTGGACTA 110        120        130        140        150
TCGAGGTATGTTGCCCGTTTGTCCTCTACTTCCAGGATCTTCAACCACCA 160        170        180        190        200
GCACGGGTCCATGCAGAACCTGCACGACTCCTGCTCAAGGAACCTCTATG 210        220        230        240        250
TATCCCTCATGTTGCTGTACCAAACCTTCGGACGGAAATTGCACCTGTAT 260        270        280        290        300
TCCCATCCCATCATCCTGGGCTTTCGGAAAATTCCTATGGGAGTGGGCCT 310        320        330        340        350
CAGCCCGTTTCTCATGGCTCAGTTTACTAGTGCCATTTGTTCAGTGGTTC 360        370        380        390        400
GTAGGGCTTTCCCCCATTGTTTGGCTTTCAGTTATGTGGATGATGTGGTA 410        420        430        440        450
TTGGGGGCCAAGTCTGTATCGCATCTTGAGTCCCTTTTTACCGCTGTTAC 460        470        480        490        500
CAATTTTCTTTTGTCTCTGGGTATACATTTAAACCCTCACAAAACAAAAA 510        520        530        540        550
GATGGGGTTACTCTTTACATTTCATGGGCTATGTCATCGGATGTTATGGG

560
TCTTTGCCAC
```

Figure 28

Figure 29 Patient I HBV pol

```
          10        20        30        40        50
NLSWLSLDVSAAFYHIPLHPAAMPHLLVGSSGLSRYVARLSSTSRIFNHQ 60        70        80        90       100
HGSMQNLHDSCSRNLYVSLMLLYQTFGRKLHLYSHPIILGFRKIPMGVGL 110       120       130       140       150
SPFLMAQFTSAICSVVRRAFPHCLAFSYVDDVVLGAKSVSHLESLFTAVT 160       170       180
NFLLSLGIHLNPHKTKRWGYSLHFMGYVIGCYGSLP
```

Figure 29

Figure 30 Patient I: HBsAg

```
          10        20        30        40        50
  TCPGYRWMCLRRFIIFLFILLLCLIFLLVLLDYRGMLPVCPLLPGSSTTS 60        70        80        90       100
  TGPCRTCTTPAQGTSMYPSCCCTKPSDGNCTCIPIPSSWAFGKFLWEWAS 110       120       130       140       150
  ARFSWLSLLVPFVQWFVGLSPIVWLSVMWMMWYWGPSLYRILSPFLPLLP 160       170       180
  IFFCLWVYI*
```

Figure 30

Figure 31 Patient J HBV nt seq

```
          10        20        30        40        50
CGCCTCCTCCTGCCTCCACCATCGGCAGTCAGGAAGAAAGCCTACTCCCA 60        70        80        90       100
TCTCTCCACCTCTAAGAGACAGTCATCCTCAGGCCATGCAGTGGAACTCC 110       120       130       140       150
AGCACATTCCACCAAGCTCTGCTAGATCCCARAGTGAGRGGCCTATACTT 160       170       180       190       200
TCCTGCTGGTGGCTCCAGTTCCGGAACAGTAAACCCTGTTCCGACTACTG 210       220       230       240       250
CCTCTCCCATATCGTCAATCTTCTCGAGGACTGGGGACCCTGCACCGAAT 260       270       280       290       300
ATGGAGAGCACAACATCAGGATTCCTAGGACCCCTGCTCGTGTTACAGGC 310       320       330       340       350
GGGGTTTTCTTGTTGACAAGAATCCTCACAATACCACAGAGTCTAGACT 360       370       380       390       400
CGTGGTGGACTTCTCTCAATTTTCTAGGGGGAGCACCCACGTGTCCTGGC 410       420       430       440       450
CAAAATTTGCAGTCCCCAACCTCCAATCACTCACCAACCTCTTGTCCTCC 460       470       480       490       500
AATTTGTCCTGGTTATCGCTGGATGTGTCTGCGGCGTTTTATCATCTTCC 510       520       530       540       550
TCTTCATCCTGCTGCTATGCCTCATCTTCTTGTKGGTTCTTCTGGACTAC 560       570       580       590       600
CAAGGTATGTTGCCCGTTTGTCCTCTACTTCCAGGAACATCAACTACCAG 610       620       630       640       650
CACGGGACCATGCAAGACCTGCACGATTCCTGCTCAAGGAACCTCTATGT 660       670       680       690       700
TTCCCTCTTGTTGCTGTACAAAACCTTCGGACGGAAATTGCACTTGTATT
```

Figure 31

```
         710       720       730       740       750
CCCATCCCATCATCTTGGGCTTTCGCAAGATTCCTATGGGAGTGGGCCTC 760       770       780       790       800
AGTCCGTTTCTCCTGGCTCAGTTTACTAGTGCCATTTGTTCAGTGGTTCG 810       820       830       840       850
TAGGGCTTTCCCCCACTGTTTGGCTTTCAGTTATATGGATGATGTGGTAT 860       870       880       890       900
TGGGGGCCAAGTCTGTACAACATCTTGAATCCCTTTTTACCGCTGTTACC 910       920       930       940       950
AATTTTCTTTTGTCTTTGGGTATACATTTAAACCCTACTAAAACTAAACG 960       970       980       990       1000
TTGGGGCTACTCCCTTAACTTCATGGGATATGTAATTGGAAGTTGGGGTA 1010      1020
CCTTACCACAGGAACATATTGTACACAAA
```

Figure 31 continued

Figure 32 Patient J HBV pol

```
        10         20         30         40         50
EDWGPCTEYGEHNIRIPRTPARVTGGVFLVDKNPHNTTESRLVVDFSQFS 60         70         80         90        100
RGSTHVSWPKFAVPNLQSLTNLLSSNLSWLSLDVSAAFYHLPLHPAAMPH 110        120        130        140        150
LLVGSSGLPRYVARLSSTSRNINYQHGTMQDLHDCSRNLYVSLLLLYKT 160        170        180        190        200
FGRKLHLYSHPIILGFRKIPMGVGLSPFLLAQFTSAICSVVRRAFPHCLA 210        220        230        240        250
FSYMDDVVLGAKSVQHLESLFTAVTNFLLSLGIHLNPTKTKRWGYSLNFM

260
GYVIGSWGTLPQEHIVHK
```

Figure 32

Figure 33. Patient J HBsAg

```
         10        20        30        40        50
MESTTSGFLGPLLVLQAGFFLLTRILTIPQSLDSWWTSLNFLGGAPTCPG 60        70        80        90       100
QNLQSPTSNHSPTSCPPICPGYRWMCLRRFIIFLFILLLCLIFLXVLLDY 110       120       130       140       150
QGMLPVCPLLPGTSTTSTGPCKTCTIPAQGTSMFPSCCCTKPSDGNCTCI 160       170       180       190       200
PIPSSWAFARFLWEWASVRFSWLSLLVPFVQWFVGLSPTVWLSVIWMMWY 210       220
WGPSLYNILNPFLPLLPIFFCLWVYI
```

Figure 33

Figure 34 Patient K HBV nt

```
         10         20         30         40         50
CTCCTCCTGCCTCCACCAATCGGCAGTCAGGAAGACAGCCTACACCCATC 60         70         80         90        100
TCTCCACCTCTAAGAGACAGTCATCCTCAGGCCATGCAGTGGAACTCCAG 110        120        130        140        150
CACATTCCACCAAGCTCTGCTAGATCCCAGAGTGAGGGGCCTATACTTTC 160        170        180        190        200
CTGCTGGTGGCTCCAGTTCAGGAACAGTAAACCCTGTTCCGACTACTGCC 210        220        230        240        250
TCTCCCATATCGTCAATCTTCTCGAGGACTGGGGACCCTGCACCGAATAT 260        270        280        290        300
GGAGAGCACCACATCAGGATTCCTAGGACCCCTGCTCGTGTTACAGGCGG 310        320        330        340        350
GGTTTTTCTTGTTGACAAGAATCCTCACAATACCACAGAGTCTAGACTCG 360        370        380        390        400
TGGTGGACTTCTCTCAATTTTCTAGGGGGAGCACCCACGTGTCCTGGCCA 410        420        430        440        450
AAATTTGCAGTCCCCAACCTCCAATCACTCACCAACCTCTTGTCCTCCAA 460        470        480        490        500
TTTGTCCTGGTTATCGCTGGATGTGTCTGCGGCGTTTTATCATCTTCCTC 510        520        530        540        550
TTCATCCTGCTGCTATGCCTCATCTTCTTGTTGGTTCTTCTGGACTACCA 560        570        580        590        600
AGGTATGTTGCCCGTTTGTCCTCTACTTCCAGGAACATCAACTACCAGCA 610        620        630        640        650
CGGGACCATGCAAGACCTGCACGATTCCTGCTCAAGGAACCTCTATGTTT 660        670        680        690        700
CCCTCTTGTTGCTGTACAAAACCTTCGGACGGAAATTGCACTTGTATTCC
```

Figure 34

```
          710       720       730       740       750
CATCCCATCATCTTGGGCTTTCGCAAGATTCCTATGGGAGTGGGCCTCAG 760       770       780       790       800
TCCGTTTCTCCTGGCTCAGTTTACTAGTGCCATTTGTTCAGTGGTTCGTA 810       820       830       840       850
GGGCTTTCCCCCACTGTTTGGCTTTCAGTTATATGGATGATGTGGTATTG 860       870       880       890       900
GGGGCCAAGTCTGTACAACATCTTGAATCCCTTTTTACCGCTGTTACCAA 910       920       930       940       950
TTTTCTTTTGTCTTTGGGTATACATTTAAACCCTRCTAAAACCAAACGTT 960       970       980       990      1000
GGGGTTACTCCCTTAACTTCATGGGATATGTAATTGGAAGTTGGGGTACC 1010      1020      1030
TTACCACAGGAACATATTGTACACAAAATCAAACA
```

Figure 34 continued

Figure 35 Patient K HBV pol

```
           10         20         30         40         50
   SSCLHQSAVRKTAYTHLSTSKRQSSSGHAVELQHIPPSSARSQSEGPILS 60         70         80         90        100
   CWWLQFRNSKPCSDYCLSHIVNLLEDWGPCTEYGEHHIRIPRTPARVTGG 110        120        130        140        150
   VFLVDKNPHNTTESRLVVDFSQFSRGSTHVSWPKFAVPNLQSLTNLLSSN 160        170        180        190        200
   LSWLSLDVSAAFYHLPLHPAAMPHLLVGSSGLPRYVARLSSTSRNINYQH 210        220        230        240        250
   GTMQDLHDSCSRNLYVSLLLLYKTFGRKLHLYSHPIILGFRKIPMGVGLS 260        270        280        290        300
   PFLLAQFTSAICSVVRRAFPHCLAFSYMDDVVLGAKSVQHLESLFTAVTN 310        320        330        340
   FLLSLGIHLNPXKTKRWGYSLNFMGYVIGSWGTLPQEHIVHKIK
```

Figure 35

Figure 36 Patient K HbsAg

```
         10         20         30         40         50
PPASTNRQSGRQPTPISPPLRDSHPQAMQWNSSTFHQALLDPRVRGLYFP 60         70         80         90        100
AGGSSSGTVNPVPTTASPISSIFSRTGDPAPNMESTTSGFLGPLLVLQAG 110        120        130        140        150
FFLLTRILTIPQSLDSWWTSLNFLGGAPTCPGQNLQSPTSNHSPTSCPPI 160        170        180        190        200
CPGYRWMCLRRFIIFLFILLLCLIFLLVLLDYQGMLPVCPLLPGTSTTST 210        220        230        240        250
GPCKTCTIPAQGTSMFPSCCCTKPSDGNCTCIPIPSSWAFARFLWEWASV 260        270        280        290        300
RFSWLSLLVPFVQWFVGLSPTVWLSVIWMMWYWGPSLYNILNPFLPLLPI 310        320        330        340
FFCLWVYI*TLLKPNVGVTPLTSWDM*LEVGVPYHRNILYTKSN
```

Figure 36

Figure 37 Patient L HBV nt

```
         10         20         30         40         50
CAGTCCGGAAGGCAGCCTACTCCCTTATCTCCACCTCTAAGGGACACTCA 60         70         80         90        100
TCCTCAGGCCATGCAGTGGAACTCCACCACTTTCCATCAAACTCTTCAAG 110        120        130        140        150
ATCCCAGAGTCAGGGCTCTGTACTTTCCTGCTGGTGGCTCCAGTTCAGGA 160        170        180        190        200
ACAGTGAGCCCTGCTCAGAATACTGCCTCTGCCATATCGTCAACCTTCTC 210        220        230        240        250
GAAGACTGGGGACCCTGTACCGAACATGGAGAACATCGCATCAGGACTCC 260        270        280        290        300
TAGGACCCCTGCTCGCGTTACAGGCGGGGTTTTTCTCGTTGACAAAAATC 310        320        330        340        350
CTCACAATACCACAGAGTCTAGACTCGTGGTGGACTTCTCTCAATTTTCT 360        370        380        390        400
AGGGGGAACACCCGTGTGTCTTGGCCAAAATTCGCAGTCCCAAATCTCCA 410        420        430        440        450
GTCACTCACCAACTTGTTGTCCTCCAATTTGTCCTGGTTATCGCTGGATG 460        470        480        490        500
TGTCTGCGGCGTTTTATCATCTTCCTCTGCATCCTGCTGCTATGCCTCAT 510        520        530        540        550
CTTCTTGTTGGTTCTTCTGGACTATCAAGGTATGTTGCCCGTTTGTCCTC 560        570        580        590        600
TAATTCCAGGATCATCAACCACCAGCACCGGACCATGCAGAACCTGCACG 610        620        630        640        650
ACTCCTGCTCAAGGAACCTCTATGTTTCCCTCATGTTGCTGTACAAAACC
```

Figure 37

```
          660       670       680       690       700
TACGGACGGAAACTGCACCTGTATTCCCATCCCATCATCTTGGGCTTTCG 710       720       730       740       750
CAAAATACCTATGGGAGTGGGCCTCAGTCCGTTTCTCTTGGCTCAGTTTA 760       770       780       790       800
CTAGTGCCGTTTGTTCAGTGGTTCGTAGGGCTTTCCCCCACTGTCTGGCT 810       820       830       840       850
TTCAGTTATATGGATGATGTGGTATTGGGGGCCAAGTCTGTACAACATCT 860       870       880       890       900
TGAGTCCCTTTATGCCGCTGTTACCAATTTTCTTTTGTCTTTGGGTATAC 910       920       930       940       950
ATTTAAACCCTCACAAAACAAAAAGATGGGGATATTCCCTTCAATTCATG 960       970       980
GGATATGTAATTGGGGGTTGGGGCTCCTTG
```

Figure 37 continued

Figure 38. Patient L Pol

```
          10        20        30        40        50
EDWGPCTEHGEHRIRTPRTPARVTGGVFLVDKNPHNTTESRLVVDFSQFS 60        70        80        90       100
RGNTRVSWPKFAVPNLQSLTNLLSSNLSWLSLDVSAAFYHLPLHPAAMPH 110       120       130       140       150
LLVGSSGLSRYVARLSSNSRIINHQHRTMQNLHDSCSRNLYVSLMLLYKT 160       170       180       190       200
YGRKLHLYSHPIILGFRKIPMGVGLSPFLLAQFTSAVCSVVRRAFPHCLA 210       220       230       240       250
FSYMDDVVLGAKSVQHLESLYAAVTNFLLSLGIHLNPHKTKRWGYSLQFM

GYVIGGWG
```

Figure 38

Figure 39 Patient L HBsAg

```
         10        20        30        40        50
MENIASGLLGPLLALQAGFFSLTKILTIPQSLDSWWTSLNFLGGTPVCLG 60        70        80        90       100
QNSQSQISSHSPTCCPPICPGYRWMCLRRFIIFLCILLLCLIFLLVLLDY 110       120       130       140       150
QGMLPVCPLIPGSSTTSTGPCRTCTTPAQGTSMFPSCCCTKPTDGNCTCI 160       170       180       190       200
PIPSSWAFAKYLWEWASVRFSWLSLLVPFVQWFVGLSPTVWLSVIWMMWY 210       220
WGPSLYNILSPFMPLLPIFFCLWVYI
```

Figure 39

```
        10        20        30        40        50
CCTGCTGGTGGCTCCAGTTCAGGAACAGTAAACCCTGTTCCGACTACTGC 60        70        80        90       100
CTCTCCCTTATCGTCAATCTTCTCGAGGATTGGGGACCCTGCGCTGAACA 110       120       130       140       150
TGGAGAACATCACATCAGGATTCCTAGGACCCCTTCTCGTGTTACAGGCG 160       170       180       190       200
GGGTTTTCTTGTTGACAAGAATCCTCACAATACCGCAGAGTCTAGACTC 210       220       230       240       250
GTGGTGGACTTCTCTCAATTTTCGAGGGGGAACTACCGTGTGTCTTGGCC 260       270       280       290       300
AAAATTCGCAGTCCCCAACCTCCAATCACTCACCAACCTCCTGTCCTCCA 310       320       330       340       350
ACTTGTCCTGGTTATCGCTGGATGTGTCTGCGGCGTTTTATCATMTTCCT 360       370       380       390       400
CTTCATCCTGCTGCTATGCCTCATCTTCTTGTTGGTTCTTCTGGACTATC 410       420       430       440       450
RAGGTATGTTGCCCGTTTGTCCTCTAATTCCAGGATCCTCAWCCACCAGC 460       470       480       490       500
ACGGGACCATGCCGAACCTGCATGACTACTGCTCAAGGAACCTCTATGTA 510       520       530       540       550
TCCCTCCTGTTGCTGTACCAAACCTACGGACGGAAATTGCACCTGTATTC 560       570       580       590       600
CCATCCCATCATCCTGGGCTTTCGGAAAATTCCTATGGGAGTGGGCCTCA 610       620       630       640       650
GCCCGTTTCTCCTGGCTCAGTTTACTAGTGCCATTTGTTCAGTGGTTCGT 660       670       680       690       700
AGGGCTTTCCCCCACTGTTTGGCTTTCAGTTATATGGATGATGTGGTATT 710       720       730       740       750
GGGGGCCAAGTCTGTAYMGCATCTTGAGTCCCTTTTTACCGCTGTTACCA 760       770       780       790       800
ATTTTCTTTTGTCTTTGGGTATACATTTAAACCCTAACAAAACAAAGAGA 810       820       830       840       850
TGGGGTTACTCTCTGAATTTTATGGGTTATGTCATTGGAAGTTATGGGTC 860       870       880       890       900
CTTGCCACAAGAACACATCATACAAAAAATCAAAGAATGTTTTAGAAAAC
T
```

Figure 40

```
        10         20         30         40         50
CWWLQFRNSKPCSDYCLSLIVNLLEDWGPCAEHGEHHIRIPRTPSRVTGG 60         70         80         90        100
VFLVDKNPHNTAESRLVVDFSQFSRGNYRVSWPKFAVPNLQSLTNLLSSN 110        120        130        140        150
LSWLSLDVSAAFYHXPLHPAAMPHLLVGSSGLSRYVARLSSNSRILXHQH 160        170        180        190        200
GTMPNLHDYCSRNLYVSLLLLYQTYGRKLHLYSHPIILGFRKIPMGVGLS 210        220        230        240        250
PFLLAQFTSAICSVVRRAFPHCLAFSYMDDVVLGAKSVXHLESLFTAVTN 260        270        280        290
FLLSLGIHLNPNKTKRWGYSLNFMGYVIGSYGSLPQEHIIQKIKECFRK
```

Figure 41

```
        10         20         30         40         50
PAGGSSSGTVNPVPTTASPLSSIFSRIGDPALNMENITSGFLGPLLVLQA 60         70         80         90        100
GFFLLTRILTIPQSLDSWWTSLNFRGGTTVCLGQNSQSPTSNHSPTSCPP 110        120        130        140        150
TCPGYRWMCLRRFIIFLFILLLCLIFLLVLLDYXGMLPVCPLIPGSSXTS 160        170        180        190        200
TGPCRTCMTTAQGTSMYPSCCCTKPTDGNCTCIPIPSSWAFGKFLWEWAS 210        220        230        240        250
ARFSWLSLLVPFVQWFVGLSPTVWLSVIWMMWYWGPSLYXILSPFLPLLP

260
IFFCLWVYI*
```

Figure 42

```
        10         20         30         40         50
CTTTCACCAAACTCTGCAAGATCCCCCTGCTGGTGGCTCCAGTTCAGGAA 60         70         80         90        100
CAGTAAACCCTGTTCCGACTACTGCCTCTCCCTTATCGTCAATCTTCTCG 110        120        130        140        150
AGGATTGGGGACCCTGCGCGGAACATGGAGAACATCACATCAGGATTCCT 160        170        180        190        200
AGGACCCCTTCTCGTGTTACAGGCGGGGTTTTCTTGTTGACAAGAATCC 210        220        230        240        250
TCACAATACCGCAGAGTCTAGACTCGTGGTGGACTTCTCTCAATTTTCTA 260        270        280        290        300
GGGGGAACTACCGTGTGTCTTGGCCAAAATTCGCAGTCCCCAACCTCCAA 310        320        330        340        350
TCACTCACCAACCTCCTGTCCTCCAACTTGTCCTGGTTATCGCTGGATGT 360        370        380        390        400
GTCTGCGGCGTTTTATCATCTTCCTCTTCATCCTGCTGCTATGCCTCATC 410        420        430        440        450
TTCTTGTTGGTTCTTCTGGACTATCRAGGTATGTTGCCCGTTTGTCCTCT 460        470        480        490        500
AATTCCAGGATCCTCAACCACCAGCACGGGACCATGCCGAACCTGCATGA 510        520        530        540        550
CTACTGCTCAAGGAACCTCTATGTATCCCTCCTGTTGCTGTACCAAACCT 560        570        580        590        600
ACGGACGGAAATTGCACCTGTATTCCCATCCCATCATCCTGGGCTTTCGG 610        620        630        640        650
AAAATTCCTATGGGAGTGGGCCTCAGCCCGTTTCTCCTGGCTCAGTTTAC 660        670        680        690        700
TAGTGCCATTTGTTCAGTGGTTCGTAGGGCTTTCCCCCACTGTTTGGCTT 710        720        730        740        750
TCAGTTATATGGATGATGTGGTATTGGGGGCCAAGTCTGYACAGCATCTT 760        770        780        790        800
GAGTCCCTTTTTACCGCGGTGACCAATTTTCTTTTGTCTTTGGGTATACA 810        820        830        840        850
TTTAAACCCTAACAAAACAAAGAGATGGGGTTACTCTCTGAATTTTATGG 860        870        880        890        900
GTTATGTCATTGGAAGTTATGGGTCCTTGCCACAAGAACACATCATACAA

910
AAAATCAAAGAA
```

Figure 43

```
        10         20         30         40         50
LSPNSARSPCWWLQFRNSKPCSDYCLSLIVNLLEDWGPCAEHGEHHIRIP 60         70         80         90        100
RTPSRVTGGVFLVDKNPHNTAESRLVVDFSQFSRGNYRVSWPKFAVPNLQ 110        120        130        140        150
SLTNLLSSNLSWLSLDVSAAFYHLPLHPAAMPHLLVGSSGLSRYVARLSS 160        170        180        190        200
NSRILNHQHGTMPNLHDYCSRNLYVSLLLLYQTYGRKLHLYSHPIILGFR 210        220        230        240        250
KIPMGVGLSPFLLAQFTSAICSVVRRAFPHCLAFSYMDDVVLGAKSXQHL 260        270        280        290        300
ESLFTAVTNFLLSLGIHLNPNKTKRWGYSLNFMGYVIGSYGSLPQEHIIQ

KIKE
```

Figure 44

```
        10         20         30         40         50
FHQTLQDPPAGGSSSGTVNPVPTTASPLSSIFSRIGDPARNMENITSGFL 60         70         80         90        100
GPLLVLQAGFFLLTRILTIPQSLDSWWTSLNFLGGTTVCLGQNSQSPTSN 110        120        130        140        150
HSPTSCPPTCPGYRWMCLRRFIIFLFILLLCLIFLLVLLDYXGMLPVCPL 160        170        180        190        200
IPGSSTTSTGPCRTCMTTAQGTSMYPSCCCTKPTDGNCTCIPIPSSWAFG 210        220        230        240        250
KFLWEWASARFSWLSLLVPFVQWFVGLSPTVWLSVIWMMWYWGPSLXSIL

260
SPFLPR*PIFFCLWVYI*
```

Figure 45

VIRAL VARIANTS DETECTION AND APPLICATION

CROSS-REFERENCE TO RELATED APPLICATIONS

This application is a continuation of U.S. application Ser. No. 10/576,906, filed on Feb. 14, 2007, which is the §371 national phase of PCT/AU04/01440 having an international filing date of Oct. 20, 2004.

BACKGROUND OF THE INVENTION

1. Field of the Invention

The present invention relates generally to viral variants exhibiting reduced sensitivity to particular agents and/or reduced interactivity with immunological reagents. More particularly, the present invention is directed to hepatitis B virus (HBV) variants exhibiting complete or partial resistance to nucleoside or nucleotide analogs and/or reduced interactivity with antibodies to viral surface components including reduced sensitivity to these antibodies. The present invention further contemplates assays for detecting such viral variants, which assays are useful in monitoring anti-viral therapeutic regimens and in developing new or modified vaccines directed against viral agents and in particular HBV variants. The present invention also contemplates the use of the viral variants to screen for and/or develop or design agents capable of inhibiting infection, replication and/or release of the virus.

2. Description of the Prior Art

Bibliographic details of the publications referred to in this specification are also collected at the end of the description.

The reference to any prior art in this specification is not, and should not be taken as, an acknowledgment or any form of suggestion that that prior art forms part of the common general knowledge in any country.

Hepatitis B virus (HBV) can cause debilitating disease conditions and can lead to acute liver failure. HBV is a DNA virus which replicates via an RNA intermediate and utilizes reverse transcription in its replication strategy (Summers and Mason, *Cell* 29: 403-415, 1982). The HBV genome is of a complex nature having a partially double-stranded DNA structure with overlapping open reading frames encoding surface, core, polymerase and X genes. The complex nature of the HBV genome is represented in FIG. 1. The polymerase consists of four functional regions, the terminal protein (TP), spacer, reverse transcriptase (rt) and ribonuclease (RNAse).

The polymerase gene of HBV overlaps the envelope gene, mutations in the catalytic domain of the polymerase gene can also affect the nucleotide and the deduced amino acid sequence of the envelope protein and vice versa. In particular, the genetic sequence for the neutralization domain of HBV known as the 'a' determinant, which is found within the HBsAg and located between amino acids 99 and 169, actually overlaps the major catalytic regions of the viral polymerase protein and in particular domains A and B.

The presence of an HBV DNA polymerase has led to the proposition that nucleoside or nucleotide analogs could act as effective anti-viral agents. Examples of nucleoside or nucleotide analogs currently being tested are penciclovir and its oral form (FCV) [Vere Hodge, *Antiviral Chem Chemother* 4: 67-84, 1993; Boyd et al., *Antiviral Chem. Chemother.* 32: 358-363, 1987; Kruger et al., *Hepatology* 22: 219A, 1994; Main et al., *J. Viral Hepatitis* 3: 211-215, 1996], Lamivudine [(-)-β-2'-deoxy-3'-thiacytidine]; (3TC or LMV) [Severini et al., *Antimicrobial Agents Chemother.* 39: 430-435, 1995; Dienstag et al., *New England J Med* 333: 1657-1661, 1995].

New nucleoside or nucleotide analogs which have already progressed to clinical trials include the pyrimidines Emtricitabine, ((-)-β-L-2'-3'-dideoxy-5-fluoro-3'-thiacydidine; FTC), the 5-fluoro derivative of 3TC, and Clevudine (1-(2-fluoro-5-methyl-β-L-arabino-furanosyl) uracil; L-FMAU), a thymidine analog. Like 3TC, these are pyrimidine derivatives with an unnatural "L"-configuration. Several purine derivatives have also progressed to clinical trials; they include Entecavir (BMS-200, 475; ETV), a carbocyclic deoxyguanosine analog, diaminopurine dioxolane (DAPD), an oral pro-drug for dioxolane guanine ((-)-β-D-2-aminopurine dioxolane; DXG) and Adefovir dipivoxil, an oral prodrug for the acyclic deoxyadenosine monophosphate nucleoside or nucleotide analog Adefovir (9-[phosphonyl-methoxyethyl]-adenine; PMEA). Other drugs in pre-clinical and clinical trials include FLG [Medivir], ACH-126,443 (L-d4C) [Archillion Pharmaceuticals], ICN 2001-3 (ICN) and Racivir (RCV) [Pharmassett].

Whilst these agents are highly effective in inhibiting HBV DNA synthesis, there is the potential for resistant mutants of HBV to emerge during long term antiviral chemotherapy. In patients on prolonged LMV therapy, key resistance mutations are selected in the rt domain within the polymerase at rtM204I/V+/−rtL180M as well as other mutations. The nomenclature used for the polymerase mutations is in accordance with that proposed by Stuyver et al., 2001, supra. LMV is a nucleoside or a nucleotide analog that has been approved for use against chronic HBV infection. LMV is a particularly potent inhibitor of HBV replication and reduces HBV DNA titres in the sera of chronically infected patients after orthotopic liver transplantation (OLT) by inhibiting viral DNA synthesis. LMV monotherapy seems unlikely to be able to control HBV replication in the longer term. This is because emergence of LMV-resistant strains of HBV seems almost inevitable during monotherapy.

Adefovir dipivoxil (ADV: formerly, bis-pom PMEA) is an orally available prodrug of the acyclic deoxyadenosine monophosphate analog adefovir (formerly, PMEA) (FIG. 2). ADV is also a potent inhibitor of HBV replication and has recently been given FDA approval for use against chronic HBV infection. Adefovir dipivoxil differs from other agents in this class in that it is a nucleotide (vs. nucleoside) analog and as such bypasses the first phosphorylation reaction during drug activation. This step is often rate-limiting. Adefovir dipivoxil has demonstrated clinical activity against both wild-type and lamivudine-resistant strains of HBV and is currently in phase III clinical Testing (Gilson et al., *J Viral Hepat* 6: 387-395, 1999; Perrillo et al., *Hepatology* 32: 129-134, 2000; Peters et al., *Transplantation* 68: 1912-1914, 1999; Benhamou et al., *Lancet* 358: 718-723, 2001). During phase II studies a 30 mg daily dose of adefovir dipivoxil resulted in a mean 4 $\log_{10}$ decrease in viremia over 12 weeks (Heathcote et al., *Hepatology* 28: A620, 1998). ADV is a substituted acyclic nucleoside phosphonate. This class of compounds also includes tenofovir disoproxil fumarate (also referred to as tenofovir DF, or tenofovir, or (TFV) or 9-R-(2-phosphonomethoxypropyl)adenine (PMPA) and is marketed as Viread by Gilead sciences).

TFV has antiviral activity against both HBV and HIV (Ying et al., *J Viral Hepat.* 7(2): 161-165, 2000; Ying et al., *J. Viral Hepat.* 7(1): 79-83, 2000; Suo et al., *J Biol Chem.* 273(42): 27250-27258. 1998).

FTC has activity against HBV and HIV (Frick et al., *Antimicrob Agents Chemother* 37: 2285-2292, 1993).

Nucleoside or nucleotide analog therapy may be administered as monotherapy or combination therapy where two or more nucleoside or nucleotide analogs may be administered.

The nucleoside or nucleotide analogs may also be administered in combination with other antiviral agents such as interferon or hepatitis B immunoglobulin (HBIG).

There is a need to monitor for the emergence of nucleoside/nucleotide-analog- or antibody-resistant strains of HBV and to develop diagnostic protocols to detect these resistant viruses and/or to use them to screen for and/or develop or design agents having properties making them useful as antiviral agents. Defective forms of these resistant strains or antigenic components therefrom are also proposed to be useful in the development of therapeutic vaccine compositions as are antibodies directed to viral surface components.

SUMMARY OF THE INVENTION

Throughout this specification, unless the context requires otherwise, the word "comprise", or variations such as "comprises" or "comprising", will be understood to imply the inclusion of a stated element or integer or group of elements or integers but not the exclusion of any other element or integer or group of elements or integers.

Nucleotide and amino acid sequences are referred to by a sequence identifier number (SEQ ID NO:). The SEQ ID NOs: correspond numerically to the sequence identifiers <400>1 (SEQ ID NO:1), <400>2 (SEQ ID NO:2), etc. A summary of the sequence identifiers is provided in Table 1. A sequence listing is provided after the claims.

Specific mutations in an amino acid sequence are represented herein as "$Xaa_1 nXaa_2$" where $Xaa_1$ is the original amino acid residue before mutation, n is the residue number and $Xaa_2$ is the mutant amino acid. The abbreviation "Xaa" may be the three letter or single letter (i.e. "X") code. An "rt" before "$Xaa_1 nXaa_2$" means "reverse transcriptase". An "s" means an envelope gene. The amino acid residues for HBV DNA polymerase are numbered with the residue methionine in the motif Tyr Met Asp Asp (YMDD) being residue number 204 (Stuyver et al., *Hepatology* 33: 751-757, 2001). The amino acid residues for hepatitis B virus surface antigen are number according to Norder et al. (*J. Gen. Virol.* 74: 341-1348, 1993). Both single and three letter abbreviations are used to define amino acid residues and these are summarized in Table 2.

In accordance with the present invention, the selection of HBV variants is identified in patients (Patients A to L) with chronic HBV infection treated with ADV. Patient E is a non-responder to ADV. Other variants of HBV are identified during a combination ADV and LMV treatment or a combination of TFV and LMV treatment (eg. Patient M) or a combination of TFV and FTC or treatment with TFV alone with mutations in the HBV DNA polymerase gene which reduce the sensitivity of HBV to nucleoside or nucleotide analogs. Consequently, HBV rt variants are contemplated which are resistant to, or which exhibit reduced sensitivity to, ADV, LMV, TFV or FTC; ADV and LMV; ADV and TFV; LMV and TFV; FTC and ADV; FTC and TFV; FTC and LMV; ADV and LMV and TFV; or ADV and FTC and TFV, TFV and FTC and LMV; ADV and LMV and FTC; and/or ADV and FTC and LMV and TFV and/or optionally other nucleoside or nucleotide analogs or other anti-HBV agents or combinations thereof. Corresponding mutations in the surface antigen also occur. The identification of these HBV variants is important for the development of assays to monitor ADV, LMV, FTC and/or TFV resistance and/or resistance to other nucleoside or nucleotide analogs or other anti-HBV agents or combinations thereof and to screen for agents which are useful as alternative therapeutic agents.

Reference herein to "anti-HBV agents" includes nucleoside and nucleotide analogs as well as immunological reagents (e.g. antibodies to HBV surface components) and chemical, proteinaceous and nucleic acid agents which inhibit or otherwise interfere with viral replication, maintenance, infection, assembly or release.

The detection of such HBV variants is particularly important in the management of therapeutic protocols including the selection of appropriate agents for treating HBV infection. The method of this aspect of the present invention is predicated in part on monitoring the development in a subject of an increased HBV load in the presence of a nucleoside or nucleotide analog or other anti-HBV agents or combinations thereof. The clinician is then able to modify an existing treatment protocol or select an appropriate treatment protocol accordingly.

Accordingly, one aspect of the present invention is directed to an isolated Hepatitis B virus (HBV) variant wherein said variant comprises a nucleotide mutation in a gene encoding a DNA polymerase resulting in at least one amino acid addition, substitution and/or deletion to said DNA polymerase and wherein said variant exhibits decreased sensitivity to one or more nucleoside or nucleotide analogs selected from the list consisting of ADV, LMV, TFV or FTC; ADV and LMV; ADV and TFV; LMV and TFV; FTC and ADV; FTC and TFV; FTC and LMV; ADV and LMV and TFV; ADV and FTC and TFV; TFV and FTC and LMV; ADV and LMV and FTC; ADV and FTC and LMV and TFV, and other nucleoside or nucleotide analogs, and/or anti-HBV agents. The variant HBV comprises a mutation in an overlapping open reading frame in its genome in a region defined by one or more of domains F and G and domain A through to E of HBV DNA polymerase.

Another aspect of the present invention provides an isolated HBV variant comprising a nucleotide mutation in the S gene resulting in at least one amino acid addition, substitution and/or deletion to the surface antigen and which exhibits decreased sensitivity to one or more nucleoside or nucleotide analogs selected from the list consisting of ADV, LMV, TFV or FTC; ADV and LMV; ADV and TFV; LMV and TFV; FTC and ADV; FTC and TFV; FTC and LMV; ADV and LMV and TFV; or ADV and FTC and TFV; TFV and FTC and LMV; ADV and LMV and FTC; and/or ADV and FTC and LMV and TFV and other nucleoside or nucleotide analogs and/or anti-HBV agents.

Useful mutants in the rt region include, in one embodiment, rtT38K, rtR55H and rtA181V; in another embodiment include rtS/T78S, rtV80L, rtN/S118N, rtN/K139K, rtE142V, rtA/T181A rtI204M, rtQ/P/S/Stop215S, rtE/K218E, rtN/H238H and rtY245H; in yet another embodiment include rtN238T; and yet another embodiment include rtI122V and rtA181T; in yet another embodiment include rtL180M, rtA/V200V, rtM204V, rtV214A, rtH237H/P, rtV253G, in yet another embodiment include rtT128N and rtN236T, in yet another embodiment include tL180M, rtM204V rtQ215S, in yet another embodiment include rtT128S rtL180M, rtM204V and rtQ215S, in yet another embodiment include rtI80L, rtI204M, rtN238T, in yet another embodiment include rtN238T/A, in yet another embodiment include rtI187V, in yet another embodiment include rtN123N/I rtS135Y, rtV214A/V and rtQ215Q/P/Stop/S, or a combination thereof or an equivalent mutation.

Other HBV variants are also contemplated with mutations rtT38K (in the F domain of the DNA polymerase), rtR55H (located between the F and A domains), rtS/T78S, rtV80L (these are located within the A domain), rtN/S118N, rtI122V, rtN123N/I, rtS135Y, rtN/K139K, rtE142V (located between the A and B domains, rtA181V, rtA181T (these are located in the B domain), rtI187V (located between the B and C domains), rtA/V200V (Located in the C Domain), rtV214A, rtV214A/V and rtQ215Q/P/Stop/S, rtQ/P/S/Stop215S, rtQ215S, rt E/K218E (located between the C and P domains), rtn236T, rtH237H/P rtN/H238H, rtN238T, rtN238T/A (these are located in the D domain), rtY245H (located between the D and E domains), and rtV253G (located in the E Domain) or a combination thereof or an equivalent mutation.

Useful mutations in the S gene include, in one embodiment include sQ30K. sE44G, sA47T, sI126T, sA159V and sL173F, in another embodiment include sF555S, sC/Stop69C, sC/Y76Y, sI/V110I, sN/T131N, sN134Y, sStop/W172W, sStop/W196W, sS/R207R; in yet another embodiment include sV14A, sL95W, sV96G, and sI208T/I; and in yet another embodiment include sT47A and sW172stop, and in yet another embodiment include PreS2 T6S, sT47A, sP62L, sL/F192F, sI195M, and in yet another embodiment include sS53L, and in yet another embodiment include sP120T, and in yet another embodiment include sN40S, sS207R, and in yet another embodiment include sQ101R, sI195M, sS207R, and in yet another embodiment include sL95W and sL196W, and in yet another embodiment include sV14A, in yet another embodiment include sL42R, sQ102Q/R, sT115T/S, sS207S/R, sL215R and sL216Stop, or a combination thereof or an equivalent mutation.

The present invention further contemplates a method for determining the potential for an HBV to exhibit reduced sensitivity to ADV, LMV, TFV or FTC; ADV and LMV; ADV and TFV; LMV and TFV; FTC and ADV; FTC and TFV; FTC and LMV; ADV and LMV and TFV; or ADV and FTC and TFV; TFV and FTC and LMV; ADV and LMV and FTC; and/or ADV and FTC and LMV and TFV and/or optionally other nucleoside or nucleotide analogs or other anti-HBV agents or combination thereof by isolating DNA or corresponding mRNA from the HBV and screening for a mutation in the nucleotide sequence encoding HBV DNA polymerase resulting in at least one amino acid substitution, deletion and/or addition in any one or more of domains F and G and domains A through to E or a region proximal thereto of the DNA polymerase and associated with resistance or decreased sensitivity to ADV, LMV, TFV or FTC; ADV and LMV; ADV and TFV; LMV and TFV; FTC and ADV; FTC and TFV; FTC and LMV; ADV and LMV and TFV; or ADV and FTC and TFV; TFV and FTC and LMV; ADV and LMV and FTC; and/or ADV and FTC and LMV and TFV and/or optionally other nucleoside or nucleotide analogs or other anti-HBV agents or combination thereof.

The presence of such a mutation is an indication of the likelihood of resistance to ADV, LMV, TFV or FTC; ADV and LMV; ADV and TFV; LMV and TFV; FTC and ADV; FTC and TFV; FTC and LMV; ADV and LMV and TFV; or ADV and FTC and TFV; TFV and FTC and LMV; ADV and LMV and FTC; and/or ADV and FTC and LMV and TFV and/or optionally other nucleoside or nucleotide analogs or other anti-HBV agents or combination thereof.

The present invention also provides a composition comprising a variant HBV resistant to ADV, LMV, TFV or FTC; ADV and LMV; ADV and TFV; LMV and TFV; FTC and ADV; FTC and TFV; FTC and LMV; ADV and LMV and TFV; or ADV and FTC and TFV; TFV and FTC and LMV; ADV and LMV and FTC; and/or ADV and FTC and LMV and TFV, ADV and LMV and FTC and/or optionally other nucleoside or nucleotide analogs or other anti-HBV agents or combination thereof or an HBV surface antigen from the variant HBV or a recombinant or derivative form thereof or its chemical equivalent and one or more pharmaceutically acceptable carriers and/or diluents.

Yet another aspect of the present invention provides a use of the aforementioned composition or a variant HBV comprising a nucleotide mutation in a gene encoding a DNA polymerase resulting in at least one amino acid addition, substitution and/or deletion to the DNA polymerase and a decreased sensitivity to ADV, LMV, TFV or FTC; ADV and LMV; ADV and TFV; LMV and TFV; FTC and ADV; FTC and TFV; FTC and LMV; ADV and LMV and TFV; or ADV and FTC and TFV; TFV and FTC and LMV; ADV and LMV and FTC; and/or ADV and FTC and LMV and TFV and/or optionally other nucleoside or nucleotide analogs or other anti-HBV agents or combination thereof in the manufacture of a medicament for the treatment and/or prophylaxis of hepatitis B virus infection.

The present invention also contemplates a method for determining whether an HBV strain exhibits reduced sensitivity to a nucleoside or nucleotide analog or other anti-HBV agents or by isolating DNA or corresponding mRNA from the HBV and screening for a mutation in the nucleotide sequence encoding the DNA polymerase wherein the presence of the following mutations in the rt region: in one embodiment, rtT38K, rtR55H and rtA181V; in another embodiment include rtS/T78S, rtV80L, rtN/S118N, rtN/K139K, rtE142V, rtA/T181A rtI204M, rtQ/P/S/Stop215S, rtE/K218E, rtN/H238H and rtY245H; in yet another embodiment include rtN238T; and yet another embodiment include rtI122V and rtA181T; in yet another embodiment include rtL180M, rtA/V200V, rtM204V, rtV214A, rtH237H/P, rtV253G, in yet another embodiment include rtT128N and rtN236T, in yet another embodiment include tL180M, rtM204V rtQ215S, in yet another embodiment includes rtT128S rtL180M, rtM204V and rtQ215S, in yet another embodiment includes rtI80L, rtI204M, rtN238T, in yet another embodiment include rtN238T/A, in yet another embodiment include rtI187V in yet another embodiment include rtN123N/I rtS135Y, rtV214A/V and rtQ215Q/P/Stop/S, or combinations thereof or an equivalent one or more other mutation is indicative of a variant which exhibits a decreased sensitivity to ADV, LMV, TFV or FTC; ADV and LMV; ADV and TFV; LMV and TFV; FTC and ADV; FTC and TFV; FTC and LMV; ADV and LMV and TFV; or ADV and FTC and TFV; TFV and FTC and LMV; ADV and LMV and FTC; and/or ADV and FTC and LMV and TFV and/or optionally other nucleoside or nucleotide analogs or other anti-HBV agents or combination thereof.

Still a further methodology comprises screening for a mutation in the nucleotide sequence encoding the envelope genes (s) wherein the presence of the following mutations in the s gene: in one embodiment include sQ30K. sE44G, sA47T, sI126T, sA159V and sL173F, in another embodiment include sF55S, sC/Stop69C, sC/Y76Y, sI/V110I, sN/T131N, sN134Y, sStop/W172W, sStop/W196W, sS/R207R; in yet another embodiment include sV14A, sL95W, sV96G, and sI208T/I; and in yet another embodiment include sT47A and sW172stop, and in yet another embodiment include PreS2 T6S, sT47A, sP62L, sL/F192F, sI195M, and in yet another embodiment include sS53L, and in yet another embodiment include sP120T, and in yet another embodiment include sN40S, sS207R, and in yet another embodiment include sQ101R, sI195M, sS207R, and in yet another embodiment include sL95W and sL196W, and in yet another embodiment include sV14A, in yet another embodiment include sL42R, sQ102Q/R, sT115T/S, sS207S/R, sL215R and sL216Stop or combinations thereof or an equivalent one or more other mutation is indicative of a variant which exhibits a decreased sensitivity to ADV, LMV, TFV or FTC; ADV and LMV; ADV and TFV; LMV and TFV; FTC and ADV; FTC and TFV; FTC and LMV; ADV and LMV and TFV; or ADV and FTC and TFV; TFV and FTC and LMV; ADV and LMV and FTC; and/or ADV and FTC and LMV and TFV, and/or optionally other nucleoside or nucleotide analogs or other anti-HBV agents or combination thereof.

Preferably, the variants are in an isolated form such that they have undergone at least one purification step away from naturally occurring body fluid. Alternatively, the variants may be maintained in isolated body fluid or may be in DNA form. The present invention also contemplates infectious molecular clones comprising the genome or parts thereof from a variant HBV. The detection of HBV or its components in cells, cell lysates, cultured supernatant fluid and bodily fluid may be by any convenient means including any nucleic acid-based detection means, for example, by nucleic acid hybridization techniques or via one or more polymerase chain reactions (PCRs). The term "bodily fluid" includes any fluid derived from the blood, lymph, tissue or organ systems including serum, whole blood, biopsy and biopsy fluid, organ explants and organ suspension such as liver suspensions.

Another aspect of the present invention is directed to a variant HBV comprising a surface antigen having an amino acid sequence with a single or multiple amino acid substitution, addition and/or deletion or a truncation compared to a surface antigen from a reference or wild type HBV and wherein an antibody generated to the reference or wild type surface antigen exhibits an altered immunological profile relative to the HBV variant. One altered profile includes a reduced capacity for neutralizing the HBV. More particularly, the surface antigen of the variant HBV exhibits an altered immunological profile compared to a pre-treatment HBV where the variant HBV is selected for by a nucleoside or nucleotide analog or other anti-HBV agents of the HBV DNA polymerase. The variant HBV of this aspect of the invention may also comprise a nucleotide sequence comprising a single or multiple nucleotide substitution, addition and/or deletion compared to a pre-treatment HBV.

The present invention further contemplates a method for detecting a variant HBV exhibiting an altered immunological profile said method comprising isolating an HBV from a subject exposed to a nucleoside or nucleotide analog or combination of analogs selected from the listed consisting of ADV, LMV, TFV or FTC; ADV and LMV; ADV and TFV; LMV and TFV; FTC and ADV; FTC and TFV; FTC and LMV; ADV and LMV and TFV; ADV and FTC and TFV; TFV and FTC and LMV; ADV and LMV and FTC; ADV and FTC and LMV and TFV, and then contacting said HBV with a panel of one or more antibodies to a surface antigen and screening for any change in binding affinity or binding spectrum.

In a related invention, the present invention provides a method for detecting a variant HBV exhibiting an altered immunological profile said method comprising isolating a serum sample from a subject exposed to a nucleoside or nucleotide analog selected from the listed consisting of ADV, LMV, TFV or FTC; ADV and LMV; ADV and TFV; LMV and TFV; FTC and ADV; FTC and TFV; FTC and LMV; ADV and LMV and TFV; ADV and FTC and TFV; TFV and FTC and LMV; ADV and LMV and FTC; ADV and FTC and LMV and TFV, and then contacting the serum with a panel of HBV surface antigens or antibody-binding fragments thereof and screening for any change in binding affinity or binding spectrum.

The present invention extends to an isolated HBsAg or a recombinant form thereof or derivative or chemical equivalent thereof corresponding to the variant HBV. Generally, the HBsAg or its recombinant or derivative form or its chemical equivalent comprises an amino acid sequence with a single or multiple amino acid substitution, addition and/or deletion or a truncation compared to an HBsAg from a reference HBV and wherein an antibody directed to a reference HBV exhibits an altered immunological profile to an HBV carrying said variant HBsAg. In one embodiment, the altered immunological profile comprises a reduction in the ability to neutralize the variant HBV.

Another aspect of the present invention contemplates a method for detecting an agent which exhibits inhibitory activity to an HBV by generating a genetic construct comprising a replication competent-effective amount of the genome from the HBV contained in a plasmid vector and then transfecting said cells with said construct, contacting the cells, before, during and/or after transfection, with the agent to be tested, culturing the cells for a time and under conditions sufficient for the HBV to replicate, express genetic sequences and/or assemble and/or release virus or virus-like particles if resistant to said agents; and the subjecting the cells, cell lysates or culture supernatant fluid to viral- or viral-component-detection means to determine whether or not the virus has replicated, expressed genetic material and/or assembled and/or been released in the presence of the agent. In a preferred embodiment, the plasmid vector in a baculovirus vector and the method comprises generating a genetic construct comprising a replication competent-effective amount of the genome from the HBV contained in or fused to an amount of a baculovirus genome effective to infect cells and then infecting said cells with said construct, contacting the cells, before, during and/or after infection, with the agent to be tested, culturing the cells for a time and under conditions sufficient for the HBV to replicate, express genetic sequences and/or assemble and/or release virus or virus-like particles if resistant to said agent and then subjecting the cells, cell lysates or culture supernatant fluid to viral- or viral-component-detection means to determine whether or not the virus has replicated, expressed genetic material and/or assembled and/or been released in the presence of the agent.

In connection with these methods, the plasmid vector may include genes encoding part or all of other viral vectors such as baculovirus vectors or adenovirus vectors (see Ren and Nassal, *J. Virol.* 75(3): 1104-1116, 2001).

In an alternative embodiment, the method comprises generating a continuous cell line comprising an infectious copy of the genome of the HBV in a replication competent effective amount such that said infectious HBV genome is stably integrated into said continuous cell line such as but not limited to the 2.2.15 or AD cell line, contacting the cells with the agent to be tested, culturing the cells for a time and under conditions sufficient for the HBV to replicate, express genetic sequences and/or assemble and/or release virus or virus-like particles if resistant to the agent and then subjecting the cells, cell lysates or culture supernatant fluid to viral- or viral-component-detection means to determine whether or not the virus has replicated, expressed genetic material and/or assembled and/or been released in the presence of the agent.

In an alternative embodiment, the present invention also contemplates a method for detecting an agent which exhibits inhibitory activity to an HBV polymerase in an in vitro polymerase assay. The HBV polymerase activity can be examined using established assays (Gaillard et al., *Antimicrob Agents Chemother.* 46(4): 1005-1013, 2002; Xiong et al., *Hepatology.* 28(6): 1669-73, 1998). The HBV polymerase may be a wild-type or reference HBV polymerase or mutant HBV polymerase.

The identification of viral variants enables the production of vaccines comprising particular recombinant viral components such as polymerases or envelope genes PreS1, PreS2, S encoding for L, M, S proteins as well as therapeutic vaccines comprising defective HBV variants. Rational drug design may also be employed to identify or generate therapeutic molecules capable of interacting with a polymerase or envelope genes PreS1, PreS2, S encoding for L, M, S proteins or other component of the HBV. Such drugs may also have diagnostic potential. In addition, defective HBV variants may also be used as therapeutic compositions to generate an immune response against the same, similar or homologous viruses. Alternatively, antibodies generated to the HBV variants or surface components thereof may be used in passive immunization of subjects against infection by HBV variants or similar or homologous viruses. Furthermore, agents such as nucleoside or nucleotide analogs, RNAi or siRNA molecules (both DNA-derived or synthetic), antisense or sense oligonucleotides, chemical or proteinaceous molecules having an ability to down-regulate the activity of a component of HBV and inhibit replication, maintenance, infection, assembly or release are contemplated by the present invention.

A summary of the abbreviations used throughout the subject specification are provided in Table 3.

A summary of sequence identifiers used throughout the subject specification is provided in Table 1.

TABLE 1

Summary of sequence identifiers

| SEQUENCE ID NO: | DESCRIPTION |
|---|---|
| 1 | Formula I |
| 2 | Formula II |
| 3 | OS1 primer |
| 4 | TTA3 primer |
| 5 | JM primer |
| 6 | TTA4 primer |
| 7 | OS2 primer |
| 8 | sense primer |
| 9 | antisense primer |
| 10 | internal regions primer |
| 11 | internal regions primer |
| 12 | PC1 forward primer |
| 13 | PC2 reverse primer |
| 14 | HBV-specific molecular beacon primer |

TABLE 2

Single and three letter amino acid abbreviations

| Amino Acid | Three-letter Abbreviation | One-letter symbol |
|---|---|---|
| Alanine | Ala | A |
| Arginine | Arg | R |
| Asparagine | Asn | N |
| Aspartic acid | Asp | D |
| Cysteine | Cys | C |
| Glutamine | Gln | Q |
| Glutamic acid | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | The | T |
| Tryptophan | Trp | W |
| Tyrosine | Tyr | Y |
| Valine | Val | V |
| Any residue | Xaa | X |

TABLE 3

Abbreviations

| ABBREVIATION | DESCRIPTION |
|---|---|
| 3TC | (LMV); (−)-β-2′-deoxy-3′-thiacytidine |
| ADV | adefovir dipivoxil |
| DAPD | diaminopurine dioxalone |
| DXG | dioxolane guanine |
| ETV | entecavir |
| FAM | famciclovir |
| FCV | famciclovir |
| FTC | emtricitabine |
| HBIG | hepatitis B immunoglobulin |
| HBsAg | hepatitis B surface antigen |
| HBV | hepatitis B virus |
| LMV | lamividuine |
| PMEA | 9-[phosphonyl-methoxyethyl]-adenine; adefovir |
| PMPA | 9-R-(2-phosphonomethoxypropyl)adenine |
| RNase | ribonuclease |
| rt ("rt" before "Xaa$_1$nXaa$_2$" means reverse transcriptase) | reverse transcriptase |
| s (as used in a mutation, e.g. sF134V) | envelope gene |
| TFV | tenofovir disoproxil fumarate |
| YMDD | Tyr Met Asp Asp-a motif in the polymerase protein; where the Met residue is designated residue number 204 of the reverse transcriptase |

BRIEF DESCRIPTION OF THE FIGURES

FIG. 4 is a representation showing comparison of the HBV nucleotide sequence encoding the catalytic region of the polymerase gene in sequential samples from Patient A during ADV treatment.

FIG. 5 is a representation showing comparison of the deduced amino acid sequence of the catalytic region of the polymerase gene in sequential samples from Patient A during ADV therapy.

FIG. 6 is a representation showing comparison of the deduced amino acid sequence of the envelope gene in sequential samples from Patient A during ADV therapy.

FIG. 7 is a representation showing comparison of the HBV nucleotide sequence encoding the catalytic region of the polymerase gene in sequential samples from Patient B during ADV and LMV treatment.

FIG. 8 is a representation showing comparison of the deduced amino acid sequence of the catalytic region of the polymerase gene in sequential samples from Patient B during ADV and LMV therapy.

FIG. 9 is a representation showing comparison of the deduced amino acid sequence of the envelope gene in sequential samples from Patient B during ADV and LMV therapy.

FIG. 10 is a representation the HBV nucleotide sequence encoding the catalytic region of the polymerase gene in samples from Patient C during ADV treatment.

FIG. 11 is a representation the deduced amino acid sequence of the catalytic region of the polymerase gene in samples from Patient C during ADV therapy.

FIG. 12 is a representation the deduced amino acid sequence of the envelope gene in samples from Patient C during ADV therapy.

FIG. 13 is a representation showing the HBV nucleotide sequence encoding the catalytic region of the polymerase gene in samples from Patient D during ADV treatment.

FIG. 14 is a representation the deduced amino acid sequence of the catalytic region of the polymerase gene in sequential samples from Patient D during ADV therapy.

FIG. 15 is a representation showing comparison of the deduced amino acid sequence of the envelope gene in sequential samples from Patient D during ADV therapy.

FIG. 16 is a representation showing the HBV nucleotide sequence encoding the catalytic region of the polymerase gene in samples from Patient E during ADV treatment.

FIG. 17 is a representation showing the deduced amino acid sequence of the catalytic region of the polymerase gene in samples from Patient E during ADV therapy.

FIG. 18 is a representation showing the deduced amino acid sequence of the envelope gene in samples from Patient E during ADV therapy.

FIG. 19 is a representation showing the HBV nucleotide sequence encoding the catalytic region of the polymerase gene in samples from Patient F during ADV treatment.

FIG. 20 is a representation showing the deduced amino acid sequence of the catalytic region of the polymerase gene in samples from Patient F during ADV therapy.

FIG. 21 is a representation showing the deduced amino acid sequence of the envelope gene in samples from Patient F during ADV therapy.

FIG. 22 is a representation showing the HBV nucleotide sequence encoding the catalytic region of the polymerase gene in samples from Patient G during ADV treatment.

FIG. 23 is a representation showing the deduced amino acid sequence of the catalytic region of the polymerase gene in samples from Patient G during ADV therapy.

FIG. 24 is a representation showing the deduced amino acid sequence of the envelope gene in samples from Patient G during ADV therapy.

FIG. 25 is a representation showing the HBV nucleotide sequence encoding the catalytic region of the polymerase gene in samples from Patient H during ADV treatment.

FIG. 26 is a representation showing the deduced amino acid sequence of the catalytic region of the polymerase gene in samples from Patient H during ADV therapy.

FIG. 27 is a representation showing the deduced amino acid sequence of the envelope gene in samples from Patient H during ADV therapy.

FIG. 28 is a representation showing the HBV nucleotide sequence encoding the catalytic region of the polymerase gene in samples from Patient I during ADV treatment.

FIG. 29 is a representation showing the deduced amino acid sequence of the catalytic region of the polymerase gene in samples from Patient I during ADV therapy.

FIG. 30 is a representation showing the deduced amino acid sequence of the envelope gene in samples from Patient I during ADV therapy.

FIG. 31 is a representation showing the HBV nucleotide sequence encoding the catalytic region of the polymerase gene in samples from Patient J during ADV treatment.

FIG. 32 is a representation showing the deduced amino acid sequence of the catalytic region of the polymerase gene in samples from Patient J during ADV therapy.

FIG. 33 is a representation showing the deduced amino acid sequence of the envelope gene in samples from Patient J during ADV therapy.

FIG. 34 is a representation showing the HBV nucleotide sequence encoding the catalytic region of the polymerase gene in samples from Patient K during ADV treatment.

FIG. 35 is a representation showing the deduced amino acid sequence of the catalytic region of the polymerase gene in samples from Patient K during ADV therapy.

FIG. 36 is a representation showing the deduced amino acid sequence of the envelope gene in samples from Patient K during ADV therapy.

FIG. 37 is a representation showing the HBV nucleotide sequence encoding the catalytic region of the polymerase gene in samples from Patient L during ADV treatment.

FIG. 38 is a representation showing the deduced amino acid sequence of the catalytic region of the polymerase gene in samples from Patient L during ADV therapy.

FIG. 39 is a representation showing the deduced amino acid sequence of the envelope gene in samples from Patient L during ADV therapy.

FIG. 40 is a representation showing the HBV nucleotide sequence encoding the catalytic region of the polymerase gene in samples from Patient M during TFV treatment.

FIG. 41 is a representation showing the deduced amino acid sequence of the catalytic region of the polymerase gene in samples from Patient M during TFV therapy.

FIG. 42 is a representation showing the deduced amino acid sequence of the envelope gene in samples from Patient M during TFV therapy.

FIG. 43 is a representation showing the HBV nucleotide sequence encoding the catalytic region of the polymerase gene in another sample from Patient M during TFV treatment.

FIG. 44 is a representation showing the deduced amino acid sequence of the catalytic region of the polymerase gene in another sample from Patient M during TFV therapy.

FIG. 45 is a representation showing the deduced amino acid sequence of the envelope gene in another sample from Patient M during TFV therapy.

DETAILED DESCRIPTION OF THE PREFERRED EMBODIMENTS

Figure 1:
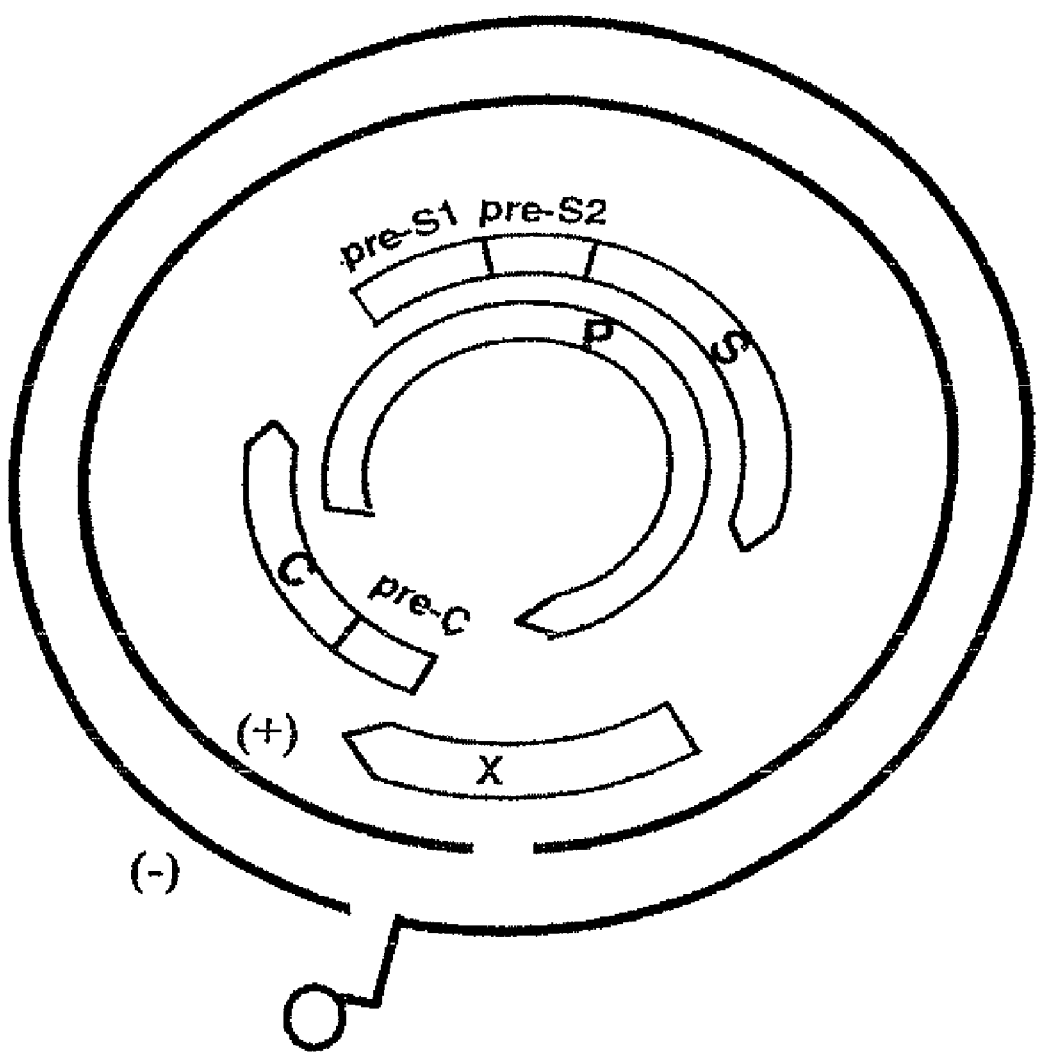
FIG. 1 is a diagrammatic representation showing the partially double stranded DNA HBV genome showing the overlapping open reading frames encoding surface (S), core (C), polymerase (P) and X gene.

The present invention is predicated in part on the identification and isolation of nucleoside or nucleotide analog-resistant variants of HBV following treatment of patients with either ADV or LMV or more particularly ADV and LMV or TFV and LMV, or optionally other nucleoside analogs or nucleotide analogs or other anti-HBV agents such as TFV or FTC. In particular, ADV or ADV and LMV treated patients gave rise to variants of HBV exhibiting decreased or reduced sensitivity to ADV, LMV, TFV or FTC; ADV and LMV; ADV and TFV; LMV and TFV; FTC and ADV; FTC and TFV; FTC and LMV; ADV and LMV and TFV; or ADV and FTC and TFV; TFV and FTC and LMV; ADV and LMV and FTC; and/or ADV and FTC and LMV and TFV. Reference herein to "decreased" or "reduced" in relation to sensitivity to ADV and/or LMV and/or FTC and/or TFV includes and encompasses a complete or substantial resistance to the nucleoside or nucleotide analog or other anti-HBV agents as well as partial resistance and includes a replication rate or replication efficiency which is more than a wild-type in the presence of a nucleoside or nucleotide analog or other anti-HBV agents. In one aspects this is conveniently measured by an increase in viral load during treatment, or alternatively, there is no substantial decrease in HBV DNA viral load from pretreatment HBV DNA levels during treatment (i.e., non-response to treatment).

Accordingly, one aspect of the present invention contemplates an isolated Hepatitis B virus (HBV) variant wherein said variant comprises a nucleotide mutation in a gene encoding a DNA polymerase resulting in at least one amino acid addition, substitution and/or deletion to said DNA polymerase and wherein said variant exhibits decreased sensitivity to one or more nucleoside or nucleotide analogs selected from the list consisting of ADV, LMV, TFV or FTC; ADV and LMV; ADV and TFV; LMV and TFV; FTC and ADV; FTC and TFV; FTC and LMV; ADV and LMV and TFV; ADV and FTC and TFV; TFV and FTC and LMV; ADV and LMV and FTC; ADV and FTC and LMV and TFV, and other nucleoside or nucleotide analogs, and/or anti-HBV agents.

Another aspect of the present invention provides a method for determining the potential for an HBV to exhibit reduced sensitivity to a nucleoside or nucleotide analog selected from ADV, LMV, TFV and FTC or a combination thereof or optionally other nucleoside or nucleotide analogs, said method comprising isolating DNA or corresponding mRNA from said HBV and screening for a mutation in the nucleotide sequence encoding HBV DNA polymerase resulting in at least one amino acid substitution, deletion and/or addition in any one or more of domains F and A through E or a region proximal thereto of said DNA polymerase and associated with resistance or decreases sensitivity to one or more of ADV, LMV, TFV and/or FTC wherein the presence of such a mutation is an indication of the likelihood of resistance to said one or more of ADV, LMV, TFV and/or FTC.

Before describing the present invention in detail, it is to be understood that unless otherwise indicated, the subject invention is not limited to specific formulations of components, manufacturing methods, dosage regimens, or the like, as such may vary. It is also to be understood that the terminology used herein is for the purpose of describing particular embodiments only and is not intended to be limiting.

It must be noted that, as used in the subject specification, the singular forms "a", "an" and "the" include plural aspects unless the context clearly dictates otherwise. Thus, for example, reference to "a nucleoside or nucleotide analog" includes a single analog, as well as two or more analogs; reference to "an HBV variant" includes reference to two or more HBV variants; and so forth.

In describing and claiming the present invention, the following terminology is used in accordance with the definitions set forth below.

The terms "analog", "compound", "active agent", "pharmacologically active agent", "medicament", "active" and "drug" are used interchangeably herein to refer to a chemical compound that induces a desired effect such as inhibit viral replication, infection, maintenance, assembly and/or the function of an enzyme such as HBV DNA polymerase. The terms also encompass pharmaceutically acceptable and pharmacologically active ingredients of those active agents specifically mentioned herein including but not limited to salts, esters, amides, prodrugs, active metabolites, analogs and the like. When the terms "analog", "compound", "active agent", "pharmacologically active agent", "medicament", "active" and "drug" are used, then it is to be understood that this includes the active agent per se as well as pharmaceutically acceptable, pharmacologically active salts, esters, amides, prodrugs, metabolites, analogs, etc.

The present invention contemplates, therefore, compounds useful in inhibiting HBV replication, infection, maintenance, assembly and/or the function of an enzyme such as HBV DNA polymerase. Reference to an "analog", "compound", "active agent", "pharmacologically active agent", "medicament", "active" and "drug" such as ADV, LMV, FTC and/or TFV includes combinations of two or more actives such as ADV, LMV, TFV or FTC; ADV and LMV; ADV and TFV; LMV and TFV; FTC and ADV; FTC and TFV; FTC and LMV; ADV and LMV and TFV; or ADV and FTC and TFV; TFV and FTC and LMV; ADV and LMV and FTC; and/or ADV and FTC and LMV and TFV. A "combination" also includes a two-part or more such as a multi-part anti-HBV therapeutic composition where the agents are provided separately and given or dispensed separately or admixed together prior to dispensation.

The terms "effective amount" and "therapeutically effective amount" of an agent as used herein mean a sufficient amount of the agent to provide the desired therapeutic or physiological effect of inhibiting HBV replication, infection, maintenance, assembly and/or the function of an enzyme such as HBV DNA polymerase. Furthermore, an "effective HBV-inhibiting amount" or "effective symptom-ameliorating amount" of an agent is a sufficient amount of the agent to directly or indirectly inhibit replication, infection, maintenance, assembly and/or the function of an enzyme such as HBV DNA polymerase. Undesirable effects, e.g. side effects, are sometimes manifested along with the desired therapeutic effect; hence, a practitioner balances the potential benefits against the potential risks in determining what is an appropriate "effective amount". The exact amount required will vary from subject to subject, depending on the species, age and general condition of the subject, mode of administration and the like. Thus, it may not be possible to specify an exact "effective amount". However, an appropriate "effective amount" in any individual case may be determined by one of ordinary skill in the art using only routine experimentation.

By "pharmaceutically acceptable" carrier, excipient or diluent is meant a pharmaceutical vehicle comprised of a material that is not biologically or otherwise undesirable, i.e. the material may be administered to a subject along with the selected active agent without causing any or a substantial adverse reaction. Carriers may include excipients and other additives such as diluents, detergents, coloring agents, wetting or emulsifying agents, pH buffering agents, preservatives, and the like.

Similarly, a "pharmacologically acceptable" salt, ester, emide, prodrug or derivative of a compound as provided herein is a salt, ester, amide, prodrug or derivative that this not biologically or otherwise undesirable.

The terms "treating" and "treatment" as used herein refer to reduction in severity and/or frequency of symptoms, elimination of symptoms and/or underlying cause, prevention of the occurrence of symptoms and/or their underlying cause, and improvement or remediation of damage in relation to HBV infection. Thus, for example, "treating" a patient involves prevention of HBV infection as well as treatment of a clinically HBV symptomatic individual by inhibiting HBV replication, infection, maintenance, assembly and/or the function of an enzyme such as HBV DNA polymerase. Thus, for example, the present method of "treating" a patient with HBV infection or with a propensity for one to develop encompasses both prevention of HBV infection as well as treating HBV infection or symptoms thereof. In any event, the present invention contemplates the treatment or prophylaxis of HBV infection.

"Patient" as used herein refers to an animal, preferably a mammal and more preferably a primate including a lower primate and even more preferably, a human who can benefit from the formulations and methods of the present invention. A patient regardless of whether a human or non-human animal may be referred to as an individual, subject, animal, host or recipient. The compounds and methods of the present invention have applications in human medicine, veterinary medicine as well as in general, domestic or wild animal husbandry. For convenience, an "animal" includes an avian species such as a poultry bird (including ducks, chicken, turkeys and geese), an aviary bird or game bird. The condition in a non-human animal may not be a naturally occurring HBV infection but HBV-like infection may be induced.

As indicated above, the preferred animals are humans, non-human primates such as marmosets, baboons, orangutans, lower primates such as tupia, livestock animals, laboratory test animals, companion animals or captive wild animals. A human is the most preferred target. However, non-human animal models may be used.

Examples of laboratory test animals include mice, rats, rabbits, guinea pigs and hamsters. Rabbits and rodent animals, such as rats and mice, provide a convenient test system or animal model as do primates and lower primates. Livestock animals include sheep, cows, pigs, goats, horses and donkeys. Non-mammalian animals such as avian species, zebrafish, amphibians (including cane toads) and *Drosophila* species such as *Drosophila melanogaster* are also contemplated. Instead of a live animal model, a test system may also comprise a tissue culture system.

An "anti-HBV agent" includes a nucleoside or nucleotide analog, protein, chemical compound, RNA or DNA or RNAi or siRNA oligonucleotide (either DNA-derived or synthetic).

Preferably, the decreased sensitivity is in respect of ADV. Alternatively, the decreased sensitivity is in respect of LMV. Alternatively, the decreased sensitivity is in respect of TFV. Alternatively, the decreased sensitivity is in respect of FTC. Alternatively, the decreased sensitivity is in respect of ADV and LMV. Alternatively, the decreased sensitivity is in respect of ADV and TFV. Alternatively, the decreased sensitivity is in respect of LMV and TFV. Alternatively, the decreased sensitivity is in respect of ADV and FTC. Alternatively, the decreased sensitivity is in respect to FTC and TFV. Alternatively, the decreased sensitivity is in respect of FTC and LMV. Alternatively, the decreased sensitivity is in respect of ADV and LMV and TFV. Alternatively, the decreased sensitivity is in respect to ADV and TFV and FTC. Alternatively, the decreased sensitivity is in respect to LMV and TFV and FTC. Alternatively, the decrease sensitivity is in respect of ADV and LMV and FTC. Alternatively, the decreased sensitivity is in respect of ADV and FTC and TFV and LMV.

Reference herein to "anti-HBV agents" includes nucleoside and nucleotide analogs as well as immunological reagents (e.g. antibodies to HBV surface components) and chemical, proteinaceous and nucleic acid agents which inhibit or otherwise interfere with viral replication, maintenance, infection, assembly or release. Reference herein to "nucleic acid" includes reference to a sense or antisense molecule, RNA or DNA, oligonucleotides and RNAi and siRNA molecules and complexes containing same.

In addition to a mutation in the gene encoding DNA polymerase, due to the overlapping nature of the HBV genome (FIG. 1), a corresponding mutation may also occur in the gene encoding the S gene encoding the surface antigen (HBsAg) resulting in reduced interactivity of immunological reagents such as antibodies and immune cells to HBsAg. The reduction in the interactivity of immunological reagents to a viral surface component generally includes the absence of immunological memory to recognize or substantially recognize the viral surface component. The present invention extends, therefore, to an HBV variant exhibiting decreased sensitivity to ADV, LMV, TFV or FTC; ADV and LMV; ADV and TFV; LMV and TFV; FTC and ADV; FTC and TFV; FTC and LMV; ADV and LMV and TFV; or ADV and FTC and TFV; TFV and FTC and LMV; ADV and LMV and FTC; and/or ADV and FTC and LMV and TFV or a reduced interactivity of an immunological reagent to HBsAg wherein the variant is selected for following ADV and/or LMV combination or sequential treatment. The term "sequential" in this respect means ADV followed by LMV and/or TFV, and/or FTC, LMV followed by ADV and/or TFV, and/or FTC, or multiple sequential administrations of each of ADV, LMV and/or TFV, and/or FTC.

A viral variant may, therefore, carry A mutation only in the DNA polymerase gene or both in the DNA polymerase gene and the S gene. The term "mutation" is to be read in its broadest context and includes multiple mutations.

The present invention extends to a mutation and any domain of the HBV DNA polymerase and in particular regions F and G, and domains A through to E provided said mutation leads to decreased sensitivity to ADV and/or LMV and/or TFV or combinations thereof.

In this specification, reference is particularly made to the conserved regions of the DNA polymerase as defined by domains A to E. Regions A to E are defined by the amino acid sequence set forth in Formula II in Australian Patent No. 734831.

Preferably, the mutation results in an altered amino acid sequence in any one or more of domains F and G, and domains A through to E or regions proximal thereto of the HBV DNA polymerase.

Another aspect of the present invention provides an HBV variant comprising a mutation in an overlapping open reading frame in its genome wherein said mutation is in a region defined by one or more of domains F and G, and domains A through to E of HBV DNA polymerase and wherein said variant exhibits decreased sensitivity to ADV, LMV, TFV or FTC; ADV and LMV; ADV and TFV; LMV and TFV; FTC and ADV; FTC and TFV; FTC and LMV; ADV and LMV and TFV; or ADV and FTC and TFV; TFV and FTC and LMV; ADV and LMV and FTC; and/or ADV and FTC and LMV and TFV and/or optionally other nucleoside or nucleotide analogs or other anti-HBV agents.

Another preferred aspect of the present invention contemplates an HBV variant comprising a mutation in the nucleotide sequence encoding HBsAg resulting in an amino acid addition, substitution and/or deletion in said HBsAg wherein said variant exhibits decreased sensitivity to ADV, LMV, TFV, or FTC; or ADV and LMV; ADV and TFV; LMV and TFV; FTC and ADV; FTC and TFV; FTC and LMV; or ADV and LMV and TFV; or ADV and FTC and TFV; TFV and FTC and LMV; ADV and LMV and FTC; or ADV and FTC and LMV and TFV and/or optionally other nucleoside or nucleotide analogs or other anti-HBV agents or combination thereof.

More particularly, the present invention provides a variant HBV comprising a surface antigen having an amino acid sequence with a single or multiple amino acid substitution, addition and/or deletion or a truncation compared to a surface antigen from a reference or wild-type HBV and wherein an antibody generated to the reference or wild-type surface antigen exhibits reduced capacity for neutralizing said HBV variant, said variant selected by exposure of a subject to ADV, LMV, TFV, or FTC; or ADV and LMV; ADV and TFV; LMV and TFV; FTC and ADV; FTC and TFV; FTC and LMV; or ADV and LMV and TFV; or ADV and FTC and TFV; TFV and FTC and LMV; ADV and LMV and FTC; or ADV and FTC and LMV and TFV and/or optionally other nucleoside or nucleotide analogs or other anti-HBV agents or combination thereof.

The term "combination therapy" means that both combinations of ADV, LMV, FTC and/or TFV are co-administered in the same composition or simultaneously in separate compositions. The term "sequential therapy" means that the two agents are administered within seconds, minutes, hours, days or weeks of each other and in either order. Sequential therapy also encompasses completing a therapeutic course with one or other of ADV, LMV, FTC or TFV and then completing a second or third or subsequent therapeutic courses with the other of ADV, LMV, FTC or TFV.

Accordingly, another aspect of the present invention contemplates an HBV variant comprising a surface antigen having an amino acid sequence with a single or multiple amino acid substitution, addition and/or deletion or truncation compared to the pretreatment HBV and wherein the surface antigen of the variant HBV exhibits an altered immunological profile compared to the pretreatment HBV where the said variant HBV is selected for by exposure of a subject to ADV therapy or therapy by one or more other nucleoside or nucleotide analogs or other anti-HBV agents.

Another aspect of the present invention contemplates an HBV variant comprising a surface antigen having an amino acid sequence with a single or multiple amino acid substitution, addition and/or deletion or truncation compared to the pretreatment HBV and wherein the surface antigen of the variant HBV exhibits an altered immunological profile compared to the pretreatment HBV where the said variant HBV is selected for by exposure of a subject to LMV therapy or therapy by one or more other nucleoside or nucleotide analogs or other anti-HBV agents.

Yet another aspect of the present invention contemplates an HBV variant comprising a surface antigen having an amino acid sequence with a single or multiple amino acid substitution, addition and/or deletion or truncation compared to the pretreatment HBV and wherein the surface antigen of the variant HBV exhibits an altered immunological profile compared to the pretreatment HBV where the said variant HBV is selected for by exposure of a subject to FTC therapy or therapy by one or more other nucleoside or nucleotide analogs or other anti-HBV agents.

Still another aspect of the present invention contemplates an HBV variant comprising a surface antigen having an amino acid sequence with a single or multiple amino acid substitution, addition and/or deletion or truncation compared to the pretreatment HBV and wherein the surface antigen of the variant HBV exhibits an altered immunological profile compared to the pretreatment HBV where the said variant HBV is selected for by exposure of a subject to TFV therapy or therapy by one or more other nucleoside or nucleotide analogs or other anti-HBV agents.

Even yet another aspect of the present invention contemplates an HBV variant comprising a surface antigen having an amino acid sequence with a single or multiple amino acid substitution, addition and/or deletion or truncation compared to the pretreatment HBV and wherein the surface antigen of the variant HBV exhibits an altered immunological profile compared to the pretreatment HBV where the said variant HBV is selected for by exposure of a subject to ADV and LMV therapy or therapy by one or more other nucleoside or nucleotide analogs or other anti-HBV agents.

Even still another aspect of the present invention contemplates an HBV variant comprising a surface antigen having an amino acid sequence with a single or multiple amino acid substitution, addition and/or deletion or truncation compared to the pretreatment HBV and wherein the surface antigen of the variant HBV exhibits an altered immunological profile compared to the pretreatment HBV where the said variant HBV is selected for by exposure of a subject to ADV and TFV therapy or therapy by one or more other nucleoside or nucleotide analogs or other anti-HBV agents.

A further aspect of the present invention contemplates an HBV variant comprising a surface antigen having an amino acid sequence with a single or multiple amino acid substitution, addition and/or deletion or truncation compared to the pretreatment HBV and wherein the surface antigen of the variant HBV exhibits an altered immunological profile compared to the pretreatment HBV where the said variant HBV is selected for by exposure of a subject to LMV and TFV therapy or therapy by one or more other nucleoside or nucleotide analogs or other anti-HBV agents.

Another aspect of the present invention contemplates an HBV variant comprising a surface antigen having an amino acid sequence with a single or multiple amino acid substitution, addition and/or deletion or truncation compared to the pretreatment HBV and wherein the surface antigen of the variant HBV exhibits an altered immunological profile compared to the pretreatment HBV where the said variant HBV is selected for by exposure of a subject to ADV and FTC therapy or therapy by one or more other nucleoside or nucleotide analogs or other anti-HBV agents.

Yet another aspect of the present invention contemplates an HBV variant comprising a surface antigen having an amino acid sequence with a single or multiple amino acid substitution, addition and/or deletion or truncation compared to the pretreatment HBV and wherein the surface antigen of the variant HBV exhibits an altered immunological profile compared to the pretreatment HBV where the said variant HBV is selected for by exposure of a subject to TFV and FTC therapy or therapy by one or more other nucleoside or nucleotide analogs or other anti-HBV agents.

Still another aspect of the present invention contemplates an HBV variant comprising a surface antigen having an amino acid sequence with a single or multiple amino acid substitution, addition and/or deletion or truncation compared to the pretreatment HBV and wherein the surface antigen of the variant HBV exhibits an altered immunological profile compared to the pretreatment HBV where the said variant HBV is selected for by exposure of a subject to FTC and LMV therapy or therapy by one or more other nucleoside or nucleotide analogs or other anti-HBV agents.

Even yet another aspect of the present invention contemplates an HBV variant comprising a surface antigen having an amino acid sequence with a single or multiple amino acid substitution, addition and/or deletion or truncation compared to the pretreatment HBV and wherein the surface antigen of the variant HBV exhibits an altered immunological profile compared to the pretreatment HBV where the said variant HBV is selected for by exposure of a subject to ADV, LMV and TFV therapy or therapy by one or more other nucleoside or nucleotide analogs or other anti-HBV agents.

Even still another aspect of the present invention contemplates an HBV variant comprising a surface antigen having an amino acid sequence with a single or multiple amino acid substitution, addition and/or deletion or truncation compared to the pretreatment HBV and wherein the surface antigen of the variant HBV exhibits an altered immunological profile compared to the pretreatment HBV where the said variant HBV is selected for by exposure of a subject to ADV, LMV and TFV therapy or therapy by one or more other nucleoside or nucleotide analogs or other anti-HBV agents.

A further aspect of the present invention contemplates an HBV variant comprising a surface antigen having an amino acid sequence with a single or multiple amino acid substitution, addition and/or deletion or truncation compared to the pretreatment HBV and wherein the surface antigen of the variant HBV exhibits an altered immunological profile compared to the pretreatment HBV where the said variant HBV is selected for by exposure of a subject to ADV, LMV and FTC therapy or therapy by one or more other nucleoside or nucleotide analogs or other anti-HBV agents.

Another aspect of the present invention contemplates an HBV variant comprising a surface antigen having an amino acid sequence with a single or multiple amino acid substitution, addition and/or deletion or truncation compared to the pretreatment HBV and wherein the surface antigen of the variant HBV exhibits an altered immunological profile compared to the pretreatment HBV where the said variant HBV is selected for by exposure of a subject to FTC, LMV and TFV therapy or therapy by one or more other nucleoside or nucleotide analogs or other anti-HBV agents.

Yet another aspect of the present invention contemplates an HBV variant comprising a surface antigen having an amino acid sequence with a single or multiple amino acid substitution, addition and/or deletion or truncation compared to the pretreatment HBV and wherein the surface antigen of the variant HBV exhibits an altered immunological profile compared to the pretreatment HBV where the said variant HBV is selected for by exposure of a subject to ADV, FTC and TFV therapy or therapy by one or more other nucleoside or nucleotide analogs or other anti-HBV agents.

Still yet another aspect of the present invention contemplates an HBV variant comprising a surface antigen having an amino acid sequence with a single or multiple amino acid substitution, addition and/or deletion or truncation compared to the pretreatment HBV and wherein the surface antigen of the variant HBV exhibits an altered immunological profile compared to the pretreatment HBV where the said variant HBV is selected for by exposure of a subject to ADV, LMV, FTC and TFV therapy or therapy by one or more other nucleoside or nucleotide analogs or other anti-HBV agents.

Preferably, the variants are in isolated form such that they have undergone at least one purification step away from naturally occurring body fluid. Alternatively, the variants may be maintained in isolated body fluid or may be in DNA form. The present invention also contemplates infectious molecular clones comprising the genome or parts thereof from a variant HBV. Furthermore, the present invention provides isolated components from the variant HBVs such as but not limited to an isolated HBsAg. Accordingly, the present invention provides an isolated HBsAg or a recombinant form thereof or derivative or chemical equivalent thereof, said HBsAg being from a variant HBV selected by exposure of a subject to one or more of ADV, LMV, FTC and/or TFV or optionally one or more nucleoside or nucleotide analogs or other anti-HBV agents.

More particularly, yet another aspect of the present invention is directed to an isolated variant HBsAg or a recombinant or derivative form thereof or a chemical equivalent thereof wherein said HBsAg or its recombinant or derivative form or its chemical equivalent exhibits an altered immunological profile compared to an HBsAg from a reference HBV, said HBsAg being from a variant HBV selected by exposure of a subject to one or more of ADV, LMV, FTC and/or TFV or optionally one or more nucleoside or nucleotide analogs or other anti-HBV agents.

Even more particularly, the present invention provides an isolated variant HBsAg or a recombinant or derivative form thereof or a chemical equivalent thereof wherein said HBsAg or its recombinant or derivative form or its chemical equivalent comprises an amino acid sequence with a single or multiple amino acid substitution, addition and/or deletion or a truncation compared to an HBsAg from a reference HBV and wherein a neutralizing antibody directed to a reference HBV exhibits no or reduced neutralising activity to an HBV carrying said variant HBsAg, said HBsAg being from a variant HBV selected by exposure of a subject to one or more of ADV, LMV, FTC and/or TFV or optionally one or more nucleoside or nucleotide analogs or other anti-HBV agents.

Preferred mutations in the HBV DNA polymerase include variants selected from patients with HBV recurrence following ADV, LMV, TFV, or FTC; or ADV and LMV; ADV and TFV; LMV and TFV; FTC and ADV; FTC and TFV; FTC and LMV; or ADV and LMV and TFV; or ADV and FTC and TFV; TFV and FTC and LMV; ADV and LMV and FTC; or ADV and FTC and LMV and TFV treatment. Nucleoside or nucleotide analogs or other anti-HBV agents may be indicated during, after or prior to a transplantation procedure (e.g. bone marrow transplantation (BMT) or OLT) or following treatment of patients diagnosed with hepatitis. Following selection of variants, viral loads are obtainable at levels similar to pre-treatment levels or increase while on therapy.

Useful mutants in the rt region include, in one embodiment, rtT38K, rtR55H and rtA181V; in another embodiment include rtS/T78S, rtV80L, rtN/S118N, rtN/K139K, rtE142V, rtA/T181A rtI204M, rtQ/P/S/Stop215S, rtE/K218E, rtN/H238H and rtY245H; in yet another embodiment include rtN238T; and yet another embodiment include rtI122V and rtA181T; in yet another embodiment include rtL180M, rtA/V200V, rtM204V, rtV214A, rtH237H/P, rtV253G, in yet another embodiment include rtT128N and rtN236T, in yet another embodiment include tL180M, rtM204V rtQ215S, in yet another embodiment include rtT128S rtL180M, rtM204V and rtQ215S, in yet another embodiment includes rtI80L, rtI204M, rtN238T, in yet another embodiment include rtN238T/A, in yet another embodiment include rtI187V, in yet another embodiment include rtN123N/I rtS135Y, rtV214A/V and rtQ215Q/P/Stop/S, or a combination thereof or an equivalent mutation Such HBV variants are proposed to exhibit a decreased sensitivity to ADV, LMV, TFV, or FTC; or ADV and LMV; ADV and TFV; LMV and TFV; FTC and ADV; FTC and TFV; FTC and LMV; or ADV and LMV and TFV; or ADV and FTC and TFV; TFV and FTC and LMV; ADV and LMV and FTC; or ADV and FTC and LMV and TFV and/or optionally other nucleoside or nucleotide analogs or other anti-HBV agents or combination thereof. It should be noted that the nomenclature system for amino acid positions is based on the methionine residues in the YMDD motif being designated codon rtM204. This numbering system is different to that in Australian Patent No. 734831 where the methionine residue in the YMDD motif within the polymerase gene is designated codon 550. In this regard, rtL180M and rtM204V correspond to L526M and M550V, respectively, in Australian Patent No. 734831. Corresponding mutations may also occur in envelope genes such as in one or more of PreS1, PreS2 and S.

Another potential mode of action of ADV and other acyclic nucleoside phosphonates is that of immune stimulation (Calio et al., *Antiviral Res.* 23: 77-89, 1994). A number of mutations resulted in changes in the envelope gene detected in HBV variants which may be associated with immune escape. These changes include in one embodiment include in one embodiment include sQ30K. sE44G, sA47T, sI126T, sA159V and sL173F, in another embodiment include sF55S, sC/Stop69C, sC/Y76Y, sI/V110I, sN/T131N, sN134Y, sStop/W172W, sStop/W196W, sS/R207R; in yet another embodiment include sV14A, sL95W, sV96G, and sI208T/I; and in yet another embodiment include sT47A and sW172stop, and in yet another embodiment include PreS2 T6S, sT47A, sP62L, sL/F192F, sI195M, and in yet another embodiment include sS53L, and in yet another embodiment include sP120T, and in yet another embodiment include sN40S, sS207R, and in yet another embodiment include sQ101R, sI195M, sS207R, and in yet another embodiment include sL95W and sL196W, and in yet another embodiment include sV14A, in yet another embodiment include sL42R, sQ102Q/R, sT115T/S, sS207S/R, sL215R and sL216Stop, or a combination thereof or an equivalent mutation.

The identification of the variants of the present invention permits the generation of a range of assays to detect such variants. The detection of such variants may be important in identifying resistant variants to determine the appropriate form of chemotherapy and/or to monitor vaccination protocols, or develop new or modified vaccine preparations.

Still another aspect of the present invention contemplates a method for determining the potential for an HBV to exhibit reduced sensitivity to ADV, LMV, TFV, or FTC; or ADV and LMV; ADV and TFV; LMV and TFV; FTC and ADV; FTC and TFV; FTC and LMV; or ADV and LMV and TFV; or ADV and FTC and TFV; TFV and FTC and LMV; ADV and LMV and FTC; or ADV and FTC and LMV and TFV and/or optionally other nucleoside or nucleotide analogs or other anti-HBV agents, said method comprising isolating DNA or corresponding mRNA from said HBV and screening for a mutation in the nucleotide sequence encoding HBV DNA polymerase resulting in at least one amino acid substitution, deletion and/or addition in any one or more of domains F and G, and A domains through to E or a region proximal thereto of said DNA polymerase and associated with resistance or decreased sensitivity to ADV, LMV, TFV, or FTC; or ADV and LMV; ADV and TFV; LMV and TFV; FTC and ADV; FTC and TFV; FTC and LMV; or ADV and LMV and TFV; or ADV and FTC and TFV; TFV and FTC and LMV; ADV and LMV and FTC; or ADV and FTC and LMV and TFV and/or optionally other nucleoside or nucleotide analogs or other anti-HBV agents wherein the presence of such a mutation is an indication of the likelihood of resistance to said ADV, LMV, TFV, or FTC; or ADV and LMV; ADV and TFV; LMV and TFV; FTC and ADV; FTC and TFV; FTC and LMV; or ADV and LMV and TFV; or ADV and FTC and TFV; TFV and FTC and LMV; ADV and LMV and FTC; or ADV and FTC and LMV and TFV and/or optionally other nucleoside or nucleotide analogs or other anti-HBV agents.

Accordingly, another aspect of the present invention provides a method for determining the potential for an HBV to exhibit reduced sensitivity to a nucleoside or nucleotide analog selected from ADV, LMV, TFV and FTC or optionally other nucleoside or nucleotide analogs, said method comprising isolating DNA or corresponding mRNA from said HBV and screening for a mutation in the nucleotide sequence encoding HBV DNA polymerase resulting in at least one amino acid substitution, deletion and/or addition in any one or more of domains F and A through E or a region proximal thereto of said DNA polymerase and associated with resistance or decreases sensitivity to one or more of ADV, LMV, TFV and/or FTC wherein the presence of such a mutation is an indication of the likelihood of resistance to said one or more of ADV, LMV, TFV and/or FTC.

Preferably, the assay detects one or more of the following mutations: in one embodiment, rtT38K, rtR55H and rtA181V; in another embodiment include rtS/T78S, rtV80L, rtN/S118N, rtN/K139K, rtE142V, rtA/T181A rtI204M, rtQ/P/S/Stop215S, rtE/K218E, rtN/H238H and rtY245H; in yet another embodiment include rtN238T; and yet another embodiment include rtI122V and rtA181T; in yet another embodiment include rtL180M, rtA/V200V, rtM204V, rtV214A, rtH237H/P, rtV253G, in yet another embodiment include rtT128N and rtN236T, in yet another embodiment include tL180M, rtM204V rtQ215S, in yet another embodiment include rtT128S rtL180M, rtM204V and rtQ215S, in yet another embodiment include rtI80L, rtI204M, rtN238T, in yet another embodiment include rtN238T/A, in yet another embodiment include rtI187V, in yet another embodiment include rtN123N/I rtS135Y, rtV214A/V and rtQ215Q/P/Stop/S, or combinations thereof or an equivalent one or more other mutation is indicative of a variant wherein said variant exhibits a decreased sensitivity to ADV, LMV, TFV, or FTC; or ADV and LMV; ADV and TFV; LMV and TFV; FTC and ADV; FTC and TFV; FTC and LMV; or ADV and LMV and TFV; or ADV and FTC and TFV; TFV and FTC and LMV; ADV and LMV and FTC; or ADV and FTC and LMV and TFV and/or optionally other nucleoside or nucleotide analogs or other anti-HBV agents or combination thereof.

Accordingly, another aspect of the present invention produces a method for determining whether an HBV strain exhibits reduced sensitivity to a nucleoside or nucleotide analog or other anti-HBV agents, said method comprising isolating DNA or corresponding mRNA from said HBV and screening for a mutation in the nucleotide sequence encoding the DNA polymerase and/or a corresponding region of the S gene, wherein the presence of a mutation selected from, in one embodiment include sQ30K. sE44G, sA47T, sI126T, sA159V and sL173F, in another embodiment include sF55S, sC/Stop69C, sC/Y76Y, sI/V110I, sN/T131N, sN134Y, sStop/W172W, sStop/W196W, sS/R207R; in yet another embodiment include sV14A, sL95W, sV96G, and sI208T/I; and in yet another embodiment include sT47A and sW172stop, and in yet another embodiment include PreS2 T6S, sT47A, sP62L, sL/F192F, sI195M, and in yet another embodiment include sS53L, and in yet another embodiment include sP120T, and in yet another embodiment include sN40S, sS207R, and in yet another embodiment include sQ101R, sI195M, sS207R, and in yet another embodiment include sL95W and sL196W, and in yet another embodiment include sV14A, in yet another embodiment include sL42R, sQ102Q/R, sT115T/S, sS207S/R, sL215R and sL216Stop and in yet another embodiment include sT47A and sW172stop, in even still another embodiment, rtT38K, rtR55H and rtA181V; in another embodiment include rtS/T78S, rtV80L, rtN/S118N, rtN/K139K, rtE142V, rtA/T181A rtI204M, rtQ/P/S/Stop215S, rtE/K218E, rtN/H238H and rtY245H; in yet another embodiment include rtN238T; and yet another embodiment include rtI122V and rtA181T; in yet another embodiment include rtL180M, rtA/V200V, rtM204V, rtV214A, rtH237H/P, rtV253G, in yet another embodiment include rtT128N and rtN236T, in yet another embodiment include tL180M, rtM204V rtQ215S, in yet another embodiment include rtT128S rtL180M, rtM204V and rtQ215S, in yet another embodiment includes rtI80L, rtI204M, rtN238T, in yet another embodiment include rtN238T/A, in yet another embodiment include rtI187V, in yet another embodiment include rtN123N/I rtS135Y, rtV214A/V and rtQ215Q/P/Stop/S, or combinations thereof or an equivalent one or more other mutation is indicative of a variant which exhibits a decreased sensitivity to ADV, LMV, TFV, or FTC; or ADV and LMV; ADV and TFV; LMV and TFV; FTC and ADV; FTC and TFV; FTC and LMV; or ADV and LMV and TFV; or ADV and FTC and TFV; TFV and FTC and LMV; ADV and LMV and FTC; or ADV and FTC and LMV and TFV and/or optionally other nucleoside or nucleotide analogs or other anti-HBV agents or combination thereof.

A further aspect of the present invention produces a method for determining whether an HBV strain exhibits reduced sensitivity to a nucleoside or nucleotide analog or other anti-HBV agents, said method comprising isolating DNA or corresponding mRNA from said HBV and screening for a mutation in the nucleotide sequence encoding the DNA polymerase and/or a corresponding region of the S gene, wherein the presence of a mutation selected from, in one embodiment, sQ30K, sE44G, sA47T, sI126T, sA159V and sL173F, in another embodiment include sF55S, sC/Stop69C, sC/Y76Y, sI/V110I, sN/T131N, sN134Y, sStop/W172W, sStop/W196W, sS/R207R; in yet another embodiment include sV14A, sL95W, sV96G, and sI208T/I; and in yet another embodiment include sT47A and sW172stop, and in yet another embodiment include PreS2 T6S, sT47A, sP62L, sL/F192F, sI195M, and in yet another embodiment include sS53L, and in yet another embodiment include sP120T, and in yet another embodiment include sN40S, sS207R, and in yet another embodiment include sQ101R, sI195M, sS207R, and in yet another embodiment include sL95W and sL196W, and in yet another embodiment include sV14A, in yet another embodiment include sL42R, sQ102Q/R, sT115T/S, sS207S/R, sL215R and sL216Stop and in yet another embodiment include sT47A and sW172stop, in even still another embodiment, rtT38K, rtR55H and rtA181V; in another embodiment include rtS/T78S, rtV80L, rtN/S118N, rtN/K139K, rtE142V, rtA/T188A rtI204M, rtQ/P/S/Stop215S, rtE/K218E, rtN/H238H and rtY245H; in yet another embodiment include rtN238T; and yet another embodiment include rtI122V and rtA181T; in yet another embodiment includes rtL180M, rtA/V200V, rtM204V, rtV214A, rtH237H/P, rtV253G, in yet another embodiment include rtT128N and rtN236T, in yet another embodiment include tL180M, rtM204V rtQ215S, in yet another embodiment include rtT128S rtL180M, rtM204V and rtQ215S, in yet another embodiment include rtI80L, rtI204M, rtN238T, in yet another embodiment include rtN238T/A, in yet another embodiment include rtI187V, in yet another embodiment include rtN123N/I rtS135Y, rtV214A/V and rtQ215Q/P/Stop/S, combinations thereof or an equivalent one or more other mutation is indicative of a variant which exhibits a decreased sensitivity to ADV, LMV, TFV, or FTC; or ADV and LMV; ADV and TFV; LMV and TFV; FTC and ADV; FTC and TFV; FTC and LMV; or ADV and LMV and TFV; or ADV and FTC and TFV; TFV and FTC and LMV; ADV and LMV and FTC; or ADV and FTC and LMV and TFV and/or optionally other nucleoside or nucleotide analogs or other anti-HBV agents or combination thereof.

The detection of HBV or its components in cells, cell lysates, cultured supernatant fluid and bodily fluid may be by any convenient means including any nucleic acid-based detection means, for example, by nucleic acid hybridization techniques or via one or more polymerase chain reactions (PCRs). The term "bodily fluid" includes any fluid derived from the blood, lymph, tissue or organ systems including serum, whole blood, biopsy and biopsy fluid, organ explants and organ suspension such as liver suspensions. The invention further encompasses the use of different assay formats of said nucleic acid-based detection means, including restriction fragment length polymorphism (RFLP), amplified fragment length polymorphism (AFLP), single-strand chain polymorphism (SSCP), amplification and mismatch detection (AMD), interspersed repetitive sequence polymerase chain reaction (IRS-PCR), inverse polymerase chain reaction (iPCR) and reverse transcription polymerase chain reaction (RT-PCR), amongst others. Other forms of detection include Northern blots, Southern blots, PCR sequencing, antibody procedures such as ELISA, Western blot and immunohistochemistry. A particularly useful assay includes the reagents and components required for immobilized oligonucleotide- or oligopeptide-mediated detection systems.

One particularly useful nucleic acid detection system is the reverse hybridization technique. In this technique, DNA from an HBV sample is amplified using a biotin or other ligand-labeled primer to generate a labeled amplicon. Oligonucleotides immobilized to a solid support such as a nitrocellulose film are then used to capture amplified DNA by hybridization. Specific nucleic acid fragments are identified via biotin or the ligand. Generally, the labeled primer is specific for a particular nucleotide variation to be detected. Amplification occurs only if the variation to be detected is present. There are many forms of the reverse hybridization assay and all are encompassed by the present invention.

Another aspect contemplated by the present invention provides a method for detecting a variant HBV exhibiting an altered immunological profile said method comprising isolating an HBV from a subject exposed to a nucleoside or nucleotide analog selected from the listed consisting of ADV, LMV, TFV or FTC; ADV and LMV; ADV and TFV; LMV and TFV; FTC and ADV; FTC and TFV; FTC and LMV; ADV and LMV and TFV; ADV and FTC and TFV; TFV and FTC and LMV; ADV and LMV and FTC; ADV and FTC and LMV and TFV, and then contacting said HBV with a panel of one or more antibodies to a surface antigen and screening for any change in binding affinity or binding spectrum.

In a related embodiment, the present invention contemplates a method for detecting a variant HBV exhibiting an altered immunological profile said method comprising isolating a serum sample from a subject exposed to a nucleoside or nucleotide analog selected from the listed consisting of ADV, LMV, TFV or FTC; ADV and LMV; ADV and TFV; LMV and TFV; FTC and ADV; FTC and TFV; FTC and LMV; ADV and LMV and TFV; ADV and FTC and TFV; TFV and FTC and LMV; ADV and LMV and FTC; ADV and FTC and LMV and TFV, and then contacting the serum with a panel of HBV surface antigens or antibody-binding fragments thereof and screening for any change in binding affinity or binding spectrum.

Detecting HBV replication in cell culture is particularly useful.

This and other aspects of the present invention is particularly amenable to microarray analysis such as to identify oligonucleotides including sense and antisense molecules, RNAi or siRNA molecules or DNA or RNA-binding molecules which down-regulate genomic sequences or transcripts of HBV. Microarray analysis may also be used to identify particular mutations in the HBV genome such as within the HBV DNA polymerase-coding region or the HBsAg-coding region.

Another aspect of the present invention contemplates a method for detecting an agent which exhibits inhibitory activity to an HBV by:

generating a genetic construct comprising a replication competent-effective amount of the genome from the HBV contained in a plasmid vector and then transfecting said cells with said construct;

contacting the cells, before, during and/or after transfection, with the agent to be tested;

culturing the cells for a time and under conditions sufficient for the HBV to replicate, express genetic sequences and/or assemble and/or release virus or virus-like particles if resistant to said agents; and then subjecting the cells, cell lysates or culture supernatant fluid to viral- or viral-component-detection means to determine whether or not the virus has replicated, expressed genetic material and/or assembled and/or been released in the presence of the agent.

In a preferred embodiment, the plasmid vector may include genes encoding part or all of other viral vectors such as baculovirus or adenovirus (Ren and Nassal, 2001, supra) and the method comprises:

generating a genetic construct comprising a replication competent-effective amount of the genome from the HBV contained in or fused to an amount of a baculovirus genome or adenovirus genome effective to infect cells and then infecting said cells with said construct;

contacting the cells, before, during and/or after infection, with the agent to be tested;

culturing the cells for a time and under conditions sufficient for the HBV to replicate, express genetic sequences and/or assemble and/or release virus or virus-like particles if resistant to said agent; and then subjecting the cells, cell lysates or culture supernatant fluid to viral- or viral-component-detection means to determine whether or not the virus has replicated, expressed genetic material and/or assembled and/or been released in the presence of the agent.

In an alternative embodiment, the method comprises:

generating a continuous cell line comprising an infectious copy of the genome of the HBV in a replication competent effective amount such that said infectious HBV genome is stably integrated into said continuous cell line such as but not limited to 2.2.15 or AD;

contacting the cells with the agent to be tested;

culturing the cells for a time and under conditions sufficient for the HBV to replicate, express genetic sequences and/or assemble and/or release virus or virus-like particles if resistant to the agent; and then subjecting the cells, cell lysates or culture supernatant fluid to viral- or viral-component-detection means to determine whether or not the virus has replicated, expressed genetic material and/or assembled and/or been released in the presence of the agent.

The above-mentioned methods are particularly useful in identifying or developing agents against HBV variants such as those carrying mutations, in one embodiment, rtT38K, rtR55H and rtA181V; in another embodiment include rtS/T78S, rtV80L, rtN/S118N, rtN/K139K, rtE142V, rtA/T181A rtI204M, rtQ/P/S/Stop215S, rtE/K218E, rtN/H238H and rtY245H; in yet another embodiment include rtN238T; and yet another embodiment includes rtI122V and rtA181T; in yet another embodiment include rtL180M, rtA/V200V, rtM204V, rtV214A, rtH237H/P, rtV253G, in yet another embodiment include rtT128N and rtN236T, in yet another embodiment include tL180M, rtM204V rtQ215S, in yet another embodiment include rtT128S rtL180M, rtM204V and rtQ215S, in yet another embodiment include rtI80L, rtI204M, rtN238T, in yet another embodiment include rtN238T/A, in yet another embodiment includes rtI187V, in yet another embodiment includes rtN123N/I rtS135Y, rtV214A/V and rtQ215Q/P/Stop/S, or a combination thereof or an equivalent mutation; in a further embodiment, sQ30K. sE44G, sA47T, sI126T, sA159V and sL173F, in another embodiment include sF55S, sC/Stop69C, sC/Y76Y, sI/V110I, sN/T131N, sN134Y, sStop/W172W, sStop/W196W, sS/R207R; in yet another embodiment include sV14A, sL95W, sV96G, and sI208T/I; and in yet another embodiment include sT47A and sW172stop, and in yet another embodiment include PreS2 T6S, sT47A, sP62L, sL/F192F, sI195M, and in yet another embodiment include sS53L, and in yet another embodiment include sP120T, and in yet another embodiment include sN40S, sS207R, and in yet another embodiment include sQ101R, sI195M, sS207R, and in yet another embodiment include sL95W and sL196W, and in yet another embodiment include sV14A, in yet another embodiment include sL42R, sQ102Q/R, sT115T/S, sS207S/R, sL215R and sL216Stop, or a combination thereof or an equivalent mutation.

Accordingly, another aspect of the present invention contemplates a method for determining whether an HBV strain exhibits reduced sensitivity to a nucleoside or nucleotide analog or other potential anti-HBV agent, said method comprising isolating DNA or corresponding mRNA from said HBV and screening for a mutation in the nucleotide sequence of the envelope genes or DNA polymerase gene selected from, in one embodiment, in one embodiment, rtT3SK, rtR55H and rtA181V; in another embodiment includes rtS/T78S, rtV80L, rtN/S118N, rtN/K139K, rtE142V, rtA/T181A rtI204M, rtQ/P/S/Stop215S, rtE/K218E, rtN/H238H and rtY245H; in yet another embodiment include rtN238T; and yet another embodiment include rtI122V and rtA181T; in yet another embodiment include rtL180M, rtA/V200V, rtM204V, rtV214A, rtH237H/P, rtV253G, in yet another embodiment include rtT128N and rtN236T, in yet another embodiment include tL180M, rtM204V rtQ215S, in yet another embodiment include rtT128S rtL180M, rtM204V and rtQ215S, in yet another embodiment include rtI80L, rtI204M, rtN238T, in yet another embodiment include rtN238T/A, in yet another embodiment include rtI187V, in yet another embodiment include rtN123N/I rtS135Y, rtV214A/V and rtQ215Q/P/Stop/S, or a combination thereof or an equivalent mutation; in a her embodiment, sQ30K. sE44G, sA47T, sI126T, sA159V and sL173F, in another embodiment include sF55S, sC/Stop69C, sC/Y76Y, sI/V110I, sN/T131N, sN134Y, sStop/W172W, sStop/W196W, sS/R207R; in yet another embodiment include sV14A, sL95W, sV96G, and sI208T/I; and in yet another embodiment include sT47A and sW172stop, and in yet another embodiment include PreS2 T6S, sT47A, sP62L, sL/F192F, sI195M, and in yet another embodiment include sS53L, and in yet another embodiment include sP120T, and in yet another embodiment include sN40S, sS207R, and in yet another embodiment include sQ101R, sI195M, sS207R, and in yet another embodiment include sL95W and sL196W, and in yet another embodiment include sV14A, in yet another embodiment include sL42R, sQ102Q/R, sT115T/S, sS207S/R, sL215R and sL216Stop, or combinations thereof or an equivalent one or more other mutation is indicative of a variant wherein said variant exhibits a decreased sensitivity to ADV, LMV, TFV, or FTC; or ADV and LMV; ADV and TFV; LMV and TFV; FTC and ADV; FTC and TFV; FTC and LMV; or ADV and LMV and TFV; or ADV and FTC and TFV; TFV and FTC and LMV; ADV and LMV and FTC; or ADV and FTC and LMV and TFV and/or optionally other nucleoside or nucleotide analogs or other anti-HBV agents or combination thereof.

The detection of amino acid variants of DNA polymerase is conveniently accomplished by a range of amino acid detection techniques. Where an HBV variant comprises an amino acid change, then such an isolate is considered a putative HBV variant having an altered DNA polymerase activity.

The present invention further contemplates agents which inhibit ADV, LMV, TFV, or FTC; or ADV and LMV; ADV and TFV; LMV and TFV; FTC and ADV; FTC and TFV; FTC and LMV; or ADV and LMV and TFV; or ADV and FTC and TFV; TFV and FTC and LMV; ADV and LMV and FTC; or ADV and FTC and LMV and TFV resistant HBV variants. Such agents are particularly useful if long term treatment by ADV, LMV, FTC and/or TFV and/or optionally other nucleoside or nucleotide analogs such as TFV is contemplated by the clinician. The agents may be DNA or RNA or proteinaceous or non-proteinaceous chemical molecules. Natural product screening such as from plants, coral and microorganisms is also contemplated as a useful potential source of masking agents as is the screening of combinatorial or chemical libraries. The agents may be in isolated form or in the form of a pharmaceutical composition or formulation and may be administered in place of or sequentially or simultaneously with a nucleoside or nucleotide analog. Furthermore, rationale drug design is contemplated including solving the crystal or NMR structure of, for example, HBV DNA polymerase and designing agents which can bind to the enzyme's active site. This approach may also be adapted to other HBV components.

Accordingly, another aspect of the present invention contemplates a method for detecting an agent which exhibits inhibitory activity to an HBV which exhibits resistance or decreased sensitivity to ADV, LMV, TFV, or FTC; or ADV and LMV; ADV and TFV; LMV and TFV; FTC and ADV; FTC and TFV; FTC and LMV; or ADV and LMV and TFV; or ADV and FTC and TFV; TFV and FTC and LMV; ADV and LMV and FTC; or ADV and FTC and LMV and TFV and/or optionally other nucleoside or nucleotide analogs or other anti-HBV agents or combination thereof said method comprising:

generating a genetic construct comprising a replication competent-effective amount of the genome from said HBV contained in a plasmid vector and then transfecting said cells with said construct;

contacting said cells, before, during and/or after transfection, with the agent to be tested;

culturing said cells for a time and under conditions sufficient for the HBV to replicate, express genetic sequences and/or assemble and/or release virus or virus-like particles if resistant to said agent; and
- subjecting the cells, cell lysates or culture supernatant fluid to viral- or viral-component-detection means to determine whether or not the virus has replicated, expressed genetic material and/or assembled and/or been released in the presence of said agent.

Still another aspect of the present invention provides a method for detecting an agent which exhibits inhibitory activity to an HBV which exhibits resistance or decreased sensitivity to ADV, LMV, TFV, or FTC; or ADV and LMV; ADV and TFV; LMV and TFV; FTC and ADV; FTC and TFV; FTC and LMV; or ADV and LMV and TFV; or ADV and FTC and TFV; TFV and FTC and LMV; ADV and LMV and FTC; or ADV and FTC and LMV and TFV and/or optionally other nucleoside or nucleotide analogs or other anti-HBV agents or combination thereof, said method comprising:

- generating a genetic construct comprising a replication competent-effective amount of the genome from said HBV contained in or fused to an amount of a baculovirus genome effective to infect cells and then infecting said cells with said construct;
- contacting said cells, before, during and/or after infection, with the agent to be tested;
- culturing said cells for a time and under conditions sufficient for the HBV to replicate, express genetic sequences and/or assemble and/or release virus or virus-like particles if resistant to said agent; and
- subjecting the cells, cell lysates or culture supernatant fluid to viral- or viral-component-detection means to determine whether or not the virus has replicated, expressed genetic material and/or assembled and/or been released in the presence of said agent.

Preferably, the HBV genome is stably integrated into the cells' genome.

Particularly useful cells are 2.2.15 cells (Price et al., *Proc. Nail. Acad. Sci. USA* 86(21): 8541-8544, 1989 or AD cells (also known as HepAD32 cells or HepAD79 cells [Ying et al., *Viral Hepat* 7(2):161-165, 2000.

Whilst the baculovirus vector is a particularly useful in the practice of the present invention, the subject invention extends to a range of other vectors such as but not limited to adenoviral vectors.

The present invention further extends to cell lines (e.g. 2.2.15 or AD cells) carrying genetic constructs comprising all or a portion of an HBV genome or a gene or part of a gene therefrom.

The present invention also provides for the use of the subject HBV variants to screen for anti-viral agents. These anti-viral agents inhibit the virus. The term "inhibit" includes antagonizing or otherwise preventing infection, replication, assembly and/or release or any intermediate step. Preferred anti-viral agents include nucleoside or nucleotide analogs or anti-HBV agents, however, the present invention extends to non-nucleoside molecules.

In addition, rational drug design is also contemplated to identify or generate chemical molecules which either mimic a nucleoside or which interact with a particular nucleotide sequence or a particular nucleotide. Combinatorial chemistry and two hybrid screening are some of a number of techniques which can be employed to identify potential therapeutic or diagnostic agents.

In one example, the crystal structure or the NMR structure of polymerase or the surface antigen is used to rationally design small chemical molecules likely to interact with key regions of the molecule required for function and/or antigenicity. Such agents may be useful as inhibitors of polymerase activity and/or may alter an epitope on the surface antigen.

Several models of the HBV polymerase have been prepared due to the similarity with reverse transcriptase from HIV (Das et al., *J. Virol.* 75(10): 4771-4779, 2001; Bartholomeusz et al., *Intervirology* 40(5-6): 337-342 1997; Allen et al., *Hepatology* 27(6): 1670-1677, 1998). The models of the HBV polymerase can be used for the rational drug design of new agents effective against HBV encoding the resistant mutations as well as wild type virus. The rational drug that is designed may be based on a modification of an existing anti-viral agent such as the agent used in the selection of the HBV encoding the mutations associated with resistance. Viruses or clones expressing HBV genomic material encoding the mutations may also be used to screen for new antiviral agents.

In an alternative embodiment the present invention also contemplates a method for detecting an agent which exhibits inhibitory activity to an HBV polymerase in an in vitro polymerase assay. The HBV polymerase activity can be examined using established assays (Gaillard et al., *Antimicrob Agents Chemother.* 46(4): 1005-1013, 2002; Xiong et al., *Hepatology* 28(6): 1669-1673, 1998).

As indicated above, microarray technology is also a useful means of identifying agents which are capable of interacting with defined HBV internal or external components. For example, arrays of HBV DNA polymerase or peptide fragments thereof carrying different amino acid variants may be used to screen for agents which are capable of binding or otherwise interacting with these molecules. This is a convenient way of determining the differential binding patterns of agents between HBV variants. Arrays of antibodies may also be used to screen for altered HBsAg molecules. Microarrays are also useful in proteomic analysis to identify molecules such as antibodies, interferons or cytokines which have an ability to interact with an HBV component. Microarrays of DNA and RNA molecules may also be employed to identify sense and antisense molecules for genetic regions on the HBV genome or transcripts thereof.

The above methods are particularly useful in identifying an inhibitor of an HBV resistant to or exhibiting reduced sensitivity to ADV, LMV, TFV, or FTC; or ADV and LMV; ADV and TFV; LMV and TFV; FTC and ADV; FTC and TFV; FTC and LMV; or ADV and LMV and TFV; or ADV and FTC and TFV; TFV and FTC and LMV; ADV and LMV and FTC; or ADV and FTC and LMV and TFV and/or optionally other nucleoside or nucleotide analogs or other anti-HBV agents or combination thereof. The present invention extends, therefore, to compositions of the inhibitors. The inhibitors may also be in the form of antibodies or genetic molecules such as ribozymes, antisense molecules and/or sense molecules for co-suppression or the induction of RNAi or may be other nucleoside or nucleotide analogs or other anti-HBV agents or derivatives of known analogs. Reference to RNAi includes reference to short, interfering RNAs (siRNA) and all RNAi-type molecules may be DNA-derived or synthetic.

The term "composition" includes a "pharmaceutical composition" or a formulation.

The inhibitor is referred to below as an "active ingredient" or "active compound" and may be selected from the list of inhibitors given above.

The composition may include an antigenic component of the HBV, a defective HBV variant or an agent identified through natural product screening or rational drug design (including combinatorial chemistry).

Pharmaceutically acceptable carriers and/or diluents include any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, use thereof in the therapeutic compositions is contemplated. Supplementary active ingredients can also be incorporated into the compositions.

The pharmaceutical composition may also comprise genetic molecules such as a vector capable of transfecting target cells where the vector carries a nucleic acid molecule capable of encoding an aspartyl protease inhibitor. The vector may, for example, be a viral vector.

Pharmaceutical forms suitable for injectable use include sterile aqueous solutions (where water soluble) and sterile powders for the extemporaneous preparation of sterile injectable solutions. It must be stable under the conditions of manufacture and storage and must be preserved against the contaminating action of microorganisms such as bacteria and fungi. The carrier can be a solvent or dilution medium comprising, for example, water, ethanol, polyol (for example, glycerol, propylene glycol and liquid polyethylene glycol, and the like), suitable mixtures thereof and vegetable oils. The proper fluidity can be maintained, for example, by the use of superfactants. The preventions of the action of microorganisms can be brought about by various anti-bacterial and anti-fungal agents, for example, parabens, chlorobutanol, phenol, sorbic acid, thimerosal and the like. In many cases, it will be preferable to include isotonic agents, for example, sugars or sodium chloride. Prolonged absorption of the injectable compositions can be brought about by the use in the compositions of agents delaying absorption, for example, aluminium monostearate and gelatin.

Sterile injectable solutions are prepared by incorporating the active compounds in the required amount in the appropriate solvent with the active ingredient and optionally other active ingredients as required, followed by filtered sterilization or other appropriate means of sterilization. In the case of sterile powders for the preparation of sterile injectable solutions, suitable methods of preparation include vacuum drying and the freeze-drying technique which yield a powder of active ingredient plus any additionally desired ingredient.

When the active ingredient is suitably protected, it may be orally administered, for example, with an inert diluent or with an assimilable edible carrier, or it may be enclosed in hard or soft shell gelatin capsule, or it may be compressed into tablets. For oral therapeutic administration, the active ingredient may be incorporated with excipients and used in the form of ingestible tablets, buccal tablets, troches, capsules, elixirs, suspensions, syrups, wafers and the like. Such compositions and preparations should contain at least 1% by weight of active compound. The percentage of the compositions and preparations may, of course, be varied and may conveniently be between about 5 to about 80% of the weight of the unit. The amount of active compound in such therapeutically useful compositions is such that a suitable dosage will be obtained. Preferred compositions or preparations according to the present invention are prepared so that an oral dosage unit form contains between about 0.1 µg and 200 mg of active compound. Alternative dosage amounts include from about 1 µg to about 1000 mg and from about 10 µg to about 500 mg. These dosages may be per individual or per kg body weight. Administration may be per hour, day, week, month or year.

The tablets, troches, pills, capsules and the like may also contain the components as listed hereafter. A binder such as gum, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavouring agent such as peppermint, oil of wintergreen or cherry flavouring. When the dosage unit form is a capsule, it may contain, in addition to materials of the above type, a liquid carrier. Various other materials may be present as coatings or to otherwise modify the physical form of the dosage unit. For instance, tablets, pills or capsules may be coated with shellac, sugar or both. A syrup or elixir may contain the active compound, sucrose as a sweetening agent, methyl and propylparabens as preservatives, a dye and a flavouring. Of course, any material used in preparing any dosage unit form should be pharmaceutically pure and substantially non-toxic in the amounts employed. In addition, the active compound(s) may be incorporated into sustained-release preparations and formulations.

As stated above, the present invention further extends to an isolated HBsAg from the HBV variants herein described. More particularly, the present invention provides an HBsAg or a recombinant form thereof or derivative or chemical equivalent thereof. The isolated surface component and, more particularly, isolated surface antigen or its recombinant, derivative or chemical equivalents are useful in the development of biological compositions such as vaccine formulations.

Yet another aspect of the present invention provides a composition comprising a variant HBV resistant to ADV, LMV, TFV, or FTC; or ADV and LMV; ADV and TFV; LMV and TFV; FTC and ADV; FTC and TFV; FTC and LMV; or ADV and LMV and TFV; or ADV and FTC and TFV; TFV and FTC and LMV; ADV and LMV and FTC; or ADV and FTC and LMV and TFV and/or optionally other nucleoside or nucleotide analogs or other anti-HBV agents or an HBV surface antigen from said variant HBV or a recombinant or derivative form thereof or its chemical equivalent and one or more pharmaceutically acceptable carriers and/or diluents. Such a composition may be regarded as a therapeutic composition and is useful in generating an immune response including a humoral response. Generally, the HBV variants are "defective" and in themselves are unable to cause a sustained infection in a subject.

As indicated above, antibodies may be generated to the mutant HBV agents and used for passive or direct vaccination against infection by these viruses. The antibodies may be generated in humans or non-human animals. In the case of the latter, the non-human antibodies may need to be deimmunized or more specifically humanized prior to use. Deimmunized may include, for example, grafting complementarity determining regions (CDRs) from the variable region of a murine or non-human animal anti-HBV antibody onto a human consensus fragment antibody binding (Fab) polypeptide. Alternatively, amino acids defining epitopes in the variable region of the antibody may be mutated so that the epitopes are no longer recognized by the human MHC II complex.

Insofar as ribozyme, antisense or co-suppression (RNAi) or siRNA or complexes thereof repression is concerned, this is conveniently aimed at post-transcription gene silencing. DNA or RNA may be administered or a complex comprising RNAi or a chemical analog thereof specific for HBV mRNA may be employed.

All such molecules may be incorporated into pharmaceutical compositions.

In another embodiment, the present invention provides a biological composition comprising a variant HBV or an HBsAg or L, M or S proteins from said variant HBV or a recombinant or derivative form thereof or its chemical equivalent.

Generally, if an HBV is used, it is first attenuated The biological composition according to this aspect of the present invention generally further comprises one or more pharmaceutically acceptable carriers and/or diluents.

The biological composition may comprise HBsAg or like molecule from one HBV variant or the composition may be a cocktail of HbsAgs or L, M or S proteins or like molecules from a range of ADV- and/or LMV- and/or, FTC- and/or TFV-resistant HBV variants. Similar inclusions apply where the composition comprises an HBV.

The present invention is further directed to the use of defective HBV variants in the manufacture of therapeutic vaccines to vaccinate individuals against infection by HBV strains having a particular nucleotide sequence or encoding a particular polymerase or surface antigen or L, M or S proteins.

Examples of suitable vaccine candidates are defective forms of HBV variants comprising a mutation selected from, in one embodiment, in one embodiment, rtT3SK, rtR55H and rtA181V; in another embodiment include rtS/T78S, rtV80L, rtN/S118N, rtN/K139K, rtE142V, rtA/T181A rtI204M, rtQ/P/S/Stop215S, rtE/K218E, rtN/H238H and rtY245H; in yet another embodiment include rtN238T; and yet another embodiment include rtI122V and rtA181T; in yet another embodiment include rtL180M, rtA200V, rtM204V, rtV214A, rtH237H/P, rtV253G, in yet another embodiment include rtT128N and rtN236T, in yet another embodiment include tL180M, rtM204V rtQ215S, in yet another embodiment include rtT128S rtL180M, rtM204V and rtQ215S, in yet another embodiment include rtI80L, rtI204M, rtN238T, in yet another embodiment include rtN238T/A, in yet another embodiment include rtI187V, in yet another embodiment include rtN123N/I rtS135Y, rtV214A/V and rtQ215Q/P/Stop/S, or a combination thereof or an equivalent mutation; in a further embodiment, sQ30K. sE44G, sA47T, sI126T, sA159V and sL173F, in another embodiment include sF55S, sC/Stop69C, sC/Y76Y, sI/V110I, sN/T131N, sN134Y, sStop/W172W, sStop/W196W, sS/R207R; in yet another embodiment include sV14A, sL95W, sV96G, and sI208T/I; and in yet another embodiment include sT47A and sW172stop, and in yet another embodiment include PreS2 T6S, sT47A, sP62L, sL/F192F, sI195M, and in yet another embodiment include sS53L, and in yet another embodiment include sP120T, and in yet another embodiment include sN40S, sS207R, and in yet another embodiment include sQ101R, sI195M, sS207R, and in yet another embodiment include sL95W and sL196W, and in yet another embodiment include sV14A, in yet another embodiment include sL42R, sQ102Q/R, sT115T/S, sS207S/R, sL215R and sL216Stop, or a combination thereof or an equivalent mutation.

In one embodiment, for example, an HBV variant may be identified having a particular mutation in its polymerase conferring resistance or decreased sensitivity to a nucleoside or nucleotide analog. This variant may then be mutated to render it defective, i.e. attenuated or unable to cause infection. Such a defective, nucleoside or nucleotide analog-resistant virus may then be used as a therapeutic vaccine against virulent viruses having the same mutation in its polymerase.

The subject invention extends to kits for assays for variant HBV resistant to ADV, LMV, TFV, or FTC; or ADV and LMV; ADV and TFV; LMV and TFV; FTC and ADV; FTC and TFV; FTC and LMV; or ADV and LMV and TFV; or ADV and FTC and TFV; TFV and FTC and LMV; ADV and LMV and FTC; or ADV and FTC and LMV and TFV. Such kits may, for example, contain the reagents from PCR or other nucleic acid hybridization technology or reagents for immunologically based detection techniques. A particularly useful assay includes the reagents and components required for immobilized oligonucleotide- or oligopeptide-mediated detection systems.

Still another aspect of the present invention contemplates a method for determining the potential for an HBV to exhibit reduced sensitivity to ADV, LMV, TFV, or FTC; or ADV and LMV; ADV and TFV; LMV and TFV; FTC and ADV; FTC and TFV; FTC and LMV; or ADV and LMV and TFV; or ADV and FTC and TFV; TFV and FTC and LMV; ADV and LMV and FTC; or ADV and FTC and LMV and TFV and/or optionally other nucleoside or nucleotide analogs or other anti-HBV agents or combination thereof, said method comprising isolating DNA or corresponding mRNA from said HBV and screening for a mutation in the nucleotide sequence encoding HBV DNA polymerase resulting in at least one amino acid substitution, deletion and/or addition in any one or more of domains F and G, and domains A through to E or a region proximal thereto of said DNA polymerase and associated with resistance or decreased sensitivity to ADV, LMV, TFV, or FTC; or ADV and LMV; ADV and TFV; LMV and TFV; FTC and ADV; FTC and TFV; FTC and LMV; or ADV and LMV and TFV; or ADV and FTC and TFV; TFV and FTC and LMV; ADV and LMV and FTC; or ADV and FTC and LMV and TFV, wherein the presence of such a mutation is an indication of the likelihood of resistance to said ADV, LMV, TFV, or FTC; or ADV and LMV; ADV and TFV; LMV and TFV; FTC and ADV; FTC and TFV; FTC and LMV; or ADV and LMV and TFV; or ADV and FTC and TFV; TFV and FTC and LMV; ADV and LMV and FTC; or ADV and FTC and LMV and TFV.

An assessment of a potential viral variant is important for selection of an appropriate therapeutic protocol. Such an assessment is suitably facilitated with the assistance of a computer programmed with software, which inter alia adds input codes for at least two features associated with the viral variants to provide a value corresponding to the resistance or sensitivity of a viral variant to a particular chemical compound or immunological agent. The value can be selected from (a) the ability to exhibit resistance for reduced sensitivity to a particular compound or immunological agent; (b) an altered DNA polymerase from wild-type HBV; (c) an altered surface antigen from wild-type HBV; or (d) morbidity or recovery potential of a patient. Thus, in accordance with the present invention, the values for such features are stored in a machine-readable storage medium, which is capable of processing the data to provide a value for a particular viral variant or a biological specimen comprising same.

Thus, in another aspect, the invention contemplates a computer program product for assessing the likely usefulness of a viral variant or biological sample comprising same for determining an appropriate therapeutic protocol in a subject (FIG. 3), said product comprising:
 (1) code that receives as input code for at least two features associated with said viral agents or biological sample comprising same, wherein said features are selected from:
  (a) the ability to exhibit resistance for reduced sensitivity to a particular compound or immunological agent;
  (b) an altered DNA polymerase from wild-type HBV;
  (c) an altered surface antigen from wild-type HBV; or
  (d) morbidity or recovery potential of a patient;
 (2) code that adds said input code to provide a sum corresponding to a value for said viral variants or biological samples; and
 (3) a computer readable medium that stores the codes.

In a related aspect, the invention extends to a computer for assessing the likely usefulness of a viral variant or biological sample comprising same in a subject, wherein said computer comprises:
 (1) a machine-readable data storage medium comprising a data storage material encoded with machine-readable data, wherein said machine-readable data comprise input codes for at least two features associated with said viral variant or biological sample; wherein said features are selected from:—
  (a) the ability to exhibit resistance for reduced sensitivity to a particular compound or immunological agent;
  (b) an altered DNA polymerase from wild-type HBV;
  (c) an altered surface antigen from wild-type HBV; or
  (d) morbidity or recovery potential of a patient;
 (2) a working memory for storing instructions for processing said machine-readable data;
 (3) a central-processing unit coupled to said working memory and to said machine-readable data storage medium, for processing said machine readable data to provide a sum of said input code corresponding to a value for said compound(s); and
 (4) an output hardware coupled to said central processing unit, for receiving said value.

Figure 3A:
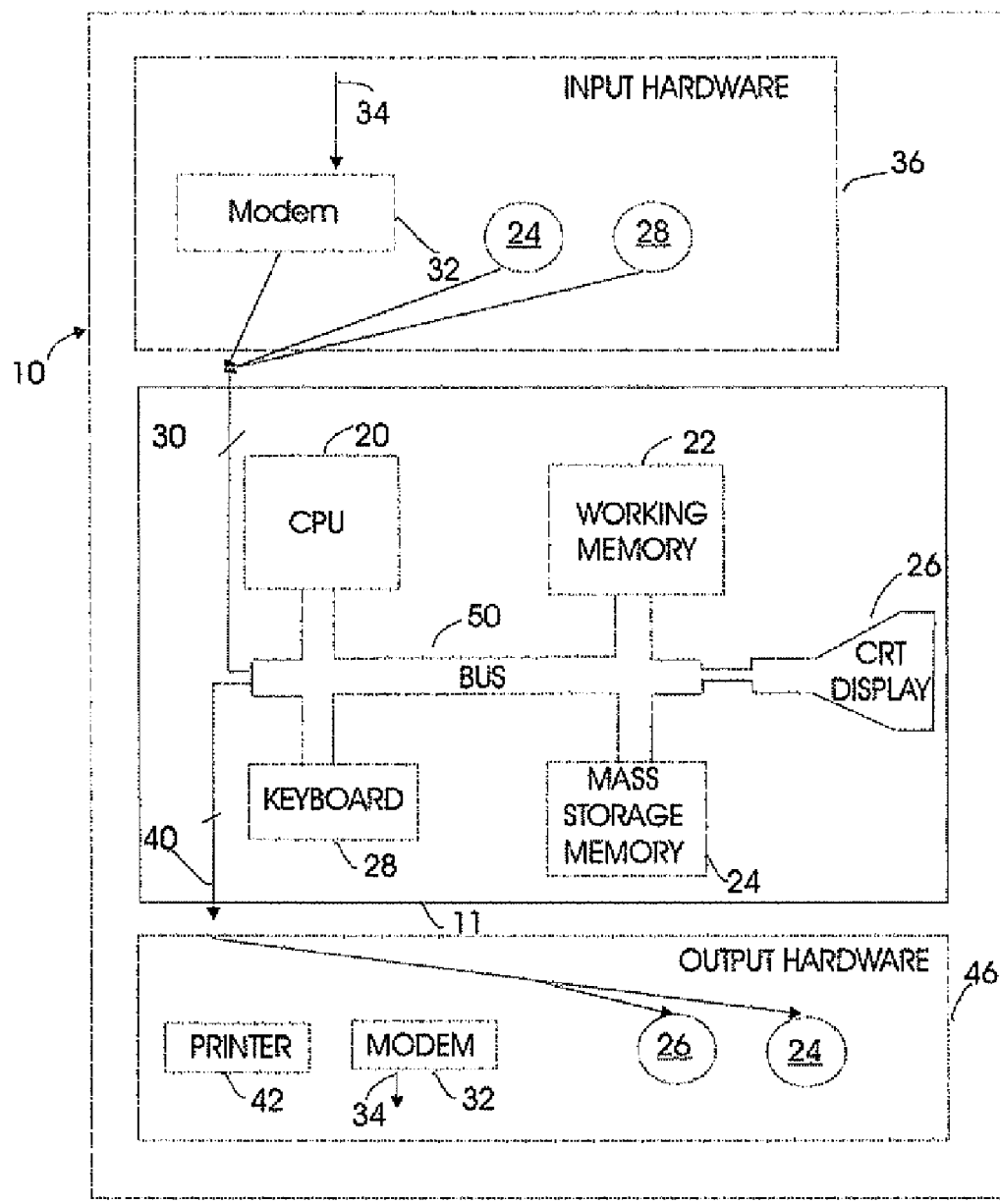
FIG. 3 is a diagrammatic representation of a computer system for determining the value of a variant HBV.
Figure 3B:
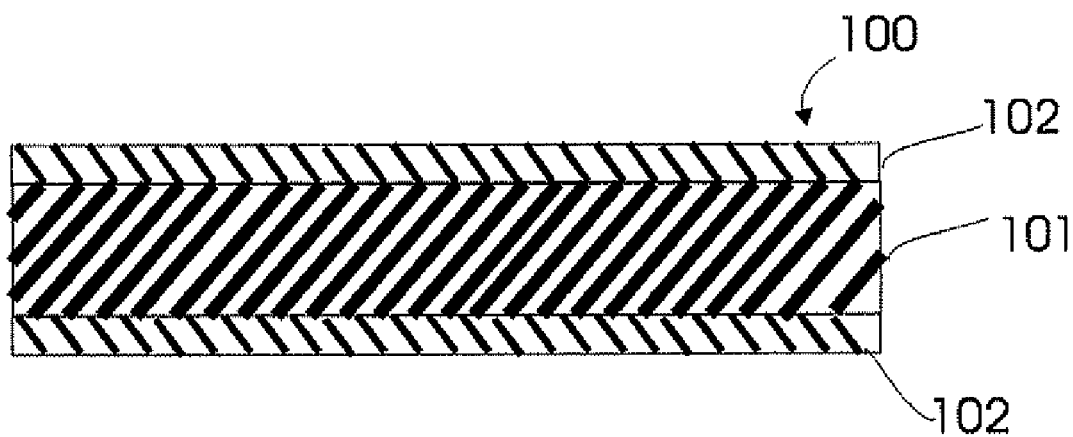
Figure 3C:
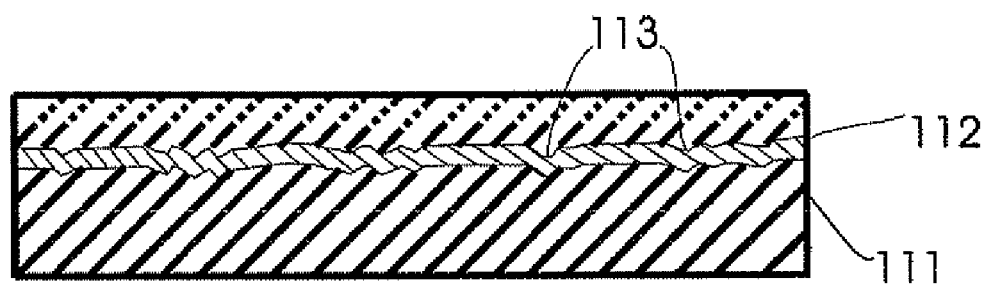

Any general or special purpose computer system is contemplated by the present invention and includes a processor in electrical communication with both a memory and at least one input/output device, such as a terminal. FIG. 3 shows a generally suitable computer system. Such a system may include, but is not limited to, personal computers, workstations or mainframes. The processor may be a general purpose processor or microprocessor or a specialized processor executing programs located in RAM memory. The programs may be placed in RAM from a storage device, such as a disk or pre-programmed ROM memory. The RAM memory in one embodiment is used both for data storage and program execution. The computer system also embraces systems where the processor and memory reside in different physical entities but which are in electrical communication by means of a network.

In an alternative embodiment, the program screens for a mutation selected from, in one embodiment, in one embodiment, rtT38K, rtR55H and rtA181V; in another embodiment include rtS/T78S, rtV80L, rtN/S118N, rtN/K139K, rtE142V, rtA/T181A rtI204M, rtQ/P/S/Stop215S, rtE/K218E, rtN/H238H and rtY245H; in yet another embodiment include rtN238T; and yet another embodiment include rtI122V and rtA181T; in yet another embodiment include rtL180M, rtA/V200V, rtM204V, rtV214A, rtH237H/P, rtV253G, in yet another embodiment include rtT128N and rtN236T, in yet another embodiment include tL180M, rtA/V204V rtQ215S, in yet another embodiment include rtT128S rtL180M, rtM204V and rtQ215S, in yet another embodiment include rtI80L, rtI204M, rtN238T, in yet another embodiment include rtN238T/A, in yet another embodiment include rtI187V, in yet another embodiment include rtN123N/I rtS135Y, rtV214A/V and rtQ215Q/P/Stop/S, or a combination thereof or an equivalent mutation; in a further embodiment, sQ30K. sE44G, sA47T, sI126T, sA159V and sL173F, in another embodiment include sF55S, sC/Stop69C, sC/Y76Y, sI/V110I, sN/T131N, sN134Y, sStop/W172W, sStop/W196W, sS/R207R; in yet another embodiment include sV14A, sL195W, sV96G, and sI208T/I; and in yet another embodiment include sT47A and sW172stop, and in yet another embodiment include PreS2 T6S, sT47A, sP62L, sL/F192F, sI195M, and in yet another embodiment include sS53L, and in yet another embodiment include sP120T, and in yet another embodiment include sN40S, sS207R, and in yet another embodiment include sQ101R, sI195M, sS207R, and in yet another embodiment include sL95W and sL196W, and in yet another embodiment include sV14A, in yet another embodiment include sL42R, sQ102Q/R, sT115T/S, sS207S/R, sL215R and sL216Stop, or a combination thereof or an equivalent mutation.

The present invention is further described by the following non-limiting Examples.

Example 1

Overlapping Genome of HBV

The overlapping genome of HBV is represented in FIG. 1. The gene encoding DNA polymerase (P), overlaps the viral envelope genes, Pre-S1 and Pre-S2, and partially overlaps the X and core (C) genes. The HBV envelope comprises small, middle and large proteins HBV surface antigens. The large protein component is referred to as the HBV surface antigen (HBsAg) and is encoded by the S gene sequence. The Pre-S1 and Pre-S2 gene sequences encode the other envelope components.

Example 2

Patients on ADV Treatment and Analysis of HBV DNA

Patient A: During ADV treatment, unique HBV mutations were detected by sequencing (Table 4). This includes the unique mutation at rtT38K, and rtA181V. A number of other changes were also detected in the polymerase rtR55H and in the overlapping envelope gene (Table 4, FIGS. 4, 5 and 6). The changes in the HBsAg include sQ30K, sE44G, sA47T, sI126T, sA159V and sL173F. These unique changes were compared to reference sequences from each of the seven genotypes A-G as well as a consensus sequence from pretreatment samples to determine unique changes Patient B: The HBV mutations during ADV treatment are listed in Table 5 and FIGS. 7, 8, and 9. The unique changes in the rt region of the HBV DNA polymerase include rtY245H. Other changes in the HBV polymerase while on ADV treatment include rtS/T78S, rtV80L, rtN/S118N, rtN/K139K, rtE142V, rtA/T181A rtI204M, rtQ/P/S/Stop215S, rt E/K218E, rtN/H238H. The changes in the HBsAg while on ADV treatment include sF55S, sC/Stop69C, sC/Y76Y, sI/V110I, sN/T131N, sN134Y, sStop/W172W, sStop/W196W, sS/R207R.

Patient C: The HBV mutations prior to ADV treatment and during ADV treatment are listed in Table 6 and FIGS. 10, 11 and 12. The unique changes in the rt region of the HBV DNA polymerase while on ADV treatment include rtN238T. The unique changes in the HBsAg include sV14A, sL95W, sV96G, and sI208T/I Patient D: The HBV mutations during ADV treatment is listed in Table 7 and FIGS. 13, 14 and 15. The unique changes in the HBV DNA polymerase include rtI122V and rtA181T. The unique changes in the surface include sT47A and sW172stop.

Patient E. This patient was previously treated with lamivudine and selected the unique mutations rtH237H/P while on LMV. This patient did not respond to ADV treatment Changes in the polymerase on ADV treatment include rtL180M, rtA/V200V, rtM204V, rtV214A, rtH237H/P and rtV253G. The unique changes in the surface include PreS2 T6S, sT47A, sP62L, sL/F192F, sI195M. NB: Patient on TFV and responded Changes on ADV listed in Table 8 and FIGS. 16, 17 and 18.

Patient F: Unique changes during ADV treatment include the polymerase mutations at rtN238T and envelope mutations at sS53L. Changes on ADV listed in Table 9 and FIGS. 19, 20 and 21.

Patient G: Unique mutations while on ADV treatment include changes in the polymerase rtT128N and rtN236T and a change in envelope sP120T. Changes on ADV listed in Table 10 and FIGS. 22, 23 and 24.

Patient H: Mutations in the polymerase gene while on ADV treatment include rtL180MS rtM204V rtQ215S. Changes in envelope gene includes N40S, sS207R. Changes on ADV listed in Table 11 and FIGS. 25, 26 and 27.

Patient I: Mutations in the polymerase gene while on ADV treatment include rtT128S rtL180M, rtM204V and rtQ215S, while mutations in the envelope gene included sQ101R, sI195M, sS207R. Changes on ADV listed in Table 12 and FIGS. 28, 29 and 30.

Patient J: Mutations in the polymerase gene included rtI80L, rtI204M, rtN238T and mutations in envelope sL95W and sL196W during ADV treatment. Changes on ADV listed in Table 13 and FIGS. 31, 32 and 33.

Patient K: Mutations in the polymerase gene at rtN238T/A was detected during Adv treatment. No changes in envelope were detected during treatment. Changes on ADV listed in Table 14 and FIGS. 34, 35 and 36.

Patient L: Mutations in the polymerase gene at rtI187V was detected during ADV treatment. A mutation in the envelope gene at sV14A was also detected. Changes on ADV listed in Table 15 and FIGS. 37, 38 and 39.

Patient M is an HIV HBV co-infected patient treated with tenofovir and lamivudine as part of anti-retroviral therapy for HIV. These two agents are also useful in the treatment of HBV. This patient has not been treated with ADV. Three sequential samples were sequenced while the patient was on antiviral treatment: In one sample there were unique changes in the polymerase at rtN123N/I, rtS135Y, and rtQ215Q/P/stop/S. Unique changes in the envelope gene were detected at sL42R, sQ102Q/R, sT115T/S. These changes are listed in Table 16 and FIGS. 40, 41 and 42. The remaining two samples were identical to each other in the polymerase and envelope 9 (HBsAg) gene. Unique changes in the polymerase were detected at rtS135Y and rtV214A/V, and rtS207S/R and unique changes in the envelope gene were detected at sQ102Q/R, sL215R and sL216Stop while on TFV and LMV treatment. These changes are listed in Table 16 and FIGS. 43, 44 and 45.

The changes at rtQ215Q/P/Stop/S and rtV214A/V have been previously detected in ADV treated patients. Thus, these mutations are important mutations and may result in potential cross-resistance to both ADV and TFV.

Example 3

Detection of Viral Markers

Hepatitis B surface antigen (HBsAg), hepatitis B e antigen (HBeAg), anti-HBe and hepatitis B core antigen (HBcAg) specific IgG and IgM were measured using commercially available immunoassays (Abbott Laboratories, North Chicago, Ill., USA). Hepatitis B viral DNA levels were measured using a capture hybridization assay according to the manufacturer's directions (Digene Hybrid Capture II, Digene Diagnostics Inc., Beltsville, Md.). The manufacturers stated cut-off for detecting HBV viremia in clinical specimens was $0.7 \times 10^6$ copies/ml or 2.5 pg/ml, [Hendricks et al., *Am J Clin Pathol* 104: 537-46, 1995]. HBV DNA levels can also be quantitated using other commercial kits such as Cobas amplification HBV monitor kit (Roche).

Example 4

Sequencing of HBV DNA

HBV DNA was extracted from 100 µl of serum as described previously by Aye et al., *J. Hepatol.* 26: 1148-1153, 1997. Oligonucleotides were synthesized by Geneworks, Adelaide, Australia. Amplification of the HBV polymerase gene has been described by Aye et al., 1997, supra.

The specific amplified products were purified using PCR purification columns from MO BIO Laboratories Inc (La Jolla, Calif.) and directly sequenced using Big Dye terminator Cycle sequencing Ready Reaction Kit (Perkin Elmer, Cetus Norwalk, Conn.). The PCR primers were used as sequencing primers, OS1 5'-GCC TCA TTT TGT GGG TCA CCA TA-3' (nt 1408-1430) [SEQ ID NO:3], TTA3 5'-AAA TTC GCA GTC CCC AAA-3' (nt2128-2145) [SEQ ID NO:4], JM 5'-TTG GGG TGG AGC CCT CAG GCT-3' (nt1676-1696) [SEQ ID NO: 5], TTA4 5'-GAA AAT TGG TAA CAG CGG-3' (nt 2615-2632) [SEQ ID NO:6], OS2 5' TCT CTG ACA TAC TTT CCA AT 3' (nt 2798-2817) [SEQ ID NO:7], to sequence the internal regions of the PCR products.

Example 5

Adefovir Dipivoxil (ADV)

Figure 2:
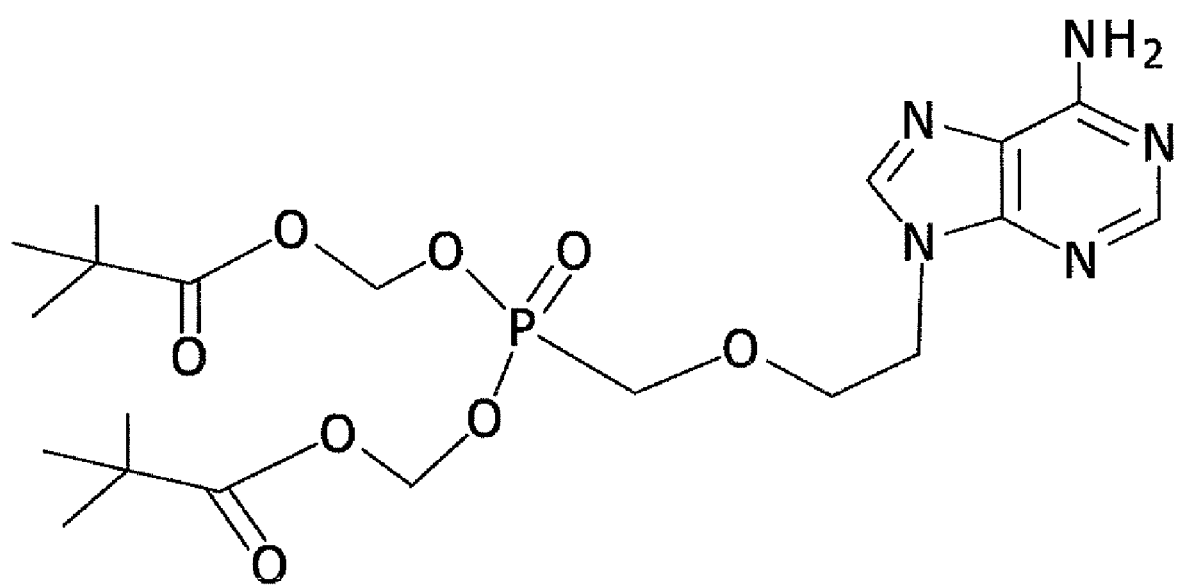
FIG. 2 is a diagrammatic representation of the chemical structure of ADV.

ADV (formerly Bis-pom PMEA)) is a potent inhibitor of HBV replication. The structure of ADV is shown in FIG. 2 and its synthesis is described by Benzaria et al., *J Med Chem.* 39: 4958-4965, 1996).

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features

TABLE 4

Patient A HBV Polymerase and envelope mutations detected during ADV therapy

| Treatment | Date | HBV viral load | HBV RT Mutations | HBsAg Mutations |
|---|---|---|---|---|
| ADV | 22 Oct. 2002 | 8.77E+06 | — | sT47A |
|  |  |  |  | sT131T/I |
| ADV | 14 Jan. 2003 | 1.21E+09 | — | — |
| ADV | 8 Jul. 2003 | 7.92E+07 | rtT38K | sL173F |
|  |  |  | rtA181V |  |

TABLE 5

Patient B RT and Polymerase mutations detected during ADV therapy

| Treatment | Date | HBV RT Mutations | HBsAg Mutations |
|---|---|---|---|
| ADV | 13 Feb. 2003 | rtV80L | — |
|  |  | — | sC76Y/C |
|  |  | rtN118N/S | sI110V/I |
|  |  | rtN139N/K | sN131N/T |
|  |  | — | sY134N |
|  |  | rtV142E | sW172Stop/W |
|  |  | rtA181A/T | sStop196W |
|  |  | rtI204M | sR/S207S |
|  |  | rtQ/P/S/Stop215Q |  |
|  |  | rtE218K/E |  |
|  |  | rtN238N/H |  |
| ADV | 21 Mar. 2003 | rtS78T/S | sS55F |
|  |  | rtV80L | sC69Stop |
|  |  | — | — |
|  |  | rtN118N/S | sC76Y/C |
|  |  | rtN139N/K | sI110V/I |
|  |  | — | sN131N/T |
|  |  | rtV142E | — |
|  |  | rtA181A/T | sY134N |
|  |  | rtI204M | sW172Stop/W |
|  |  | rtQ215 Q/P/S/Stop | sStop/W196W |
|  |  | rtE218K/E | sS207S/R |
|  |  | rtN238N/H |  |
| ADV | 22 Jul. 2003 | rtS/T78S | sF55S |
|  |  | rtV80L | sC/Stop69C |
|  |  | rtN/S118N | sC/Y76Y |
|  |  | rtN/K139K | sI/V110I |
|  |  | — | sN/T131N |
|  |  | rtE142V | — |
|  |  | rtA/T181A | sN134Y |
|  |  | — | sStop/W172W |
|  |  | rtI204M | sStop/W196W |
|  |  | rtQ/P/S/Stop21 | sS/R207R |
|  |  | rt5SE/K218E |  |
|  |  | rtN/H238H |  |
|  |  | rtY245H |  |

TABLE 6

Patient C HBV Polymerase and envelope mutations detected during ADV therapy

| Treatment | Date | HBV RT Mutations | HBsAg Mutations |
|---|---|---|---|
| ADV | 18 Aug. 2003 | rtN238T | sV14A |
|  |  |  | sL95W |
|  |  |  | sV96G |
|  |  |  | sI208T/I |

TABLE 7

Patient D HBV Polymerase and envelope mutations detected during ADV therapy

| Treatment | Date | HBV RT Mutations | HBsAg Mutations |
|---|---|---|---|
| ADV | 20 Aug. 2003 | rtI122V | sT47A |
|  |  | rtA181T | sW172Stop |

TABLE 8

Patient E HBV Polymerase and envelope mutations detected during ADV therapy

| Treatment | Date | HBV RT Mutations | HBsAg Mutations |
|---|---|---|---|
| LMV | 23 May 2002 | rtL180M | — |
|  |  | rtA200V/A | sL192L/F |
|  |  | rtM204V | sI195M |
|  |  | rtV214A |  |
|  |  | rtP237H |  |
| ADV | 17 Jul. 2003 | — | PreS2 T6S |
|  |  | — | sT47A |
|  |  | rtL180M | sP62L |
|  |  | rtA/V200V | sL/F192F |
|  |  | rtM204V | sI195M |
|  |  | rtV214A |  |
|  |  | rtH237H/P |  |
|  |  | rtV253G |  |

TABLE 9

Patient F HBV Polymerase and envelope mutations detected during ADV therapy

| Treatment | Date | HBV RT Mutations | HBsAg Mutations |
|---|---|---|---|
| ADV | 16 Oct. 2003 | rtN238T | sS53L |

TABLE 10

Patient G HBV Polymerase and envelope mutations detected during ADV therapy

| Treatment | Date | HBV RT Mutations | HBsAg Mutations |
|---|---|---|---|
| ADV | 12 Nov. 2003 | rtT128N | sP120T |
|  |  | rtN236T |  |

TABLE 11

Patient H HBV Polymerase and envelope mutations detected during ADV therapy

| Treatment | Date | HBV RT Mutations | HBsAg Mutations |
|---|---|---|---|
| ADV | 05 Nov. 2003 | rtL180M | sN40S |
|  |  | rtM204V | sI19SM |
|  |  | rtQ215S | sS207R |

TABLE 12

Patient I HBV Polymerase and envelope mutations detected during ADV therapy

| Treatment | Date | HBV RT Mutations | HBsAg Mutations |
|---|---|---|---|
| ADV | 05 Feb. 2003 | — | sQ101R |
|  |  | rtT128S | — |
|  |  | rtL180M | — |
|  |  | rtM204V | sI195M |
|  |  | rtQ215S | — |
|  |  | — | sS207R |

TABLE 13

Patient J HBV Polymerase and envelope mutations detected during ADV therapy

| Treatment | Date | HBV RT Mutations | HBsAg Mutations |
|---|---|---|---|
| ADV | 18 Nov. 2003 | rtI80L | — |
|  |  | — | sL95W |
|  |  | rtI204M | sL196W |
|  |  | rtN238T | — |

TABLE 14

Patient K HBV Polymerase and envelope mutations detected during ADV therapy

| Treatment | Date | HBV RT Mutations | HBsAg Mutations |
|---|---|---|---|
| ADV | 31 Mar. 2003 | rtN238T/A | No changes |

TABLE 15

Patient L HBV Polymerase and envelope mutations detected during ADV therapy

| Treatment | Date | HBV RT Mutations | HBsAg Mutations |
|---|---|---|---|
| ADV | 17 Sep. 2003 | rtI187V | sV14A |

TABLE 16

Patient M HBV Polymerase and envelope mutations detected during TFV and LMV therapy

| Treatment | Date | Viral load copie/ml | HBV RT Mutations | HBsAg Mutations |
|---|---|---|---|---|
| TFV LMV | 18 Jun. 2004 | 2.76E+06 | — | sL42R, |
|  |  |  | — | sQ102Q/R, |
|  |  |  | — | sT115T/S |
|  |  |  | rtN123N/I | sS207S/R |
|  |  |  | rtS135Y |  |
|  |  |  | rtQ215Q/P/stop/S |  |
| TFV LMV | 9 Jul. 2004 | 4.31E+07 | — | sQ102Q/R |
|  |  |  | rtS135Y | — |
|  |  |  | rtV214A/V | — |
|  |  |  | — | sL215R |
|  |  |  | — | sL216*. |
| TFV LMV | 22 Aug. 2004 | >1.00E+08 | — | sQ102Q/R |
|  |  |  | rtS135Y | — |
|  |  |  | rtV214A/V | — |
|  |  |  | — | sL215R |
|  |  |  | — | sL216*. |

BIBLIOGRAPHY

Allen et al., *Hepatology* 27(6): 1670-1677, 1998
Aye et al., *J. Hepatol.* 26: 1148-1153, 1997
Bartholomeusz et al., *Intervirology* 40(5-6): 337-342 1997
Benhamou et al., *Lancet* 358: 718-723, 2001
Benzaria et al., *J Med. Chem.* 39: 4958-4965, 1996
Boyd et al., *Antiviral Chem. Chemother.* 32: 358-363, 1987
Calio et al., *Antiviral Res.* 23: 77-89, 1994
Das et al., *J. Virol* 75(10): 4771-4779, 2001
Delaney et al., *Antimicrob. Agents Chemother* 45(6): 1705-1013, 2001
Dienstag et al., *New England J Med* 333: 1657-1661, 1995
Frick et al., *Antimicrob. Agents Chemother.* 37: 2285-2292, 1993
Gaillard et al., *Antimicrob Agents Chemother.* 46(4): 1005-1013, 2002
Gilson et al., *J Viral Hepat* 6: 387-395, 1999
Heathcote et al., *Hepatology* 28: A620, 1998
Hendricks et al., *Am J Clin Pathol* 104: 537-46, 1995
Kruger et al., *Hepatology* 22: 219A, 1994
Main et al., *J Viral Hepatitis* 3: 211-215, 1996
Norder et al., (*J. Gen. Virol* 74: 341-1348, 1993
Perillo et al., *Hepatology* 32: 129-134, 2000
Peters et al., *Transplantation* 68: 1912-1914, 1999
Price et al., *Proc. Natl. Acad. Sci. USA* 86(21): 8541-8544, 1989
Ren and Nassal, *J. Virol.* 75(3): 1104-1116, 2001
Severini et al., *Antimicrobial Agents Chemother.* 39: 430-435, 1995
Stuyver et al., *Hepatology* 33: 751-757, 2001
Summers and Mason, *Cell* 29: 403-415, 1982
Suo et al., *J Biol. Chem.* 273(42): 27250-27258.1998
Vere Hodge, *Antiviral Chem Chemother* 4: 67-84, 1993
Xiong et al., *Hepatology.* 28(6): 1669-73, 1998
Ying et al., *J Viral Hepat.* 7(2): 161-165, 2000
Ying et al., *J. Viral Hepat.* 7(1): 79-83, 2000
Ying et al., *Viral Hepat.* 7(2): 161-165, 2000

The invention claimed is:

1. A method for determining whether an HBV strain exhibits reduced sensitivity to Adefovir said method comprising isolating DNA or corresponding mRNA from the HBV strain and screening for the presence of a mutation in the nucleotide sequence encoding the HBV DNA polymerase resulting in a substitution in the amino acid sequence of the HBV DNA polymerase selected from the group consisting of rtQ215S and rtV253G, wherein the foregoing amino acid positions are numbered in reference to the M of the YMDD motif of the HBV DNA polymerase being position 204 and wherein the presence of said mutation is indicative of an HBV variant that exhibits a decreased sensitivity to Adefovir.

2. The method of claim 1 further comprising determining whether an HBV strain exhibits reduced sensitivity to Tenofovir said method comprising isolating DNA or corresponding mRNA from the HBV strain and screening for the presence of a mutation in the nucleotide sequence encoding the HBV DNA polymerase resulting in a substitution in the amino acid sequence of the HBV DNA polymerase selected from the group consisting of rtQ215S and rtV253G, wherein the foregoing amino acid positions are numbered in reference to the M of the YMDD motif of the HBV DNA polymerase being position 204 and wherein the presence of said mutation is indicative of an HBV variant that exhibits a decreased sensitivity to Tenofovir and Adefovir.

* * * * *

SEQUENCE LISTING

<160> NUMBER OF SEQ ID NOS: 42

<210> SEQ ID NO 1

<211> LENGTH: 1007
<212> TYPE: DNA
<213> ORGANISM: hepatitis B virus

<400> SEQUENCE: 1

```
gcttccacca atcggcaggc aggaagacag cctactccca tctctccacc tctaagagac      60
agtcatcctc aggccatgca gtggaactcc agcacattcc accatgctct gctagatccc     120
agacctgctg gtggctccag ttccggaaca gtaaaccctg ttccgactac tgcctctccc     180
atatcgtcaa tcttctcgag gactggggac cctgcgccga atatggagag caccacatca     240
ggattcctag gacccctgct cgtgttacag gcggggtttt tcttgttgac aagaatcctc     300
acaataccaa agagtctaga ctcgtggtgg acttctctca attttctagg gggagcaccc     360
acgtgtcctg gccaaaattt gcagtcccca acctccaatc actcaccaac ctcttgtcct     420
ccaatttgtc ctggttatcg ctggatgtgt ctgcggcgtt ttatcatctt cctcttcatc     480
ctgctgctat gcctcatctt cttgttggtt cttctggact accaaggtat gttgcccgtt     540
tgtcctctac ttccaggaac atcaactacc agcacgggac catgcaagac ctgcacgact     600
cctgctcaag gaacctctat gtttccctct gttgctgta caaaaccttc ggacggaaat      660
tgcacttgta ttcccatccc atcatcttgg ctttcgtaa gattcctatg ggagtgggcc      720
tcagtccgtt tctcctggtt cagtttacta gtgccatttg ttcagtggtt cgtagggctt     780
tcccccactg tttggctttc agttatatgg atgatgtggt attggggggcc aagtctgtac     840
aacatcttga tcccttttat accgctatta ccaattttct tttgtctttg ggtatacatt     900
taaaccctaa taaaaccaag cgttggggct actcccttaa cttcatggga tatgtaattg     960
gaagttgggg taccttgcca caggaacata ttgtacaaaa aatcaaa                  1007
```

<210> SEQ ID NO 2
<211> LENGTH: 270
<212> TYPE: PRT
<213> ORGANISM: hepatitis B virus

<400> SEQUENCE: 2

```
Glu Asp Trp Gly Pro Cys Ala Glu Tyr Gly Glu His His Ile Arg Ile
 1               5                  10                  15

Pro Arg Thr Pro Ala Arg Val Thr Gly Gly Val Phe Leu Val Asp Lys
                20                  25                  30

Asn Pro His Asn Thr Lys Glu Ser Arg Leu Val Val Asp Phe Ser Gln
            35                  40                  45

Phe Ser Arg Gly Ser Thr His Val Ser Trp Pro Lys Phe Ala Val Pro
        50                  55                  60

Asn Leu Gln Ser Leu Thr Asn Leu Leu Ser Ser Asn Leu Ser Trp Leu
    65                  70                  75                  80

Ser Leu Asp Val Ser Ala Ala Phe Tyr His Leu Pro Leu His Pro Ala
                85                  90                  95

Ala Met Pro His Leu Leu Val Gly Ser Ser Gly Leu Pro Arg Tyr Val
               100                 105                 110

Ala Arg Leu Ser Ser Thr Ser Arg Asn Ile Asn Tyr Gln His Gly Thr
           115                 120                 125

Met Gln Asp Leu His Asp Ser Cys Ser Arg Asn Leu Tyr Val Ser Leu
       130                 135                 140

Leu Leu Leu Tyr Lys Thr Phe Gly Arg Lys Leu His Leu Tyr Ser His
   145                 150                 155                 160

Pro Ile Ile Leu Gly Phe Arg Lys Ile Pro Met Gly Val Gly Leu Ser
               165                 170                 175
```

```
Pro Phe Leu Leu Val Gln Phe Thr Ser Ala Ile Cys Ser Val Val Arg
            180                 185                 190

Arg Ala Phe Pro His Cys Leu Ala Phe Ser Tyr Met Asp Asp Val Val
        195                 200                 205

Leu Gly Ala Lys Ser Val Gln His Leu Glu Ser Leu Tyr Thr Ala Ile
    210                 215                 220

Thr Asn Phe Leu Leu Ser Leu Gly Ile His Leu Asn Pro Asn Lys Thr
225                 230                 235                 240

Lys Arg Trp Gly Tyr Ser Leu Asn Phe Met Gly Tyr Val Ile Gly Ser
                245                 250                 255

Trp Gly Thr Leu Pro Gln Glu His Ile Val Gln Lys Ile Lys
                260                 265                 270

<210> SEQ ID NO 3
<211> LENGTH: 226
<212> TYPE: PRT
<213> ORGANISM: hepatitis B virus

<400> SEQUENCE: 3

Met Glu Ser Thr Thr Ser Gly Phe Leu Gly Pro Leu Leu Val Leu Gln
1               5                   10                  15

Ala Gly Phe Phe Leu Leu Thr Arg Ile Leu Thr Ile Pro Lys Ser Leu
            20                  25                  30

Asp Ser Trp Trp Thr Ser Leu Asn Phe Leu Gly Gly Ala Pro Thr Cys
        35                  40                  45

Pro Gly Gln Asn Leu Gln Ser Pro Thr Ser Asn His Ser Pro Thr Ser
    50                  55                  60

Cys Pro Pro Ile Cys Pro Gly Tyr Arg Trp Met Cys Leu Arg Arg Phe
65                  70                  75                  80

Ile Ile Phe Leu Phe Ile Leu Leu Cys Leu Ile Phe Leu Leu Val
                85                  90                  95

Leu Leu Asp Tyr Gln Gly Met Leu Pro Val Cys Pro Leu Leu Pro Gly
            100                 105                 110

Thr Ser Thr Thr Ser Thr Gly Pro Cys Lys Thr Cys Thr Thr Pro Ala
        115                 120                 125

Gln Gly Thr Ser Met Phe Pro Ser Cys Cys Cys Thr Lys Pro Ser Asp
    130                 135                 140

Gly Asn Cys Thr Cys Ile Pro Ile Pro Ser Ser Trp Ala Phe Val Arg
145                 150                 155                 160

Phe Leu Trp Glu Trp Ala Ser Val Arg Phe Ser Trp Phe Ser Leu Leu
                165                 170                 175

Val Pro Phe Val Gln Trp Phe Val Gly Leu Ser Pro Thr Val Trp Leu
            180                 185                 190

Ser Val Ile Trp Met Met Trp Tyr Trp Gly Pro Ser Leu Tyr Asn Ile
        195                 200                 205

Leu Asn Pro Phe Ile Pro Leu Leu Pro Ile Phe Phe Cys Leu Trp Val
    210                 215                 220

Tyr Ile
225

<210> SEQ ID NO 4
<211> LENGTH: 982
<212> TYPE: DNA
<213> ORGANISM: hepatitis B virus

<400> SEQUENCE: 4
```

```
tctgtctcca cctttgagag acactcatcc tcaggccatg cagtggaact ccacaacctt    60
ccaccaaact ctgcaagatc ccagagtgag aggcctgtat ttccctgctg gtggctccag   120
ttcaggaaca gtaaaccctg ttccgacttc tgtctctcac acatcgtcaa tcttctcgag   180
gattggggtc cctgcgctga acatggagaa catcacatca ggattcctag gacccctgct   240
cgtgttacag gcggggtttt tcttgttgac aagaatcctc acaataccgc agagtctaga   300
ctcgtggtgg acttctctca attttctagg gggaactacc gtgtgtcttg gccaaaattc   360
gcagtcccca acctccaatc actcaccaac ctcctgtcct ccaacttgtc ctggttatcg   420
ctggatgtat ctgcggcgtt ttatcatctt cctcttcatc ctgctgctat gcctcatctt   480
cttgttggtt cttctggact atcaaggtat gttgcccgtt tgtcctctaa ttccaggatc   540
ttcaaccacc agcacgggac catgcagaac ctgcacgact cctgctcaag gaaactctat   600
gtatccctcc tgttgctgta ccaaaccttc ggacggaaat tgcacctgta ttcccatccc   660
atcatcctgg gctttcggaa aattcctatg ggagtgggcc tcagcccgtt tctcctggct   720
cagtttacta gtgccatttg ttcagtggtt cgtagggctt cccccactg tttggctttc    780
agttatatgg atgatgtggt attggggggcc aagtctgtat cgcatcttga gtccctttttt  840
accgctgtta ccaattttct tttgtctttg ggtatacatt taaaccctca caaaacaaaa   900
agatggggtc actctttaca tttcatgggc tatgtcattg gatgttatgg gtcattgcca   960
caagatcaca tcagacagaa aa                                             982

<210> SEQ ID NO 5
<211> LENGTH: 268
<212> TYPE: PRT
<213> ORGANISM: hepatitis B virus

<400> SEQUENCE: 5

Glu Asp Trp Gly Pro Cys Ala Glu His Gly Glu His His Ile Arg Ile
1               5                   10                  15

Pro Arg Thr Pro Ala Arg Val Thr Gly Gly Val Phe Leu Val Asp Lys
            20                  25                  30

Asn Pro His Asn Thr Ala Glu Ser Arg Leu Val Val Asp Phe Ser Gln
        35                  40                  45

Phe Ser Arg Gly Asn Tyr Arg Val Ser Trp Pro Lys Phe Ala Val Pro
    50                  55                  60

Asn Leu Gln Ser Leu Thr Asn Leu Leu Ser Ser Asn Leu Ser Trp Leu
65                  70                  75                  80

Ser Leu Asp Val Ser Ala Ala Phe Tyr His Leu Pro Leu His Pro Ala
                85                  90                  95

Ala Met Pro His Leu Leu Val Gly Ser Ser Gly Leu Ser Arg Tyr Val
            100                 105                 110

Ala Arg Leu Ser Ser Asn Ser Arg Ile Phe Asn His Gln His Gly Thr
        115                 120                 125

Met Gln Asn Leu His Asp Ser Cys Ser Arg Lys Leu Tyr Val Ser Leu
    130                 135                 140

Leu Leu Leu Tyr Gln Thr Phe Gly Arg Lys Leu His Leu Tyr Ser His
145                 150                 155                 160

Pro Ile Ile Leu Gly Phe Arg Lys Ile Pro Met Gly Val Gly Leu Ser
                165                 170                 175

Pro Phe Leu Leu Ala Gln Phe Thr Ser Ala Ile Cys Ser Val Val Arg
            180                 185                 190

Arg Ala Phe Pro His Cys Leu Ala Phe Ser Tyr Met Asp Asp Val Val
        195                 200                 205
```

```
Leu Gly Ala Lys Ser Val Ser His Leu Glu Ser Leu Phe Thr Ala Val
        210                 215                 220

Thr Asn Phe Leu Leu Ser Leu Gly Ile His Leu Asn Pro His Lys Thr
225                 230                 235                 240

Lys Arg Trp Gly His Ser Leu His Phe Met Gly Tyr Val Ile Gly Cys
                245                 250                 255

Tyr Gly Ser Leu Pro Gln Asp His Ile Arg Gln Lys
        260                 265

<210> SEQ ID NO 6
<211> LENGTH: 226
<212> TYPE: PRT
<213> ORGANISM: hepatitis B virus

<400> SEQUENCE: 6

Met Glu Asn Ile Thr Ser Gly Phe Leu Gly Pro Leu Leu Val Leu Gln
1               5                   10                  15

Ala Gly Phe Phe Leu Leu Thr Arg Ile Leu Thr Ile Pro Gln Ser Leu
            20                  25                  30

Asp Ser Trp Trp Thr Ser Leu Asn Phe Leu Gly Gly Thr Thr Val Cys
        35                  40                  45

Leu Gly Gln Asn Ser Gln Ser Pro Thr Ser Asn His Ser Pro Thr Ser
    50                  55                  60

Cys Pro Pro Thr Cys Pro Gly Tyr Arg Trp Met Tyr Leu Arg Arg Phe
65                  70                  75                  80

Ile Ile Phe Leu Phe Ile Leu Leu Leu Cys Leu Ile Phe Leu Leu Val
                85                  90                  95

Leu Leu Asp Tyr Gln Gly Met Leu Pro Val Cys Pro Leu Ile Pro Gly
            100                 105                 110

Ser Ser Thr Thr Ser Thr Gly Pro Cys Arg Thr Cys Thr Thr Pro Ala
        115                 120                 125

Gln Gly Asn Ser Met Tyr Pro Ser Cys Cys Cys Thr Lys Pro Ser Asp
    130                 135                 140

Gly Asn Cys Thr Cys Ile Pro Ile Pro Ser Ser Trp Ala Phe Gly Lys
145                 150                 155                 160

Phe Leu Trp Glu Trp Ala Ser Ala Arg Phe Ser Trp Leu Ser Leu Leu
                165                 170                 175

Val Pro Phe Val Gln Trp Phe Val Gly Leu Ser Pro Thr Val Trp Leu
            180                 185                 190

Ser Val Ile Trp Met Met Trp Tyr Trp Gly Pro Ser Leu Tyr Arg Ile
        195                 200                 205

Leu Ser Pro Phe Leu Pro Leu Leu Pro Ile Phe Phe Cys Leu Trp Val
    210                 215                 220

Tyr Ile
225

<210> SEQ ID NO 7
<211> LENGTH: 1045
<212> TYPE: DNA
<213> ORGANISM: hepatitis B virus

<400> SEQUENCE: 7
cagcagcgcc tcctcctgcc tcctccaatc ggcagtcagg aagacagcct actcccatct      60
ctccacctct aagagacagt catcctcagg ccatgcagtg gaactccagc acattccacc     120
aagctctgct agatcccaga gtgagggggcc tatattttcc tgctggtggc tccagttccg    180
```

```
gaacagtaaa ccctgttccg actactgcct ctcccatatc gtcaatcttc tcgaggactg    240
gggaccctgc accgaacatg gagagcacca catcaggatt cctaggaccc ctgctcgcgt    300
tacaggcggg gttttcttg ttgacaagaa tcctcacaat accacagagt ctagactcgt    360
ggtggacttc tctcaatttt ctaggggga cacccaagtg tcctggccaa aatttgcagt    420
ccccaacctc caatcactca ccaacctctt gtcctccaat ttgtcctggt tatcgctgga    480
tgtgtctgcg gcgttttatc atcttcctct tcatcctgct gctatgcctc atcttcttgt    540
ggggtcttct ggactaccaa ggtatgttgc ccgtttgtcc tctacttcca ggaacatcaa    600
ctaccagcac gggaccatgc aagacctgca cgactcctgc tcaaggaacc tctatgtttc    660
cctcttgttg ctgtacaaaa ccttcggacg gaaattgcac ttgtattccc atcccatcat    720
cttgggcttt cgcaagattc ctatgggagt gggcctcagt ccgtttctcc tggctcagtt    780
tactagtgcc atttgttcag tggttcgtag gctttccccc actgtttggc ttttagtta     840 tatggatgat gtggtattgg gggccaagtc tgtacaacay cttgaatccc ttttaccgc     900 tgttaccaat tttcttttgt ctttgggtat acatttaaac cctactaaaa ccaaacgttg    960
gggctactcc cttaacttca tgggatatgt aattggaagt tggggtacct taccacaaga   1020
acatattgta cacaaaatca gacaa                                          1045

<210> SEQ ID NO 8
<211> LENGTH: 271
<212> TYPE: PRT
<213> ORGANISM: hepatitis B virus

<400> SEQUENCE: 8

Glu Asp Trp Gly Pro Cys Thr Glu His Gly Glu His His Ile Arg Ile
1               5                   10                  15

Pro Arg Thr Pro Ala Arg Val Thr Gly Gly Val Phe Leu Val Asp Lys
            20                  25                  30

Asn Pro His Asn Thr Thr Glu Ser Arg Leu Val Val Asp Phe Ser Gln
        35                  40                  45

Phe Ser Arg Gly Asn Thr Gln Val Ser Trp Pro Lys Phe Ala Val Pro
    50                  55                  60

Asn Leu Gln Ser Leu Thr Asn Leu Leu Ser Ser Asn Leu Ser Trp Leu
65                  70                  75                  80

Ser Leu Asp Val Ser Ala Ala Phe Tyr His Leu Pro Leu His Pro Ala
                85                  90                  95

Ala Met Pro His Leu Leu Val Gly Ser Ser Gly Leu Pro Arg Tyr Val
            100                 105                 110

Ala Arg Leu Ser Ser Thr Ser Arg Asn Ile Asn Tyr Gln His Gly Thr
        115                 120                 125

Met Gln Asp Leu His Asp Ser Cys Ser Arg Asn Leu Tyr Val Ser Leu
    130                 135                 140

Leu Leu Leu Tyr Lys Thr Phe Gly Arg Lys Leu His Leu Tyr Ser His
145                 150                 155                 160

Pro Ile Ile Leu Gly Phe Arg Lys Ile Pro Met Gly Val Gly Leu Ser
                165                 170                 175

Pro Phe Leu Leu Ala Gln Phe Thr Ser Ala Ile Cys Ser Val Val Arg
            180                 185                 190

Arg Ala Phe Pro His Cys Leu Ala Phe Ser Tyr Met Asp Asp Val Val
        195                 200                 205

Leu Gly Ala Lys Ser Val Gln His Leu Glu Ser Leu Phe Thr Ala Val
    210                 215                 220
```

Thr Asn Phe Leu Leu Ser Leu Gly Ile His Leu Asn Pro Thr Lys Thr
225                 230                 235                 240

Lys Arg Trp Gly Tyr Ser Leu Asn Phe Met Gly Tyr Val Ile Gly Ser
            245                 250                 255

Trp Gly Thr Leu Pro Gln Glu His Ile Val His Lys Ile Arg Gln
        260                 265                 270

<210> SEQ ID NO 9
<211> LENGTH: 226
<212> TYPE: PRT
<213> ORGANISM: hepatitis B virus
<220> FEATURE:
<221> NAME/KEY: MISC_FEATURE
<222> LOCATION: (208)..(208)
<223> OTHER INFORMATION: Xaa is any amino acid

<400> SEQUENCE: 9

Met Glu Ser Thr Thr Ser Gly Phe Leu Gly Pro Leu Leu Ala Leu Gln
1               5                   10                  15

Ala Gly Phe Phe Leu Leu Thr Arg Ile Leu Thr Ile Pro Gln Ser Leu
            20                  25                  30

Asp Ser Trp Trp Thr Ser Leu Asn Phe Leu Gly Gly Thr Pro Lys Cys
        35                  40                  45

Pro Gly Gln Asn Leu Gln Ser Pro Thr Ser Asn His Ser Pro Thr Ser
    50                  55                  60

Cys Pro Pro Ile Cys Pro Gly Tyr Arg Trp Met Cys Leu Arg Arg Phe
65                  70                  75                  80

Ile Ile Phe Leu Phe Ile Leu Leu Leu Cys Leu Ile Phe Leu Trp Gly
                85                  90                  95

Leu Leu Asp Tyr Gln Gly Met Leu Pro Val Cys Pro Leu Leu Pro Gly
            100                 105                 110

Thr Ser Thr Thr Ser Thr Gly Pro Cys Lys Thr Cys Thr Thr Pro Ala
        115                 120                 125

Gln Gly Thr Ser Met Phe Pro Ser Cys Cys Cys Thr Lys Pro Ser Asp
    130                 135                 140

Gly Asn Cys Thr Cys Ile Pro Ile Pro Ser Ser Trp Ala Phe Ala Arg
145                 150                 155                 160

Phe Leu Trp Glu Trp Ala Ser Val Arg Phe Ser Trp Leu Ser Leu Leu
                165                 170                 175

Val Pro Phe Val Gln Trp Phe Val Gly Leu Ser Pro Thr Val Trp Leu
            180                 185                 190

Leu Val Ile Trp Met Met Trp Tyr Trp Gly Pro Ser Leu Tyr Asn Xaa
        195                 200                 205

Leu Asn Pro Phe Leu Pro Leu Leu Pro Ile Phe Phe Cys Leu Trp Val
    210                 215                 220

Tyr Ile
225

<210> SEQ ID NO 10
<211> LENGTH: 1021
<212> TYPE: DNA
<213> ORGANISM: hepatitis B virus

<400> SEQUENCE: 10
ctcctgcatc taccaatcgg cagtcaggaa gacagcctac tcccatctct ccacctctaa    60
gagacagtca tcctcaggcc atgcagtgga actccacaac tttccaccaa gctctgctag   120
atccccgagt gaggggcctc tatttttcctg ctggtggctc cagttccggg acagtaaacc   180

```
ctgttccgac tactgcctct cccatatcgt caatcttctc gaggactggg gaccctgcac    240
tgaacatgga gagcacaaca tcaggattcc taggacccct gctcgtgtta caggcggtgt    300
ttttcttgtt gacaagaatc ctcacaatac cacagagtct agactcgtgg tggacttctc    360
tcaatttctc aggggaagca cccgcgtgtc ctggccaaaa ttcgcagtcc caacctcca    420 atcactcacc aacctcttgt cctccaattt gtcctggcta tcgctggatg tgtctgcggc    480
gttttatcat cttcctcttc atcctgctgc tatgcctcat cttcttgttg gttcttctgg    540
attaccaagg tatgttgccc gtttgtcctc tacttccagg aacgtcaact accagcacgg    600
gaccatgcaa gacctgcacg attcctgctc aaggaacctc tatgtttccc tcatgttgct    660
gtacaaaacc ttcggacgga aactgcactt gtattcccat cccatcatcc tgggctttcg    720
caagattcct atgggagtgg gcctcagtcc gtttctcttg actcagttta ctagtgccat    780
ttgttcagtg gttcgtaggg cttttccccca ctgtttggct ttcagttata tggatgatgt    840
ggtattgggg gccaagtctg tacaacatct tgagtccctt tataccgcta ttaccaattt    900
tcttttgtct ttgggtatac atttaaaccc taataaaacc aagcgatggg gttactccct    960
taacttcatg ggatatgtca ttggaagttg ggggacttta ccacaggaac atattgtgct   1020
c                                                                   1021

<210> SEQ ID NO 11
<211> LENGTH: 267
<212> TYPE: PRT
<213> ORGANISM: hepatitis B virus

<400> SEQUENCE: 11

Glu Asp Trp Gly Pro Cys Thr Glu His Gly Glu His Asn Ile Arg Ile
1               5                   10                  15

Pro Arg Thr Pro Ala Arg Val Thr Gly Gly Val Phe Leu Val Asp Lys
            20                  25                  30

Asn Pro His Asn Thr Thr Glu Ser Arg Leu Val Val Asp Phe Ser Gln
        35                  40                  45

Phe Ser Arg Gly Ser Thr Arg Val Ser Trp Pro Lys Phe Ala Val Pro
    50                  55                  60

Asn Leu Gln Ser Leu Thr Asn Leu Leu Ser Ser Asn Leu Ser Trp Leu
65                  70                  75                  80

Ser Leu Asp Val Ser Ala Ala Phe Tyr His Leu Pro Leu His Pro Ala
                85                  90                  95

Ala Met Pro His Leu Leu Val Gly Ser Ser Gly Leu Pro Arg Tyr Val
            100                 105                 110

Ala Arg Leu Ser Ser Thr Ser Arg Asn Val Asn Tyr Gln His Gly Thr
        115                 120                 125

Met Gln Asp Leu His Asp Ser Cys Ser Arg Asn Leu Tyr Val Ser Leu
    130                 135                 140

Met Leu Leu Tyr Lys Thr Phe Gly Arg Lys Leu His Leu Tyr Ser His
145                 150                 155                 160

Pro Ile Ile Leu Gly Phe Arg Lys Ile Pro Met Gly Val Gly Leu Ser
                165                 170                 175

Pro Phe Leu Leu Thr Gln Phe Thr Ser Ala Ile Cys Ser Val Val Arg
            180                 185                 190

Arg Ala Phe Pro His Cys Leu Ala Phe Ser Tyr Met Asp Asp Val Val
        195                 200                 205

Leu Gly Ala Lys Ser Val Gln His Leu Glu Ser Leu Tyr Thr Ala Ile
    210                 215                 220
```

```
Thr Asn Phe Leu Leu Ser Leu Gly Ile His Leu Asn Pro Asn Lys Thr
225                 230                 235                 240

Lys Arg Trp Gly Tyr Ser Leu Asn Phe Met Gly Tyr Val Ile Gly Ser
            245                 250                 255

Trp Gly Thr Leu Pro Gln Glu His Ile Val Leu
        260                 265
```

<210> SEQ ID NO 12
<211> LENGTH: 226
<212> TYPE: PRT
<213> ORGANISM: hepatitis B virus
<220> FEATURE:
<221> NAME/KEY: MISC_FEATURE
<222> LOCATION: (172)..(172)
<223> OTHER INFORMATION: Xaa is any amino acid

<400> SEQUENCE: 12

```
Met Glu Ser Thr Thr Ser Gly Phe Leu Gly Pro Leu Leu Val Leu Gln
1               5                   10                  15

Ala Val Phe Phe Leu Leu Thr Arg Ile Leu Thr Ile Pro Gln Ser Leu
            20                  25                  30

Asp Ser Trp Trp Thr Ser Leu Asn Phe Leu Gly Glu Ala Pro Ala Cys
        35                  40                  45

Pro Gly Gln Asn Ser Gln Ser Pro Thr Ser Asn His Ser Pro Thr Ser
50                  55                  60

Cys Pro Pro Ile Cys Pro Gly Tyr Arg Trp Met Cys Leu Arg Arg Phe
65                  70                  75                  80

Ile Ile Phe Leu Phe Ile Leu Leu Leu Cys Leu Ile Phe Leu Leu Val
                85                  90                  95

Leu Leu Asp Tyr Gln Gly Met Leu Pro Val Cys Pro Leu Leu Pro Gly
            100                 105                 110

Thr Ser Thr Thr Ser Thr Gly Pro Cys Lys Thr Cys Thr Ile Pro Ala
        115                 120                 125

Gln Gly Thr Ser Met Phe Pro Ser Cys Cys Cys Thr Lys Pro Ser Asp
130                 135                 140

Gly Asn Cys Thr Cys Ile Pro Ile Pro Ser Ser Trp Ala Phe Ala Arg
145                 150                 155                 160

Phe Leu Trp Glu Trp Ala Ser Val Arg Phe Ser Xaa Leu Ser Leu Leu
                165                 170                 175

Val Pro Phe Val Gln Trp Phe Val Gly Leu Ser Pro Thr Val Trp Leu
            180                 185                 190

Ser Val Ile Trp Met Met Trp Tyr Trp Gly Pro Ser Leu Tyr Asn Ile
        195                 200                 205

Leu Ser Pro Phe Ile Pro Leu Leu Pro Ile Phe Phe Cys Leu Trp Val
210                 215                 220

Tyr Ile
225
```

<210> SEQ ID NO 13
<211> LENGTH: 953
<212> TYPE: DNA
<213> ORGANISM: hepatitis B virus

<400> SEQUENCE: 13

```
agtcatcctc aggccatgca gtggaactcc agcacattcc accaagctct gctagatccc      60
agagtgaggg gcctatactt tcctgctggt ggctccagtt caggaacagt aaaccctgtt     120
ccgactactg cctctcccat atcgtcaatc ttctcgagga ctggggaccc tgcaccgaat     180
```

-continued

```
atggagagca ccacatcagg attcctagga cccctgctcg tgttacaggc ggggttttc      240 ttgttgacaa gaatcctcac aataccacag agtctagact cgtggtggac ttctctcaat      300
tttctagggg gagcacccgc gtgtcctggc caaaatttgc agtccccaac ctccaatcac      360
tcactaacct cttgtcctcc aatttgtcct ggttatcgct ggatgtgtct gcggcgtttt      420
atcatcttcc tcttcatcct gctgctatgc ctcatcttct tgttggttct tctggactac      480
caaggtatgt tgcccgtttg tcctctactt ccaggaacat caactaccag cacgggacca      540
tgcaagacct gcacgactcc tgctcaagga acctctatgt ttccctcttg ttgttgtaca      600
aaaccttcgg acggaaattg cacttgtatt cccatcccat catcttggc tttcgcaaga      660 ttcctatggg agtgggcctc agtccgtttc tcatggctca gtttactagt gccatttgtt      720
cagtggttcg tagggctttc ccccactgtt tggttttcag ttatgtggat gatgtggtat      780
tgggggccaa gtctgcacaa catcttgaat ccctttttac cgctattacc aattttcttt      840
tgtctttggg tatacattta aaccmtaata aaaccaaacg ttggggctat tcccttaact      900
ttatgggata tggaattgga agttggggtc ctgcccaggg aagatggcag ggg             953
```

<210> SEQ ID NO 14
<211> LENGTH: 309
<212> TYPE: PRT
<213> ORGANISM: hepatitis B virus
<220> FEATURE:
<221> NAME/KEY: MISC_FEATURE
<222> LOCATION: (288)..(288)
<223> OTHER INFORMATION: Xaa is any amino acid

<400> SEQUENCE: 14

```
Ser Ser Ser Gly His Ala Val Glu Leu Gln His Ile Pro Pro Ser Ser
1               5                   10                  15

Ala Arg Ser Gln Ser Glu Gly Pro Ile Leu Ser Cys Trp Trp Leu Gln
                20                  25                  30

Phe Arg Asn Ser Lys Pro Cys Ser Asp Tyr Cys Leu Ser His Ile Val
            35                  40                  45

Asn Leu Leu Glu Asp Trp Gly Pro Cys Thr Glu Tyr Gly Glu His His
        50                  55                  60

Ile Arg Ile Pro Arg Thr Pro Ala Arg Val Thr Gly Gly Val Phe Leu
65                  70                  75                  80

Val Asp Lys Asn Pro His Asn Thr Thr Glu Ser Arg Leu Val Val Asp
                85                  90                  95

Phe Ser Gln Phe Ser Arg Gly Ser Thr Arg Val Ser Trp Pro Lys Phe
            100                 105                 110

Ala Val Pro Asn Leu Gln Ser Leu Thr Asn Leu Leu Ser Ser Asn Leu
        115                 120                 125

Ser Trp Leu Ser Leu Asp Val Ser Ala Ala Phe Tyr His Leu Pro Leu
    130                 135                 140

His Pro Ala Ala Met Pro His Leu Leu Val Gly Ser Ser Gly Leu Pro
145                 150                 155                 160

Arg Tyr Val Ala Arg Leu Ser Ser Thr Ser Arg Asn Ile Asn Tyr Gln
                165                 170                 175

His Gly Thr Met Gln Asp Leu His Asp Ser Cys Ser Arg Asn Leu Tyr
            180                 185                 190

Val Ser Leu Leu Leu Leu Tyr Lys Thr Phe Gly Arg Lys Leu His Leu
        195                 200                 205

Tyr Ser His Pro Ile Ile Leu Gly Phe Arg Lys Ile Pro Met Gly Val
    210                 215                 220
```

```
Gly Leu Ser Pro Phe Leu Met Ala Gln Phe Thr Ser Ala Ile Cys Ser
225                 230                 235                 240

Val Val Arg Arg Ala Phe Pro His Cys Leu Val Phe Ser Tyr Val Asp
                245                 250                 255

Asp Val Val Leu Gly Ala Lys Ser Ala Gln His Leu Glu Ser Leu Phe
            260                 265                 270

Thr Ala Ile Thr Asn Phe Leu Leu Ser Leu Gly Ile His Leu Asn Xaa
        275                 280                 285

Asn Lys Thr Lys Arg Trp Gly Tyr Ser Leu Asn Phe Met Gly Tyr Gly
290                 295                 300

Ile Gly Ser Trp Gly
305

<210> SEQ ID NO 15
<211> LENGTH: 307
<212> TYPE: PRT
<213> ORGANISM: hepatitis B virus
<220> FEATURE:
<221> NAME/KEY: MISC_FEATURE
<222> LOCATION: (298)..(298)
<223> OTHER INFORMATION: Xaa is any amino acid
<220> FEATURE:
<221> NAME/KEY: MISC_FEATURE
<222> LOCATION: (300)..(300)
<223> OTHER INFORMATION: Xaa is any amino acid

<400> SEQUENCE: 15

Gln Pro Thr Pro Ile Ser Pro Pro Leu Arg Asp Ser His Pro Gln Ala
1               5                   10                  15

Met Gln Trp Asn Ser Ser Thr Phe His Gln Ala Leu Leu Asp Pro Arg
            20                  25                  30

Val Arg Gly Leu Tyr Phe Pro Ala Gly Gly Ser Ser Ser Gly Thr Val
        35                  40                  45

Asn Pro Val Pro Thr Thr Ala Ser Pro Ile Ser Ser Ile Phe Ser Arg
    50                  55                  60

Thr Gly Asp Pro Ala Pro Asn Met Glu Ser Thr Thr Ser Gly Phe Leu
65                  70                  75                  80

Gly Pro Leu Leu Val Leu Gln Ala Gly Phe Phe Leu Leu Thr Arg Ile
                85                  90                  95

Leu Thr Ile Pro Gln Ser Leu Asp Ser Trp Trp Thr Ser Leu Asn Phe
            100                 105                 110

Leu Gly Gly Ala Pro Ala Cys Pro Gly Gln Asn Leu Gln Ser Pro Thr
        115                 120                 125

Ser Asn His Ser Leu Thr Ser Cys Pro Pro Ile Cys Pro Gly Tyr Arg
    130                 135                 140

Trp Met Cys Leu Arg Arg Phe Ile Ile Phe Leu Phe Ile Leu Leu Leu
145                 150                 155                 160

Cys Leu Ile Phe Leu Leu Val Leu Leu Asp Tyr Gln Gly Met Leu Pro
                165                 170                 175

Val Cys Pro Leu Leu Pro Gly Thr Ser Thr Thr Ser Thr Gly Pro Cys
            180                 185                 190

Lys Thr Cys Thr Thr Pro Ala Gln Gly Thr Ser Met Phe Pro Ser Cys
        195                 200                 205

Cys Cys Thr Lys Pro Ser Asp Gly Asn Cys Thr Cys Ile Pro Ile Pro
    210                 215                 220

Ser Ser Trp Ala Phe Ala Arg Phe Leu Trp Glu Trp Ala Ser Val Arg
225                 230                 235                 240

Phe Ser Trp Leu Ser Leu Leu Val Pro Phe Val Gln Trp Phe Val Gly
```

```
                    245                 250                 255
Leu Ser Pro Thr Val Trp Phe Ser Val Met Trp Met Met Trp Tyr Trp
            260                 265                 270

Gly Pro Ser Leu His Asn Ile Leu Asn Pro Phe Leu Pro Leu Leu Pro
            275                 280                 285

Ile Phe Phe Cys Leu Trp Val Tyr Ile Xaa Thr Xaa Ile Lys Pro Asn
            290                 295                 300

Val Gly Ala
305

<210> SEQ ID NO 16
<211> LENGTH: 988
<212> TYPE: DNA
<213> ORGANISM: hepatitis B virus

<400> SEQUENCE: 16
ccaatcggca gtcaggaaga cagcctactc ccatctctcc acctctaaga gacagtcatc      60
ctcaggccat gcagtggaac tccagcacat tccaccaagc tctgctagat cccagagtga     120
ggggcctata cttcctgct ggtggctcca gttccggaac agtaaaccct gttccgacta      180
ctgcctctcc catatcgtca atcttctcga ggactgggga ccctgcaccg aatatggaga     240
gcaccacatc aggattccta ggaccccctgc tcgtgttaca gcggggtttt tcttgttga    300
caagaatcct cacaatacca cagagtctag actcgtggtg gacttctctc aattttctag     360
ggggagcacc cacgtgtcct ggccaaaatt tgcagtcccc aacctccaat cactcaccaa     420
cctcttgtcc tccaatttgt cctggttatc gctggatgtg tctgcggcgt tttatcatct     480
tcctcttcat cctgctgcta tgcctcatct tcttgttggt tcttctggac taccaaggta     540
tgttgcccgt ttgtcctcta cttccaggaa catcaactac cagcacggga ccatgcaaga     600
cctgcacgac tcctgctcaa ggaacctcta tgtttccctc ttgttgctgt acaaaacctt     660
cggacggaaa ttgcacttgt attcccatcc catcatcttg gctttcgca agattcctat      720
gggagtgggc ctcagtccgt ttctcctggc tcagtttact agtgccattt gttcagtggt     780
tcgtagggct ttcccccact gtttggcttt cagtatatg gatgatgtgg tattgggggc      840
caagtctgta caacatcttg aatcccttttt taccgctgtt accaatttc ttttgtcttt      900
gggtatacat ttaaaccta ctaaaactaa acgttggggc tactccctta acttcatggg      960
atatgtaatt ggaagttggg gtaccttg                                          988

<210> SEQ ID NO 17
<211> LENGTH: 258
<212> TYPE: PRT
<213> ORGANISM: hepatitis B virus

<400> SEQUENCE: 17

Glu Asp Trp Gly Pro Cys Thr Glu Tyr Gly Glu His His Ile Arg Ile
1               5                   10                  15

Pro Arg Thr Pro Ala Arg Val Thr Gly Gly Val Phe Leu Val Asp Lys
            20                  25                  30

Asn Pro His Asn Thr Thr Glu Ser Arg Leu Val Val Asp Phe Ser Gln
        35                  40                  45

Phe Ser Arg Gly Ser Thr His Val Ser Trp Pro Lys Phe Ala Val Pro
    50                  55                  60

Asn Leu Gln Ser Leu Thr Asn Leu Leu Ser Ser Asn Leu Ser Trp Leu
65                  70                  75                  80

Ser Leu Asp Val Ser Ala Ala Phe Tyr His Leu Pro Leu His Pro Ala
```

```
                     85                  90                  95
Ala Met Pro His Leu Leu Val Gly Ser Ser Gly Leu Pro Arg Tyr Val
            100                 105                 110

Ala Arg Leu Ser Ser Thr Ser Arg Asn Ile Asn Tyr Gln His Gly Thr
            115                 120                 125

Met Gln Asp Leu His Asp Ser Cys Ser Arg Asn Leu Tyr Val Ser Leu
            130                 135                 140

Leu Leu Leu Tyr Lys Thr Phe Gly Arg Lys Leu His Leu Tyr Ser His
145                 150                 155                 160

Pro Ile Ile Leu Gly Phe Arg Lys Ile Pro Met Gly Val Gly Leu Ser
                    165                 170                 175

Pro Phe Leu Leu Ala Gln Phe Thr Ser Ala Ile Cys Ser Val Val Arg
            180                 185                 190

Arg Ala Phe Pro His Cys Leu Ala Phe Ser Tyr Met Asp Asp Val Val
            195                 200                 205

Leu Gly Ala Lys Ser Val Gln His Leu Glu Ser Leu Phe Thr Ala Val
            210                 215                 220

Thr Asn Phe Leu Leu Ser Leu Gly Ile His Leu Asn Pro Thr Lys Thr
225                 230                 235                 240

Lys Arg Trp Gly Tyr Ser Leu Asn Phe Met Gly Tyr Val Ile Gly Ser
                    245                 250                 255

Trp Gly

<210> SEQ ID NO 18
<211> LENGTH: 226
<212> TYPE: PRT
<213> ORGANISM: hepatitis B virus

<400> SEQUENCE: 18

Met Glu Ser Thr Thr Ser Gly Phe Leu Gly Pro Leu Leu Val Leu Gln
1               5                   10                  15

Ala Gly Phe Phe Leu Leu Thr Arg Ile Leu Thr Ile Pro Gln Ser Leu
                20                  25                  30

Asp Ser Trp Trp Thr Ser Leu Asn Phe Leu Gly Gly Ala Pro Thr Cys
            35                  40                  45

Pro Gly Gln Asn Leu Gln Ser Pro Thr Ser Asn His Ser Pro Thr Ser
        50                  55                  60

Cys Pro Pro Ile Cys Pro Gly Tyr Arg Trp Met Cys Leu Arg Arg Phe
65                  70                  75                  80

Ile Ile Phe Leu Phe Ile Leu Leu Leu Cys Leu Ile Phe Leu Leu Val
                    85                  90                  95

Leu Leu Asp Tyr Gln Gly Met Leu Pro Val Cys Pro Leu Leu Pro Gly
            100                 105                 110

Thr Ser Thr Thr Ser Thr Gly Pro Cys Lys Thr Cys Thr Thr Pro Ala
            115                 120                 125

Gln Gly Thr Ser Met Phe Pro Ser Cys Cys Cys Thr Lys Pro Ser Asp
            130                 135                 140

Gly Asn Cys Thr Cys Ile Pro Ile Pro Ser Ser Trp Ala Phe Ala Arg
145                 150                 155                 160

Phe Leu Trp Glu Trp Ala Ser Val Arg Phe Ser Trp Leu Ser Leu Leu
                    165                 170                 175

Val Pro Phe Val Gln Trp Phe Val Gly Leu Ser Pro Thr Val Trp Leu
            180                 185                 190

Ser Val Ile Trp Met Met Trp Tyr Trp Gly Pro Ser Leu Tyr Asn Ile
            195                 200                 205
```

```
Leu Asn Pro Phe Leu Pro Leu Leu Pro Ile Phe Phe Cys Leu Trp Val
    210                 215                 220

Tyr Ile
225
```

<210> SEQ ID NO 19
<211> LENGTH: 1043
<212> TYPE: DNA
<213> ORGANISM: hepatitis B virus

<400> SEQUENCE: 19

```
tccgcctcct gcctccacca atcgccagtc aggaaggcaa cctacccgc tctctccacc      60
tttgagagac actcatcctc aggccgtgca gtggaactcc acaaccttcc accaaactct    120
gcaagatccc agagtgaggg gcctgtatct ccctgctggt ggctccagtt caggaacagc    180
aaaccctgtt ccgactactg cctctcgctt atcgtcaatc ttctcgagga ttggggaccc    240
tgcgctgaac atggagaaca tcacatcagg actcctagga cccttctcg tgttacaggc     300
ggggttttc ttgttgacaa gaatcctcac aataccgcag agtctagact cgtggtggac     360
ttctctcagt tttctagggg gaactaccgt gtgtcttggc caaaattcgc ggtccccaac    420
ctccaatcac tcaccaacct cctgtcctcc gacttgtcct ggttatcgct ggatgtatct    480
gcggcgtttt atcatattcc tcttcatcct gctgctatgc ctcatcttct gttggttct    540
tctggactat caaggtatgt tgcccgtttg tcctctaatt ccaggatcct caaccaccag    600
cacgggaaca tgccgaacct gcacgactcc tgctcaagga acctctatgt atccctcctg    660
ttgctgtacc aaaccttcgg acggaaattg cacctgtatt cccatcccat catcttgggc    720
tttcggaaaa ttcctatggg agtgggcctc agcccgtttc tcctggctca gtttactagt    780
gccatttgtt cagtggttcg tagggctttc ccccactgtt tggctttcag ttatatggat    840
gatgtggtat tgggggccaa gtctgtacag catcttgagt cccttttac cgctgttacc    900
aatttttcttt tgtctttggg tatacattta accctaaca aaacaaagag atggggttac    960
tctctaaatt ttatgggcta tgtcattgga agttatgggt ccttgccaca agaacacatt   1020
atactaaaaa tcaaagattg ttt                                           1043
```

<210> SEQ ID NO 20
<211> LENGTH: 258
<212> TYPE: PRT
<213> ORGANISM: hepatitis B virus

<400> SEQUENCE: 20

```
Glu Asp Trp Gly Pro Cys Ala Glu His Gly Glu His His Ile Arg Thr
1               5                   10                  15

Pro Arg Thr Pro Ser Arg Val Thr Gly Gly Val Phe Leu Val Asp Lys
            20                  25                  30

Asn Pro His Asn Thr Ala Glu Ser Arg Leu Val Val Asp Phe Ser Gln
        35                  40                  45

Phe Ser Arg Gly Asn Tyr Arg Val Ser Trp Pro Lys Phe Ala Val Pro
    50                  55                  60

Asn Leu Gln Ser Leu Thr Asn Leu Leu Ser Ser Asp Leu Ser Trp Leu
65                  70                  75                  80

Ser Leu Asp Val Ser Ala Ala Phe Tyr His Ile Pro Leu His Pro Ala
                85                  90                  95

Ala Met Pro His Leu Leu Val Gly Ser Ser Gly Leu Ser Arg Tyr Val
            100                 105                 110
```

```
Ala Arg Leu Ser Ser Asn Ser Arg Ile Leu Asn His Gln His Gly Asn
        115                 120                 125

Met Pro Asn Leu His Asp Ser Cys Ser Arg Asn Leu Tyr Val Ser Leu
    130                 135                 140

Leu Leu Leu Tyr Gln Thr Phe Gly Arg Lys Leu His Leu Tyr Ser His
145                 150                 155                 160

Pro Ile Ile Leu Gly Phe Arg Lys Ile Pro Met Gly Val Gly Leu Ser
                165                 170                 175

Pro Phe Leu Leu Ala Gln Phe Thr Ser Ala Ile Cys Ser Val Val Arg
            180                 185                 190

Arg Ala Phe Pro His Cys Leu Ala Phe Ser Tyr Met Asp Asp Val Val
        195                 200                 205

Leu Gly Ala Lys Ser Val Gln His Leu Glu Ser Leu Phe Thr Ala Val
    210                 215                 220

Thr Asn Phe Leu Leu Ser Leu Gly Ile His Leu Thr Pro Asn Lys Thr
225                 230                 235                 240

Lys Arg Trp Gly Tyr Ser Leu Asn Phe Met Gly Tyr Val Ile Gly Ser
                245                 250                 255

Tyr Gly

<210> SEQ ID NO 21
<211> LENGTH: 226
<212> TYPE: PRT
<213> ORGANISM: hepatitis B virus

<400> SEQUENCE: 21

Met Glu Asn Ile Thr Ser Gly Leu Leu Gly Pro Leu Leu Val Leu Gln
1               5                   10                  15

Ala Gly Phe Phe Leu Leu Thr Arg Ile Leu Thr Ile Pro Gln Ser Leu
            20                  25                  30

Asp Ser Trp Trp Thr Ser Leu Ser Phe Leu Gly Gly Thr Thr Val Cys
        35                  40                  45

Leu Gly Gln Asn Ser Arg Ser Pro Thr Ser Asn His Ser Pro Thr Ser
    50                  55                  60

Cys Pro Pro Thr Cys Pro Gly Tyr Arg Trp Met Tyr Leu Arg Arg Phe
65                  70                  75                  80

Ile Ile Phe Leu Phe Ile Leu Leu Cys Leu Ile Phe Leu Leu Val
                85                  90                  95

Leu Leu Asp Tyr Gln Gly Met Leu Pro Val Cys Pro Leu Ile Pro Gly
                100                 105                 110

Ser Ser Thr Thr Ser Thr Gly Thr Cys Arg Thr Cys Thr Thr Pro Ala
            115                 120                 125

Gln Gly Thr Ser Met Tyr Pro Ser Cys Cys Cys Thr Lys Pro Ser Asp
        130                 135                 140

Gly Asn Cys Thr Cys Ile Pro Ile Pro Ser Ser Trp Ala Phe Gly Lys
145                 150                 155                 160

Phe Leu Trp Glu Trp Ala Ser Ala Arg Phe Ser Trp Leu Ser Leu Leu
                165                 170                 175

Val Pro Phe Val Gln Trp Phe Val Gly Leu Ser Pro Thr Val Trp Leu
            180                 185                 190

Ser Val Ile Trp Met Met Trp Tyr Trp Gly Pro Ser Leu Tyr Ser Ile
        195                 200                 205

Leu Ser Pro Phe Leu Pro Leu Leu Pro Ile Phe Phe Cys Leu Trp Val
    210                 215                 220

Tyr Ile
```

<210> SEQ ID NO 22
<211> LENGTH: 1027
<212> TYPE: DNA
<213> ORGANISM: hepatitis B virus

<400> SEQUENCE: 22

```
cgcctcctgc ctccaccaat cgccagtcag gaaggcagcc gaccccactg tctccacctt      60
tgagagacac tcatcctcag gccgtgcagt ggaactccac aaccttccac caaactctgc     120
aagatcccag agtgagaggc ctgtatttcc ctgctggtgg ctccagttca ggaacagtaa     180
accctgttcc gaccactgcc tctcccttat cgtcaatctt ctcgaggatt ggggaccctg     240
cgctgaacat ggagaacatc acatcaggat tcctaggacc ccttctcgtg ttacaggcgg     300
ggttttcctt gttgacaaga atcctcacaa taccgcagag tctagactcg tggtggactt     360
ctctcagttt tctaggggaa accaccgtgt gtcttggcca aaattcgcag tccccaacct     420
ccaatcactc accaacctcc tgtcctccaa cttgtcctgg ttatcgctgg atgtgtctgc     480
ggcgttttat catattcctc ttcatcctgc tgctatgcct catcttcttg ttggttcttc     540
tggactatca aggtatgttg cccgtttgtc ctctaattcc aggatcctca accaccagca     600
cgggaccatg ccgaacctgc acgactcctg ctcaaggaac ctctatgtat ccctcctgtt     660
gctgtaccaa accttcggac ggaaattgca cctgtattcc catcccatca tcttgggctt     720
tcgcaaaatt cctatgggag tgggcctcag cccgtttctc atggctcagt ttactagtgc     780
catttgttca gtggttcgta gggctttccc ccactgtttg gctttcagtt atgtggatga     840
tgtggtattg ggggccaagt ctgtatcgca tcttgagtcc cttttaccg ctgttaccaa     900
ttttcttttg tctttgggta tacatttaaa ccctaacaaa acgaaagat gggggttactc     960
tttaaatttt atggggtatg ttattggatg ttatgggtcc ttgccacaag aacacatcgt    1020
acaaaaa                                                               1027
```

<210> SEQ ID NO 23
<211> LENGTH: 264
<212> TYPE: PRT
<213> ORGANISM: hepatitis B virus

<400> SEQUENCE: 23

```
Glu Asp Trp Gly Pro Cys Ala Glu His Gly Glu His His Ile Arg Ile
1               5                   10                  15

Pro Arg Thr Pro Ser Arg Val Thr Gly Gly Val Phe Leu Val Asp Lys
            20                  25                  30

Asn Pro His Asn Thr Ala Glu Ser Arg Leu Val Val Asp Phe Ser Gln
        35                  40                  45

Phe Ser Arg Gly Asn His Arg Val Ser Trp Pro Lys Phe Ala Val Pro
    50                  55                  60

Asn Leu Gln Ser Leu Thr Asn Leu Leu Ser Ser Asn Leu Ser Trp Leu
65                  70                  75                  80

Ser Leu Asp Val Ser Ala Ala Phe Tyr His Ile Pro Leu His Pro Ala
                85                  90                  95

Ala Met Pro His Leu Leu Val Gly Ser Ser Gly Leu Ser Arg Tyr Val
            100                 105                 110

Ala Arg Leu Ser Ser Asn Ser Arg Ile Leu Asn His Gln His Gly Thr
        115                 120                 125

Met Pro Asn Leu His Asp Ser Cys Ser Arg Asn Leu Tyr Val Ser Leu
    130                 135                 140
```

Leu Leu Leu Tyr Gln Thr Phe Gly Arg Lys Leu His Leu Tyr Ser His
145                 150                 155                 160

Pro Ile Ile Leu Gly Phe Arg Lys Ile Pro Met Gly Val Gly Leu Ser
                165                 170                 175

Pro Phe Leu Met Ala Gln Phe Thr Ser Ala Ile Cys Ser Val Val Arg
            180                 185                 190

Arg Ala Phe Pro His Cys Leu Ala Phe Ser Tyr Val Asp Asp Val Val
        195                 200                 205

Leu Gly Ala Lys Ser Val Ser His Leu Glu Ser Leu Phe Thr Ala Val
    210                 215                 220

Thr Asn Phe Leu Leu Ser Leu Gly Ile His Leu Asn Pro Asn Lys Thr
225                 230                 235                 240

Lys Arg Trp Gly Tyr Ser Leu Asn Phe Met Gly Tyr Val Ile Gly Cys
                245                 250                 255

Tyr Gly Ser Leu Pro Gln Glu His
                260

<210> SEQ ID NO 24
<211> LENGTH: 226
<212> TYPE: PRT
<213> ORGANISM: hepatitis B virus

<400> SEQUENCE: 24

Met Glu Asn Ile Thr Ser Gly Phe Leu Gly Pro Leu Leu Val Leu Gln
1                   5                   10                  15

Ala Gly Phe Phe Leu Leu Thr Arg Ile Leu Thr Ile Pro Gln Ser Leu
                20                  25                  30

Asp Ser Trp Trp Thr Ser Leu Ser Phe Leu Gly Glu Thr Thr Val Cys
            35                  40                  45

Leu Gly Gln Asn Ser Gln Ser Pro Thr Ser Asn His Ser Pro Thr Ser
    50                  55                  60

Cys Pro Pro Thr Cys Pro Gly Tyr Arg Trp Met Cys Leu Arg Arg Phe
65                  70                  75                  80

Ile Ile Phe Leu Phe Ile Leu Leu Leu Cys Leu Ile Phe Leu Leu Val
                85                  90                  95

Leu Leu Asp Tyr Gln Gly Met Leu Pro Val Cys Pro Leu Ile Pro Gly
                100                 105                 110

Ser Ser Thr Thr Ser Thr Gly Pro Cys Arg Thr Cys Thr Thr Pro Ala
            115                 120                 125

Gln Gly Thr Ser Met Tyr Pro Ser Cys Cys Cys Thr Lys Pro Ser Asp
    130                 135                 140

Gly Asn Cys Thr Cys Ile Pro Ile Pro Ser Ser Trp Ala Phe Ala Lys
145                 150                 155                 160

Phe Leu Trp Glu Trp Gly Ser Ala Arg Phe Ser Trp Leu Ser Leu Leu
                165                 170                 175

Val Pro Phe Val Gln Trp Phe Val Gly Leu Ser Pro Thr Val Trp Leu
                180                 185                 190

Ser Val Met Trp Met Met Trp Tyr Trp Gly Pro Ser Leu Tyr Arg Ile
                195                 200                 205

Leu Ser Pro Phe Leu Pro Leu Leu Pro Ile Phe Phe Cys Leu Trp Val
    210                 215                 220

Tyr Ile
225

<210> SEQ ID NO 25

```
<211> LENGTH: 560
<212> TYPE: DNA
<213> ORGANISM: hepatitis B virus

<400> SEQUENCE: 25
caacttgtcc tggttatcgc tggatgtgtc tgcggcgttt tatcatattc ctcttcatcc      60
tgctgctatg cctcatcttc ttgttggttc ttctggacta tcgaggtatg ttgcccgttt     120
gtcctctact tccaggatct tcaaccacca gcacgggtcc atgcagaacc tgcacgactc     180
ctgctcaagg aacctctatg tatccctcat gttgctgtac aaaccttcg gacggaaatt      240 gcacctgtat tccatcccca tcatcctggg ctttcggaaa attcctatgg gagtgggcct     300
cagcccgttt ctcatggctc agttactag tgccatttgt tcagtggttc gtagggcttt      360
cccccattgt ttggctttca gttatgtgga tgatgtggta ttgggggcca agtctgtatc     420
gcatcttgag tcccttttta ccgctgttac caatttttctt ttgtctctgg gtatacattt    480
aaaccctcac aaaacaaaaa gatggggtta ctctttacat ttcatgggct atgtcatcgg     540
atgttatggg tctttgccac                                                560

<210> SEQ ID NO 26
<211> LENGTH: 186
<212> TYPE: PRT
<213> ORGANISM: hepatitis B virus

<400> SEQUENCE: 26

Asn Leu Ser Trp Leu Ser Leu Asp Val Ser Ala Ala Phe Tyr His Ile
1               5                   10                  15

Pro Leu His Pro Ala Ala Met Pro His Leu Leu Val Gly Ser Ser Gly
            20                  25                  30

Leu Ser Arg Tyr Val Ala Arg Leu Ser Ser Thr Ser Arg Ile Phe Asn
        35                  40                  45

His Gln His Gly Ser Met Gln Asn Leu His Asp Ser Cys Ser Arg Asn
    50                  55                  60

Leu Tyr Val Ser Leu Met Leu Leu Tyr Gln Thr Phe Gly Arg Lys Leu
65                  70                  75                  80

His Leu Tyr Ser His Pro Ile Ile Leu Gly Phe Arg Lys Ile Pro Met
                85                  90                  95

Gly Val Gly Leu Ser Pro Phe Leu Met Ala Gln Phe Thr Ser Ala Ile
            100                 105                 110

Cys Ser Val Val Arg Arg Ala Phe Pro His Cys Leu Ala Phe Ser Tyr
        115                 120                 125

Val Asp Asp Val Val Leu Gly Ala Lys Ser Val Ser His Leu Glu Ser
    130                 135                 140

Leu Phe Thr Ala Val Thr Asn Phe Leu Leu Ser Leu Gly Ile His Leu
145                 150                 155                 160

Asn Pro His Lys Thr Lys Arg Trp Gly Tyr Ser Leu His Phe Met Gly
                165                 170                 175

Tyr Val Ile Gly Cys Tyr Gly Ser Leu Pro
            180                 185

<210> SEQ ID NO 27
<211> LENGTH: 160
<212> TYPE: PRT
<213> ORGANISM: hepatitis B virus
<220> FEATURE:
<221> NAME/KEY: MISC_FEATURE
<222> LOCATION: (160)..(160)
<223> OTHER INFORMATION: Xaa is any amino acid
```

<400> SEQUENCE: 27

```
Thr Cys Pro Gly Tyr Arg Trp Met Cys Leu Arg Arg Phe Ile Ile Phe
1               5                   10                  15
Leu Phe Ile Leu Leu Leu Cys Leu Ile Phe Leu Leu Val Leu Leu Asp
            20                  25                  30
Tyr Arg Gly Met Leu Pro Val Cys Pro Leu Leu Pro Gly Ser Ser Thr
        35                  40                  45
Thr Ser Thr Gly Pro Cys Arg Thr Cys Thr Thr Pro Ala Gln Gly Thr
50                  55                  60
Ser Met Tyr Pro Ser Cys Cys Thr Lys Pro Ser Asp Gly Asn Cys
65                  70                  75                  80
Thr Cys Ile Pro Ile Pro Ser Ser Trp Ala Phe Gly Lys Phe Leu Trp
                85                  90                  95
Glu Trp Ala Ser Ala Arg Phe Ser Trp Leu Ser Leu Leu Val Pro Phe
            100                 105                 110
Val Gln Trp Phe Val Gly Leu Ser Pro Ile Val Trp Leu Ser Val Met
        115                 120                 125
Trp Met Met Trp Tyr Trp Gly Pro Ser Leu Tyr Arg Ile Leu Ser Pro
130                 135                 140
Phe Leu Pro Leu Leu Pro Ile Phe Phe Cys Leu Trp Val Tyr Ile Xaa
145                 150                 155                 160
```

<210> SEQ ID NO 28
<211> LENGTH: 1029
<212> TYPE: DNA
<213> ORGANISM: hepatitis B virus

<400> SEQUENCE: 28

```
cgcctcctcc tgcctccacc atcggcagtc aggaagaaag cctactccca tctctccacc      60
tctaagagac agtcatcctc aggccatgca gtggaactcc agcacattcc accaagctct     120
gctagatccc aragtgagrg cctatactt tcctgctggt ggctccagtt ccggaacagt     180
aaaccctgtt ccgactactg cctctcccat atcgtcaatc ttctcgagga ctggggaccc     240
tgcaccgaat atggagagca acatcagg attcctagga cccctgctcg tgttacaggc     300
ggggttttc ttgttgacaa gaatcctcac ataccacag agtctagact cgtggtggac     360
ttctctcaat tttctagggg gagcaccca gtgtcctggc caaatttgc agtccccaac     420
ctccaatcac tcaccaacct cttgtcctcc aatttgtcct ggttatcgct ggatgtgtct     480
gcggcgtttt atcatcttcc tcttcatcct gctgctatgc ctcatcttct tgtkggttct     540
tctggactac caaggtatgt tgcccgtttg tcctctactt ccaggaacat caactaccag     600
cacgggacca tgcaagacct gcacgattcc tgctcaagga acctctatgt ttccctcttg     660
ttgctgtaca aaaccttcgg acggaaattg cacttgtatt cccatcccat catcttgggc     720
tttcgcaaga ttcctatggg agtgggcctc agtccgtttc tcctggctca gtttactagt     780
gccatttgtt cagtggttcg tagggctttc ccccactgtt tggctttcag ttatatggat     840
gatgtggtat tgggggccaa gtctgtacaa catcttgaat ccctttttac cgctgttacc     900
aattttcttt tgtctttggg tatacattta aaccctacta aaactaaacg ttggggctac     960
tcccttaact tcatgggata tgtaattgga agttggggta ccttaccaca ggaacatatt    1020
gtacacaaa                                                            1029
```

<210> SEQ ID NO 29
<211> LENGTH: 268
<212> TYPE: PRT

<213> ORGANISM: hepatitis B virus

<400> SEQUENCE: 29

Glu Asp Trp Gly Pro Cys Thr Glu Tyr Gly Glu His Asn Ile Arg Ile
1               5                   10                  15

Pro Arg Thr Pro Ala Arg Val Thr Gly Gly Val Phe Leu Val Asp Lys
            20                  25                  30

Asn Pro His Asn Thr Thr Glu Ser Arg Leu Val Val Asp Phe Ser Gln
        35                  40                  45

Phe Ser Arg Gly Ser Thr His Val Ser Trp Pro Lys Phe Ala Val Pro
    50                  55                  60

Asn Leu Gln Ser Leu Thr Asn Leu Leu Ser Ser Asn Leu Ser Trp Leu
65                  70                  75                  80

Ser Leu Asp Val Ser Ala Ala Phe Tyr His Leu Pro Leu His Pro Ala
                85                  90                  95

Ala Met Pro His Leu Leu Val Gly Ser Ser Gly Leu Pro Arg Tyr Val
            100                 105                 110

Ala Arg Leu Ser Ser Thr Ser Arg Asn Ile Asn Tyr Gln His Gly Thr
        115                 120                 125

Met Gln Asp Leu His Asp Ser Cys Ser Arg Asn Leu Tyr Val Ser Leu
    130                 135                 140

Leu Leu Leu Tyr Lys Thr Phe Gly Arg Lys Leu His Leu Tyr Ser His
145                 150                 155                 160

Pro Ile Ile Leu Gly Phe Arg Lys Ile Pro Met Gly Val Gly Leu Ser
                165                 170                 175

Pro Phe Leu Leu Ala Gln Phe Thr Ser Ala Ile Cys Ser Val Val Arg
            180                 185                 190

Arg Ala Phe Pro His Cys Leu Ala Phe Ser Tyr Met Asp Asp Val Val
        195                 200                 205

Leu Gly Ala Lys Ser Val Gln His Leu Glu Ser Leu Phe Thr Ala Val
    210                 215                 220

Thr Asn Phe Leu Leu Ser Leu Gly Ile His Leu Asn Pro Thr Lys Thr
225                 230                 235                 240

Lys Arg Trp Gly Tyr Ser Leu Asn Phe Met Gly Tyr Val Ile Gly Ser
                245                 250                 255

Trp Gly Thr Leu Pro Gln Glu His Ile Val His Lys
            260                 265

<210> SEQ ID NO 30
<211> LENGTH: 226
<212> TYPE: PRT
<213> ORGANISM: hepatitis B virus
<220> FEATURE:
<221> NAME/KEY: MISC_FEATURE
<222> LOCATION: (95)..(95)
<223> OTHER INFORMATION: Xaa is any amino acid

<400> SEQUENCE: 30

Met Glu Ser Thr Thr Ser Gly Phe Leu Gly Pro Leu Leu Val Leu Gln
1               5                   10                  15

Ala Gly Phe Phe Leu Leu Thr Arg Ile Leu Thr Ile Pro Gln Ser Leu
            20                  25                  30

Asp Ser Trp Trp Thr Ser Leu Asn Phe Leu Gly Gly Ala Pro Thr Cys
        35                  40                  45

Pro Gly Gln Asn Leu Gln Ser Pro Thr Ser Asn His Ser Pro Thr Ser
    50                  55                  60

Cys Pro Pro Ile Cys Pro Gly Tyr Arg Trp Met Cys Leu Arg Arg Phe

```
                65                  70                  75                  80
Ile Ile Phe Leu Phe Ile Leu Leu Cys Leu Ile Phe Leu Xaa Val
                    85                  90                  95

Leu Leu Asp Tyr Gln Gly Met Leu Pro Val Cys Pro Leu Leu Pro Gly
                100                 105                 110

Thr Ser Thr Thr Ser Thr Gly Pro Cys Lys Thr Cys Thr Ile Pro Ala
            115                 120                 125

Gln Gly Thr Ser Met Phe Pro Ser Cys Cys Thr Lys Pro Ser Asp
        130                 135                 140

Gly Asn Cys Thr Cys Ile Pro Ile Pro Ser Ser Trp Ala Phe Ala Arg
145                 150                 155                 160

Phe Leu Trp Glu Trp Ala Ser Val Arg Phe Ser Trp Leu Ser Leu Leu
                165                 170                 175

Val Pro Phe Val Gln Trp Phe Val Gly Leu Ser Pro Thr Val Trp Leu
                180                 185                 190

Ser Val Ile Trp Met Met Trp Tyr Trp Gly Pro Ser Leu Tyr Asn Ile
                195                 200                 205

Leu Asn Pro Phe Leu Pro Leu Leu Pro Ile Phe Phe Cys Leu Trp Val
            210                 215                 220

Tyr Ile
225

<210> SEQ ID NO 31
<211> LENGTH: 1035
<212> TYPE: DNA
<213> ORGANISM: hepatitis B virus

<400> SEQUENCE: 31
ctcctcctgc ctccaccaat cggcagtcag gaagacagcc tacacccatc tctccacctc      60
taagagacag tcatcctcag gccatgcagt ggaactccag cacattccac caagctctgc     120
tagatcccag agtgaggggc ctatactttc ctgctggtgg ctccagttca ggaacagtaa     180
accctgttcc gactactgcc tctcccatat cgtcaatctt ctcgaggact ggggaccctg     240
caccgaatat ggagagcacc acatcaggat tcctaggacc cctgctcgtg ttacaggcgg     300 ggttttctt gttgacaaga atcctcacaa taccacagag tctagactcg tggtggactt     360
ctctcaattt tctaggggga gcacccacgt gtcctggcca aaatttgcag tccccaacct     420
ccaatcactc accaacctct tgtcctccaa tttgtcctgg ttatcgctgg atgtgtctgc     480
ggcgttttat catcttcctc ttcatcctgc tgctatgcct catcttcttg ttggttcttc     540
tggactacca aggtatgttg cccgtttgtc ctctacttcc aggaacatca actaccagca     600
cgggaccatg caagacctgc acgattcctg ctcaaggaac ctctatgttt ccctcttgtt     660
gctgtacaaa accttcggac ggaaattgca cttgtattcc catcccatca tcttgggctt     720
tcgcaagatt cctatgggag tgggcctcag tccgtttctc ctggctcagt ttactagtgc     780
catttgttca gtggttcgta gggctttccc ccactgtttg gctttcagtt atatggatga     840
tgtggtattg gggccaagtc tgtacaacat cttgaatccc ttttttaccg ctgttaccaa     900 ttttctttg tctttgggta tacatttaaa ccctrctaaa accaaacgtt ggggttactc     960
ccttaacttc atgggatatg taattggaag ttggggtacc ttaccacagg aacatattgt    1020
acacaaaatc aaaca                                                    1035

<210> SEQ ID NO 32
<211> LENGTH: 344
<212> TYPE: PRT
```

<213> ORGANISM: hepatitis B virus
<220> FEATURE:
<221> NAME/KEY: MISC_FEATURE
<222> LOCATION: (312)..(312)
<223> OTHER INFORMATION: Xaa is any amino acid

<400> SEQUENCE: 32

```
Ser Ser Cys Leu His Gln Ser Ala Val Arg Lys Thr Ala Tyr Thr His
1               5                   10                  15
Leu Ser Thr Ser Lys Arg Gln Ser Ser Gly His Ala Val Glu Leu
            20                  25                  30
Gln His Ile Pro Pro Ser Ser Ala Arg Ser Gln Ser Glu Gly Pro Ile
                35                  40                  45
Leu Ser Cys Trp Trp Leu Gln Phe Arg Asn Ser Lys Pro Cys Ser Asp
50                  55                  60
Tyr Cys Leu Ser His Ile Val Asn Leu Leu Glu Asp Trp Gly Pro Cys
65                  70                  75                  80
Thr Glu Tyr Gly Glu His His Ile Arg Ile Pro Arg Thr Pro Ala Arg
                85                  90                  95
Val Thr Gly Gly Val Phe Leu Val Asp Lys Asn Pro His Asn Thr Thr
            100                 105                 110
Glu Ser Arg Leu Val Val Asp Phe Ser Gln Phe Ser Arg Gly Ser Thr
        115                 120                 125
His Val Ser Trp Pro Lys Phe Ala Val Pro Asn Leu Gln Ser Leu Thr
130                 135                 140
Asn Leu Leu Ser Ser Asn Leu Ser Trp Leu Ser Leu Asp Val Ser Ala
145                 150                 155                 160
Ala Phe Tyr His Leu Pro Leu His Pro Ala Ala Met Pro His Leu Leu
                165                 170                 175
Val Gly Ser Ser Gly Leu Pro Arg Tyr Val Ala Arg Leu Ser Ser Thr
            180                 185                 190
Ser Arg Asn Ile Asn Tyr Gln His Gly Thr Met Gln Asp Leu His Asp
        195                 200                 205
Ser Cys Ser Arg Asn Leu Tyr Val Ser Leu Leu Leu Leu Tyr Lys Thr
210                 215                 220
Phe Gly Arg Lys Leu His Leu Tyr Ser His Pro Ile Ile Leu Gly Phe
225                 230                 235                 240
Arg Lys Ile Pro Met Gly Val Gly Leu Ser Pro Phe Leu Leu Ala Gln
                245                 250                 255
Phe Thr Ser Ala Ile Cys Ser Val Val Arg Arg Ala Phe Pro His Cys
            260                 265                 270
Leu Ala Phe Ser Tyr Met Asp Asp Val Val Leu Gly Ala Lys Ser Val
        275                 280                 285
Gln His Leu Glu Ser Leu Phe Thr Ala Val Thr Asn Phe Leu Leu Ser
290                 295                 300
Leu Gly Ile His Leu Asn Pro Xaa Lys Thr Lys Arg Trp Gly Tyr Ser
305                 310                 315                 320
Leu Asn Phe Met Gly Tyr Val Ile Gly Ser Trp Gly Thr Leu Pro Gln
                325                 330                 335
Glu His Ile Val His Lys Ile Lys
            340
```

<210> SEQ ID NO 33
<211> LENGTH: 344
<212> TYPE: PRT
<213> ORGANISM: hepatitis B virus
<220> FEATURE:

```
<221> NAME/KEY: MISC_FEATURE
<222> LOCATION: (309)..(309)
<223> OTHER INFORMATION: Xaa is any amino acid
<220> FEATURE:
<221> NAME/KEY: MISC_FEATURE
<222> LOCATION: (327)..(327)
<223> OTHER INFORMATION: Xaa is any amino acid

<400> SEQUENCE: 33
```

Pro Pro Ala Ser Thr Asn Arg Gln Ser Gly Arg Gln Pro Thr Pro Ile
1               5                   10                  15

Ser Pro Pro Leu Arg Asp Ser His Pro Gln Ala Met Gln Trp Asn Ser
            20                  25                  30

Ser Thr Phe His Gln Ala Leu Leu Asp Pro Arg Val Arg Gly Leu Tyr
        35                  40                  45

Phe Pro Ala Gly Gly Ser Ser Gly Thr Val Asn Pro Val Pro Thr
    50                  55                  60

Thr Ala Ser Pro Ile Ser Ser Ile Phe Ser Arg Thr Gly Asp Pro Ala
65                  70                  75                  80

Pro Asn Met Glu Ser Thr Thr Ser Gly Phe Leu Gly Pro Leu Leu Val
                85                  90                  95

Leu Gln Ala Gly Phe Phe Leu Leu Thr Arg Ile Leu Thr Ile Pro Gln
            100                 105                 110

Ser Leu Asp Ser Trp Trp Thr Ser Leu Asn Phe Leu Gly Gly Ala Pro
        115                 120                 125

Thr Cys Pro Gly Gln Asn Leu Gln Ser Pro Thr Ser Asn His Ser Pro
130                 135                 140

Thr Ser Cys Pro Pro Ile Cys Pro Gly Tyr Arg Trp Met Cys Leu Arg
145                 150                 155                 160

Arg Phe Ile Ile Phe Leu Phe Ile Leu Leu Leu Cys Leu Ile Phe Leu
                165                 170                 175

Leu Val Leu Leu Asp Tyr Gln Gly Met Leu Pro Val Cys Pro Leu Leu
            180                 185                 190

Pro Gly Thr Ser Thr Thr Ser Thr Gly Pro Cys Lys Thr Cys Thr Ile
        195                 200                 205

Pro Ala Gln Gly Thr Ser Met Phe Pro Ser Cys Cys Cys Thr Lys Pro
210                 215                 220

Ser Asp Gly Asn Cys Thr Cys Ile Pro Ile Pro Ser Ser Trp Ala Phe
225                 230                 235                 240

Ala Arg Phe Leu Trp Glu Trp Ala Ser Val Arg Phe Ser Trp Leu Ser
                245                 250                 255

Leu Leu Val Pro Phe Val Gln Trp Phe Val Gly Leu Ser Pro Thr Val
            260                 265                 270

Trp Leu Ser Val Ile Trp Met Met Trp Tyr Trp Gly Pro Ser Leu Tyr
        275                 280                 285

Asn Ile Leu Asn Pro Phe Leu Pro Leu Leu Pro Ile Phe Phe Cys Leu
290                 295                 300

Trp Val Tyr Ile Xaa Thr Leu Leu Lys Pro Asn Val Gly Val Thr Pro
305                 310                 315                 320

Leu Thr Ser Trp Asp Met Xaa Leu Glu Val Gly Pro Tyr His Arg
                325                 330                 335

Asn Ile Leu Tyr Thr Lys Ser Asn
            340

```
<210> SEQ ID NO 34
<211> LENGTH: 980
<212> TYPE: DNA
```

<213> ORGANISM: hepatitis B virus

<400> SEQUENCE: 34

```
cagtccggaa ggcagcctac tcccttatct ccacctctaa gggacactca tcctcaggcc    60
atgcagtgga actccaccac tttccatcaa actcttcaag atcccagagt cagggctctg   120
tactttcctg ctggtggctc cagttcagga acagtgagcc ctgctcagaa tactgcctct   180
gccatatcgt caaccttctc gaagactggg accctgtac cgaacatgga gaacatcgca    240
tcaggactcc taggacccct gctcgcgtta caggcggggt ttttctcgtt gacaaaaatc    300
ctcacaatac cacagagtct agactcgtgg tggacttctc tcaattttct agggggaaca    360
cccgtgtgtc ttggccaaaa ttcgcagtcc caaatctcca gtcactcacc aacttgttgt    420
cctccaattt gtcctggtta tcgctggatg tgtctgcggc gttttatcat cttcctctgc    480
atcctgctgc tatgcctcat cttcttgttg gttcttctgg actatcaagg tatgttgccc    540
gtttgtcctc taattccagg atcatcaacc accagcaccg gaccatgcag aacctgcacg    600
actcctgctc aaggaacctc tatgtttccc tcatgttgct gtacaaaacc tacggacgga    660
aactgcacct gtattcccat cccatcatct gggctttcg caaaatacct atggagtgg     720
gcctcagtcc gtttctcttg gctcagttta ctagtgccgt tgttcagtg gttcgtaggg    780
ctttccccca ctgtctggct ttcagttata tggatgatgt ggtattgggg gccaagtctg    840
tacaacatct tgagtccctt tatgccgctg ttaccaattt tcttttgtct ttgggtatac    900
atttaaaccc tcacaaaaca aaaagatggg gatattccct tcaattcatg ggatatgtaa    960
ttggggggttg gggctccttg                                                980
```

<210> SEQ ID NO 35
<211> LENGTH: 258
<212> TYPE: PRT
<213> ORGANISM: hepatitis B virus

<400> SEQUENCE: 35

Glu Asp Trp Gly Pro Cys Thr Glu His Gly Glu His Arg Ile Arg Thr
1               5                   10                  15

Pro Arg Thr Pro Ala Arg Val Thr Gly Gly Val Phe Leu Val Asp Lys
            20                  25                  30

Asn Pro His Asn Thr Thr Glu Ser Arg Leu Val Val Asp Phe Ser Gln
        35                  40                  45

Phe Ser Arg Gly Asn Thr Arg Val Ser Trp Pro Lys Phe Ala Val Pro
    50                  55                  60

Asn Leu Gln Ser Leu Thr Asn Leu Leu Ser Ser Asn Leu Ser Trp Leu
65                  70                  75                  80

Ser Leu Asp Val Ser Ala Ala Phe Tyr His Leu Pro Leu His Pro Ala
                85                  90                  95

Ala Met Pro His Leu Leu Val Gly Ser Ser Gly Leu Ser Arg Tyr Val
            100                 105                 110

Ala Arg Leu Ser Ser Asn Ser Arg Ile Ile Asn His Gln His Arg Thr
        115                 120                 125

Met Gln Asn Leu His Asp Ser Cys Ser Arg Asn Leu Tyr Val Ser Leu
    130                 135                 140

Met Leu Leu Tyr Lys Thr Tyr Gly Arg Lys Leu His Leu Tyr Ser His
145                 150                 155                 160

Pro Ile Ile Leu Gly Phe Arg Lys Ile Pro Met Gly Val Gly Leu Ser
                165                 170                 175

Pro Phe Leu Leu Ala Gln Phe Thr Ser Ala Val Cys Ser Val Val Arg

```
                       180                 185                 190
Arg Ala Phe Pro His Cys Leu Ala Phe Ser Tyr Met Asp Asp Val Val
                   195                 200                 205

Leu Gly Ala Lys Ser Val Gln His Leu Glu Ser Leu Tyr Ala Ala Val
                   210                 215                 220

Thr Asn Phe Leu Leu Ser Leu Gly Ile His Leu Asn Pro His Lys Thr
225                 230                 235                 240

Lys Arg Trp Gly Tyr Ser Leu Gln Phe Met Gly Tyr Val Ile Gly Gly
                   245                 250                 255

Trp Gly

<210> SEQ ID NO 36
<211> LENGTH: 226
<212> TYPE: PRT
<213> ORGANISM: hepatitis B virus

<400> SEQUENCE: 36

Met Glu Asn Ile Ala Ser Gly Leu Leu Gly Pro Leu Leu Ala Leu Gln
1               5                   10                  15

Ala Gly Phe Phe Ser Leu Thr Lys Ile Leu Thr Ile Pro Gln Ser Leu
                20                  25                  30

Asp Ser Trp Trp Thr Ser Leu Asn Phe Leu Gly Gly Thr Pro Val Cys
            35                  40                  45

Leu Gly Gln Asn Ser Gln Ser Gln Ile Ser Ser His Ser Pro Thr Cys
        50                  55                  60

Cys Pro Pro Ile Cys Pro Gly Tyr Arg Trp Met Cys Leu Arg Arg Phe
65                  70                  75                  80

Ile Ile Phe Leu Cys Ile Leu Leu Leu Cys Leu Ile Phe Leu Leu Val
                85                  90                  95

Leu Leu Asp Tyr Gln Gly Met Leu Pro Val Cys Pro Leu Ile Pro Gly
                100                 105                 110

Ser Ser Thr Thr Ser Thr Gly Pro Cys Arg Thr Cys Thr Thr Pro Ala
            115                 120                 125

Gln Gly Thr Ser Met Phe Pro Ser Cys Cys Cys Thr Lys Pro Thr Asp
        130                 135                 140

Gly Asn Cys Thr Cys Ile Pro Ile Pro Ser Ser Trp Ala Phe Ala Lys
145                 150                 155                 160

Tyr Leu Trp Glu Trp Ala Ser Val Arg Phe Ser Trp Leu Ser Leu Leu
                165                 170                 175

Val Pro Phe Val Gln Trp Phe Val Gly Leu Ser Pro Thr Val Trp Leu
                180                 185                 190

Ser Val Ile Trp Met Met Trp Tyr Trp Gly Pro Ser Leu Tyr Asn Ile
                195                 200                 205

Leu Ser Pro Phe Met Pro Leu Leu Pro Ile Phe Phe Cys Leu Trp Val
            210                 215                 220

Tyr Ile
225

<210> SEQ ID NO 37
<211> LENGTH: 900
<212> TYPE: DNA
<213> ORGANISM: hepatitis B virus

<400> SEQUENCE: 37
cctgctggtg gctccagttc aggaacagta aaccctgttc cgactactgc ctctccctta    60
tcgtcaatct tctcgaggat tggggaccct gcgctgaaca tggagaacat cacatcagga   120
```

```
ttcctaggac ccctctcgt gttacaggcg gggttttct tgttgacaag aatcctcaca    180
ataccgcaga gtctagactc gtggtggact tctctcaatt ttcgagggg aactaccgtg    240 tgtcttggcc aaaattcgca gtccccaacc tccaatcact caccaacctc ctgtcctcca    300
acttgtcctg gttatcgctg gatgtgtctg cggcgttta tcatmttcct cttcatcctg    360
ctgctatgcc tcatcttctt gttggttctt ctggactatc raggtatgtt gcccgtttgt    420
cctctaattc caggatcctc awccaccagc acgggaccat gccgaacctg catgactact    480
gctcaaggaa cctctatgta tcccctcctgt tgctgtacca aacctacgga cggaaattgc    540
acctgtattc ccatcccatc atcctgggct ttcggaaaat tcctatggga gtgggcctca    600
gcccgtttct cctggctcag tttactagtg ccatttgttc agtggttcgt agggcttttcc    660 cccactgttt ggctttcagt tatatggatg atgtggtatt gggggccaag tctgtaymgc    720
atcttgagtc ccttttttacc gctgttacca attttctttt gtctttgggt atacatttaa    780
accctaacaa aacaaagaga tggggttact ctctgaattt tatgggttat gtcattggaa    840
gttatgggtc cttgccacaa gaacacatca tacaaaaaat caaagaatgt tttagaaaac    900
```

```
<210> SEQ ID NO 38
<211> LENGTH: 299
<212> TYPE: PRT
<213> ORGANISM: hepatitis B virus
<220> FEATURE:
<221> NAME/KEY: MISC_FEATURE
<222> LOCATION: (115)..(115)
<223> OTHER INFORMATION: n=any nucleotide
<220> FEATURE:
<221> NAME/KEY: MISC_FEATURE
<222> LOCATION: (147)..(147)
<223> OTHER INFORMATION: n=any nucleotide
<220> FEATURE:
<221> NAME/KEY: MISC_FEATURE
<222> LOCATION: (239)..(239)
<223> OTHER INFORMATION: n=any nucleotide

<400> SEQUENCE: 38
```

Cys Trp Trp Leu Gln Phe Arg Asn Ser Lys Pro Cys Ser Asp Tyr Cys
1               5                  10                  15

Leu Ser Leu Ile Val Asn Leu Leu Glu Asp Trp Gly Pro Cys Ala Glu
            20                  25                  30

His Gly Glu His His Ile Arg Ile Pro Arg Thr Pro Ser Arg Val Thr
        35                  40                  45

Gly Gly Val Phe Leu Val Asp Lys Asn Pro His Asn Thr Ala Glu Ser
    50                  55                  60

Arg Leu Val Val Asp Phe Ser Gln Phe Ser Arg Gly Asn Tyr Arg Val
65                  70                  75                  80

Ser Trp Pro Lys Phe Ala Val Pro Asn Leu Gln Ser Leu Thr Asn Leu
                85                  90                  95

Leu Ser Ser Asn Leu Ser Trp Leu Ser Leu Asp Val Ser Ala Ala Phe
            100                 105                 110

Tyr His Xaa Pro Leu His Pro Ala Ala Met Pro His Leu Leu Val Gly
        115                 120                 125

Ser Ser Gly Leu Ser Arg Tyr Val Ala Arg Leu Ser Ser Asn Ser Arg
    130                 135                 140

Ile Leu Xaa His Gln His Gly Thr Met Pro Asn Leu His Asp Tyr Cys
145                 150                 155                 160

Ser Arg Asn Leu Tyr Val Ser Leu Leu Leu Tyr Gln Thr Tyr Gly
                165                 170                 175

```
Arg Lys Leu His Leu Tyr Ser His Pro Ile Ile Leu Gly Phe Arg Lys
            180                 185                 190

Ile Pro Met Gly Val Gly Leu Ser Pro Phe Leu Leu Ala Gln Phe Thr
            195                 200                 205

Ser Ala Ile Cys Ser Val Val Arg Arg Ala Phe Pro His Cys Leu Ala
210                 215                 220

Phe Ser Tyr Met Asp Asp Val Val Leu Gly Ala Lys Ser Val Xaa His
225                 230                 235                 240

Leu Glu Ser Leu Phe Thr Ala Val Thr Asn Phe Leu Leu Ser Leu Gly
                245                 250                 255

Ile His Leu Asn Pro Asn Lys Thr Lys Arg Trp Gly Tyr Ser Leu Asn
            260                 265                 270

Phe Met Gly Tyr Val Ile Gly Ser Tyr Gly Ser Leu Pro Gln Glu His
            275                 280                 285

Ile Ile Gln Lys Ile Lys Glu Cys Phe Arg Lys
            290                 295

<210> SEQ ID NO 39
<211> LENGTH: 259
<212> TYPE: PRT
<213> ORGANISM: hepatitis B virus
<220> FEATURE:
<221> NAME/KEY: MISC_FEATURE
<222> LOCATION: (134)..(134)
<223> OTHER INFORMATION: Xaa is any amino acid
<220> FEATURE:
<221> NAME/KEY: MISC_FEATURE
<222> LOCATION: (148)..(148)
<223> OTHER INFORMATION: Xaa is any amino acid
<220> FEATURE:
<221> NAME/KEY: MISC_FEATURE
<222> LOCATION: (240)..(240)
<223> OTHER INFORMATION: Xaa is any amino acid

<400> SEQUENCE: 39

Pro Ala Gly Gly Ser Ser Gly Thr Val Asn Pro Val Pro Thr Thr Thr
1               5                   10                  15

Ala Ser Pro Leu Ser Ser Ile Phe Ser Arg Ile Gly Asp Pro Ala Leu
            20                  25                  30

Asn Met Glu Asn Ile Thr Ser Gly Phe Leu Gly Pro Leu Leu Val Leu
        35                  40                  45

Gln Ala Gly Phe Phe Leu Leu Thr Arg Ile Leu Thr Ile Pro Gln Ser
    50                  55                  60

Leu Asp Ser Trp Trp Thr Ser Leu Asn Phe Arg Gly Gly Thr Thr Val
65                  70                  75                  80

Cys Leu Gly Gln Asn Ser Gln Ser Pro Thr Ser Asn His Ser Pro Thr
                85                  90                  95

Ser Cys Pro Pro Thr Cys Pro Gly Tyr Arg Trp Met Cys Leu Arg Arg
            100                 105                 110

Phe Ile Ile Phe Leu Phe Ile Leu Leu Leu Cys Leu Ile Phe Leu Leu
            115                 120                 125

Val Leu Leu Asp Tyr Xaa Gly Met Leu Pro Val Cys Pro Leu Ile Pro
130                 135                 140

Gly Ser Ser Xaa Thr Ser Thr Gly Pro Cys Arg Thr Cys Met Thr Thr
145                 150                 155                 160

Ala Gln Gly Thr Ser Met Tyr Pro Ser Cys Cys Thr Lys Pro Thr
                165                 170                 175

Asp Gly Asn Cys Thr Cys Ile Pro Ile Pro Ser Ser Trp Ala Phe Gly
            180                 185                 190
```

```
Lys Phe Leu Trp Glu Trp Ala Ser Ala Arg Phe Ser Trp Leu Ser Leu
            195                 200                 205

Leu Val Pro Phe Val Gln Trp Phe Val Gly Leu Ser Pro Thr Val Trp
        210                 215                 220

Leu Ser Val Ile Trp Met Met Trp Tyr Trp Gly Pro Ser Leu Tyr Xaa
225                 230                 235                 240

Ile Leu Ser Pro Phe Leu Pro Leu Leu Pro Ile Phe Phe Cys Leu Trp
            245                 250                 255

Val Tyr Ile

<210> SEQ ID NO 40
<211> LENGTH: 912
<212> TYPE: DNA
<213> ORGANISM: hepatitis B virus

<400> SEQUENCE: 40
ctttcaccaa actctgcaag atcccctgc tggtggctcc agttcaggaa cagtaaaccc      60
tgttccgact actgcctctc ccttatcgtc aatcttctcg aggattgggg accctgcgcg    120
gaacatggag aacatcacat caggattcct aggaccccctt ctcgtgttac aggcggggtt   180
tttcttgttg acaagaatcc tcacaatacc gcagagtcta gactcgtggt ggacttctct    240
caattttcta gggggaacta ccgtgtgtct tggccaaaat tcgcagtccc caacctccaa    300
tcactcacca acctcctgtc ctccaacttg tcctggttat cgctggatgt gtctgcggcg    360
ttttatcatc ttcctcttca tcctgctgct atgcctcatc ttcttgttgg ttcttctgga    420
ctatcraggt atgttgcccg tttgtcctct aattccagga tcctcaacca ccagcacggg    480
accatgccga acctgcatga ctactgctca aggaacctct atgtatccct cctgttgctg    540
taccaaacct acggacggaa attgcacctg tattcccatc ccatcatcct gggctttcgg    600
aaaattccta tgggagtggg cctcagcccg tttctcctgg ctcagtttac tagtgccatt    660
tgttcagtgg ttcgtagggc tttcccccac tgtttggctt tcagttatat ggatgatgtg    720
gtattggggg ccaagtctgy acagcatctt gagtcccttt ttaccgcggt gaccaatttt    780
cttttgtctt tgggtataca tttaaaccct aacaaaacaa agagatgggg ttactctctg    840
aattttatgg gttatgtcat tggaagttat gggtccttgc acaagaaca catcatacaa     900
aaaatcaaag aa                                                        912

<210> SEQ ID NO 41
<211> LENGTH: 304
<212> TYPE: PRT
<213> ORGANISM: hepatitis B virus
<220> FEATURE:
<221> NAME/KEY: MISC_FEATURE
<222> LOCATION: (247)..(247)
<223> OTHER INFORMATION: Xaa is any amino acid

<400> SEQUENCE: 41

Leu Ser Pro Asn Ser Ala Arg Ser Pro Cys Trp Trp Leu Gln Phe Arg
1               5                   10                  15

Asn Ser Lys Pro Cys Ser Asp Tyr Cys Leu Ser Leu Ile Val Asn Leu
            20                  25                  30

Leu Glu Asp Trp Gly Pro Cys Ala Glu His Gly Glu His His Ile Arg
        35                  40                  45

Ile Pro Arg Thr Pro Ser Arg Val Thr Gly Gly Val Phe Leu Val Asp
    50                  55                  60

Lys Asn Pro His Asn Thr Ala Glu Ser Arg Leu Val Val Asp Phe Ser
65                  70                  75                  80
```

```
Gln Phe Ser Arg Gly Asn Tyr Arg Val Ser Trp Pro Lys Phe Ala Val
                85                  90                  95

Pro Asn Leu Gln Ser Leu Thr Asn Leu Leu Ser Ser Asn Leu Ser Trp
            100                 105                 110

Leu Ser Leu Asp Val Ser Ala Ala Phe Tyr His Leu Pro Leu His Pro
        115                 120                 125

Ala Ala Met Pro His Leu Leu Val Gly Ser Ser Gly Leu Ser Arg Tyr
    130                 135                 140

Val Ala Arg Leu Ser Ser Asn Ser Arg Ile Leu Asn His Gln His Gly
145                 150                 155                 160

Thr Met Pro Asn Leu His Asp Tyr Cys Ser Arg Asn Leu Tyr Val Ser
                165                 170                 175

Leu Leu Leu Leu Tyr Gln Thr Tyr Gly Arg Lys Leu His Leu Tyr Ser
            180                 185                 190

His Pro Ile Ile Leu Gly Phe Arg Lys Ile Pro Met Gly Val Gly Leu
        195                 200                 205

Ser Pro Phe Leu Leu Ala Gln Phe Thr Ser Ala Ile Cys Ser Val Val
    210                 215                 220

Arg Arg Ala Phe Pro His Cys Leu Ala Phe Ser Tyr Met Asp Asp Val
225                 230                 235                 240

Val Leu Gly Ala Lys Ser Xaa Gln His Leu Glu Ser Leu Phe Thr Ala
                245                 250                 255

Val Thr Asn Phe Leu Leu Ser Leu Gly Ile His Leu Asn Pro Asn Lys
            260                 265                 270

Thr Lys Arg Trp Gly Tyr Ser Leu Asn Phe Met Gly Tyr Val Ile Gly
        275                 280                 285

Ser Tyr Gly Ser Leu Pro Gln Glu His Ile Ile Gln Lys Ile Lys Glu
    290                 295                 300

<210> SEQ ID NO 42
<211> LENGTH: 266
<212> TYPE: PRT
<213> ORGANISM: hepatitis B virus
<220> FEATURE:
<221> NAME/KEY: MISC_FEATURE
<222> LOCATION: (142)..(142)
<223> OTHER INFORMATION: Xaa is any amino acid
<220> FEATURE:
<221> NAME/KEY: MISC_FEATURE
<222> LOCATION: (247)..(247)
<223> OTHER INFORMATION: Xaa is any amino acid

<400> SEQUENCE: 42

Phe His Gln Thr Leu Gln Asp Pro Ala Gly Gly Ser Ser Ser Gly
1               5                   10                  15

Thr Val Asn Pro Val Pro Thr Thr Ala Ser Pro Leu Ser Ser Ile Phe
            20                  25                  30

Ser Arg Ile Gly Asp Pro Ala Arg Asn Met Glu Asn Ile Thr Ser Gly
        35                  40                  45

Phe Leu Gly Pro Leu Leu Val Leu Gln Ala Gly Phe Phe Leu Leu Thr
    50                  55                  60

Arg Ile Leu Thr Ile Pro Gln Ser Leu Asp Ser Trp Trp Thr Ser Leu
65                  70                  75                  80

Asn Phe Leu Gly Gly Thr Thr Val Cys Leu Gly Gln Asn Ser Gln Ser
                85                  90                  95

Pro Thr Ser Asn His Ser Pro Thr Ser Cys Pro Pro Thr Cys Pro Gly
            100                 105                 110
```

```
Tyr Arg Trp Met Cys Leu Arg Arg Phe Ile Ile Phe Leu Phe Ile Leu
        115             120             125

Leu Leu Cys Leu Ile Phe Leu Leu Val Leu Leu Asp Tyr Xaa Gly Met
        130             135             140

Leu Pro Val Cys Pro Leu Ile Pro Gly Ser Ser Thr Thr Ser Thr Gly
145             150             155             160

Pro Cys Arg Thr Cys Met Thr Thr Ala Gln Gly Thr Ser Met Tyr Pro
            165             170             175

Ser Cys Cys Cys Thr Lys Pro Thr Asp Gly Asn Cys Thr Cys Ile Pro
            180             185             190

Ile Pro Ser Ser Trp Ala Phe Gly Lys Phe Leu Trp Glu Trp Ala Ser
        195             200             205

Ala Arg Phe Ser Trp Leu Ser Leu Leu Val Pro Phe Val Gln Trp Phe
        210             215             220

Val Gly Leu Ser Pro Thr Val Trp Leu Ser Val Ile Trp Met Met Trp
225             230             235             240

Tyr Trp Gly Pro Ser Leu Xaa Ser Ile Leu Ser Pro Phe Leu Pro Arg
            245             250             255

Pro Ile Phe Phe Cys Leu Trp Val Tyr Ile
            260             265
```